United States Patent [19]
Magda et al.

[11] Patent Number: 5,567,687
[45] Date of Patent: Oct. 22, 1996

[54] TEXAPHYRINS AND USES THEREOF

[75] Inventors: Darren Magda, Cupertino, Calif.; Jonathan L. Sessler, Austin, Tex.; Brent Iverson, Austin, Tex.; Petra L. Jansen, Austin, Tex.; Meredith Wright, San Jose, Calif.; Tarak D. Mody, Sunnyvale, Calif.; Gregory W. Hemmi, Sunnyvale, Calif.

[73] Assignees: University of Texas, Austin, Tex.; Pharmacyclics, Inc., Sunnyvale, Calif.

[21] Appl. No.: 310,501

[22] Filed: Sep. 21, 1994

Related U.S. Application Data

[63] Continuation-in-part of Ser. No. 112,872, Aug. 25, 1993, Pat. No. 5,451,576, a continuation-in-part of PCT/US94/06284 Jun. 9, 1994, said Ser. No. 112,872 which is a division of Ser. No. 822,964, Jan. 21, 1992, Pat. No. 5,242,720, said PCT/US94/06284, Ser. No. 227,370, Apr. 14, 1994, which is a continuation-in-part of Ser. No. 75,123, Jun. 9, 1993, abandoned, which is a continuation-in-part of Ser. No. 822,964, Jan. 21, 1992, Pat. No. 5,252,720, which is a continuation-in-part of Ser. No. 771,393, Sep. 30, 1991, abandoned, which is a continuation of PCT/US90/01208, Mar. 6, 1990, which is a continuation-in-part of Ser. No. 539,975, Jun. 18, 1990, Pat. No. 5,162,509, which is a division of Ser. No. 320,293, Mar. 6, 1989, Pat. No. 4,935,498, said Ser. No. 112,872, is a division of Ser. No. 822,964.

[51] Int. Cl.[6] .................................................. C07D 487/22
[52] U.S. Cl. ..................... 514/44; 204/157.68; 536/23.1; 536/24.2
[58] Field of Search ........................... 514/44; 536/23.1, 536/24.2; 204/157.68

[56] References Cited

U.S. PATENT DOCUMENTS

| | | | |
|---|---|---|---|
| 4,647,447 | 3/1987 | Gries et al. | 424/9 |
| 4,878,891 | 11/1989 | Judy et al. | 604/5 |
| 4,880,008 | 11/1989 | Lauffer | 128/654 |
| 4,883,790 | 11/1989 | Levy et al. | 540/145 |
| 4,899,755 | 2/1990 | Lauffer et al. | 128/654 |
| 4,915,683 | 4/1990 | Sieber | 604/4 |
| 4,935,498 | 6/1990 | Sessler et al. | 534/15 |
| 4,959,363 | 9/1990 | Wentland | 514/235 |
| 4,977,177 | 12/1990 | Bommer et al. | 514/410 |
| 5,021,236 | 6/1991 | Gries et al. | 424/9 |
| 5,030,200 | 7/1991 | Judy et al. | 604/5 |
| 5,041,078 | 8/1991 | Matthews et al. | 604/4 |
| 5,162,509 | 11/1992 | Sessler et al. | 534/15 |
| 5,252,720 | 10/1993 | Sessler et al. | 534/11 |
| 5,256,399 | 10/1993 | Sessler et al. | 424/9 |
| 5,272,142 | 12/1993 | Sessler et al. | 514/185 |
| 5,292,414 | 3/1994 | Sessler et al. | 204/157.5 |
| 5,302,714 | 4/1994 | Sessler et al. | 540/472 |
| 5,432,171 | 7/1995 | Sessler et al. | 514/185 |
| 5,439,570 | 8/1995 | Sessler et al. | 204/157.15 |
| 5,451,576 | 9/1995 | Sessler et al. | 514/185 |

FOREIGN PATENT DOCUMENTS

| | | |
|---|---|---|
| 0111418A2 | 6/1984 | European Pat. Off. . |
| 0196515A1 | 1/1986 | European Pat. Off. . |
| 0214908 | 3/1987 | European Pat. Off. . |
| 0233701A2 | 8/1987 | European Pat. Off. . |
| 2697254 | 4/1994 | France . |
| WO90/02747 | 3/1990 | WIPO . |
| WO90/10633 | 9/1990 | WIPO . |
| WO92/10633 | 9/1990 | WIPO . |
| WO91/19730 | 12/1991 | WIPO . |
| WO92/01781 | 2/1992 | WIPO . |
| WO93/14093 | 7/1993 | WIPO . |
| WO94/29316 | 12/1994 | WIPO . |
| WO95/21845 | 8/1995 | WIPO . |

OTHER PUBLICATIONS

Casas et al., "Preparation of Hybrid" DNA Cleaver–Oligonucleotide Molecules Based on a Metallotris(methylpyridiniumyl)porphyrin Motif, *Bioconjugate Chem.*, 4:366–371 (1993).

International Search Report dated Feb. 9, 1996.

Agrawal et al., "Cellular Uptake and Anti–HIV Activity of Oligonucleotides and Their Analogs," *Gene Regulation: Biology of Antisense RNA and DNA*, 273–283, 1992.

Agrawal and Tang, "Efficient Synthesis of Oligoribonucleotide and Its Phosphorothioate Analogue Using H–Phosphonate Approach," *Tetrahedron Letters*, 31(52):7541–7544, 1990.

Akhtar et al., "Pharmaceutical Aspects of the Biological Stability and Membrane Transport Characteristics of Antisense Oligonucleotides," *Gene Regulation: Biology of Antisense RNA and DNA*, 133–145, 1992.

Basile et al., "Metal–Activated Hydrolytic Cleavage of DNA," *J. Am. Chem. Soc.*, 109:7550–7551, 1987.

Bradley et al., "Antisense Therapeutics," *Gene Regulation: Biology of Antisense RNA and DNA*, 285–293, 1992.

Breslow et al., "Effects of Metal Ions, Including $Mg^{2+}$ and Lanthanides, on the Cleavage of Ribonucleotides and RNA Model Compounds," *Proc. Natl. Acad. Sci. USA*, 88:4080–4083, 1991.

Browne and Bruice, "Chemistry of Phosphodiesters, DNA and Models. 2. The Hydrolysis of Bis(8–hydroxyquinoline) Phosphate in the Absence and Presence of Metal Ions," *Journal of the American Chemical Society*, 114(13):4951–4958, 1992.

Chin and Banaszczyk, "Rate–Determining Complexation in Catalytic Hydrolysis of Unactivated Esters in Neutral Water," *J. Am. Chem. Soc.*, 111:2724–2726, 1989.

(List continued on next page.)

*Primary Examiner*—Richard L. Raymond
*Attorney, Agent, or Firm*—Arnold, White & Durkee

[57] ABSTRACT

A texaphyrin having substituents containing ethoxy groups, methods for using texaphyrins in photodynamic therapy, and cleavage of a polymer of deoxyribonucleic acid are disclosed. The in vivo treatment of tumors and atheroma is demonstrated using Lu(III)texaphyrin complexes. A preferred method of use is the site-specific cleavage of a polymer of deoxyribonucleic acid and a preferred texaphyrin is a derivatized texaphyrin having binding specificity, in particular, a texaphyrin covalently coupled to a site-directing molecule, preferably an oligonucleotide.

13 Claims, 28 Drawing Sheets

OTHER PUBLICATIONS

Chin and Banaszczyk, "Highly Efficient Hydrolytic Cleavage of Adenosine Monophosphate Resulting in a Binuclear Co(III) Complex with a Novel Doubly Bidentate $\mu^4$–Phosphato Bridge," *J. Am. Chem. Soc.*, 111:4103–4105, 1989.

Chin et al., "Co(III) Complex Promoted Hydrolysis of Phosphate Diesters: Comparison in Reactivity of Rigid cis–Diaquotetraazacobalt(III) Complexes," *J. Am. Chem. Soc.*, 111:186–190, 1989.

Chin and Zou, "Catalytic Hydrolysis of cAMP," *Can. J. Chem.*, 65:1882–1884, 1987.

Chung et al., "Synthesis and Characterization of a Reactive Binuclear Co(III) Complex. Cooperative Promotion of Phosphodiester Hydrolysis," *Tetrahedron Letters*, 31(38):5413–5416, 1990.

Cohen, Jack S., "Chemically Modified Oligodeoxynucleotide Analogs as Regulators of Viral and Cellular Gene Expression," *Gene Regulation: Biology of Antisense RNA and DNA*, 247–259, 1992.

Furuta et al., "Phosphate Anion Binding: Enhanced Transport of Nucleotide Monophosphates Using a Sapphyrin Carrier," *J. Am. Chem. Soc.*, 113:6677–6678, 1991.

Hanvey, et al., "Antisense and Antigene Properties of Peptide Nucleic Acids," *Science*, 258:1481–1485, 1992.

Hendry and Sargeson, "Metal Ion Promoted Phosphate Ester Hydrolysis. Intramolecular Attack of Coordinated Hydroxide Ion," *J. Am. Chem. Soc.*, 111:2521–2527, 1989.

Kim and Chin, "Dimethyl Phosphate Hydrolysis at Neutral pH," *J. Am. Chem. Soc.*, 114:9792–9795, 1992.

Komiyama et al., "Unprecedentedly Fast Hydrolysis of the RNA Dinucleoside Monophosphates ApA and UpU by Rare Earth Metal Ions," *J. Chem. Soc. Chem. Commun.*, 640–641, 1992.

Menger et al., "Phosphate Ester Hydrolysis Catalyzed by Metallomicelles," *J. Am. Chem. Soc.*, 109:2800–2803, 1987.

Modak et al., "Toward Chemical Ribonucleases. 2. Synthesis and Characterization of Nucleotide–Bipyridine Conjugates. Hydrolytic Cleavage of RNA by Their Copper(II) Complexes," *J. Am. Chem. Soc.*, 113:283–291, 1991.

Morrow et al., "Efficient Catalytic Cleavage of RNA by Lanthanide(III) Macrocyclic Complexes: Toward Synthetic Nucleases for in Vivo Applications," *J. Am. Chem. Soc.*, 114:1903–1905, 1992.

Ranganathan et al., "Design of a Chemical Nuclease Model with (Lys)$_2$Cu as the Core Motif," *Journal of the Chemical Society*, 4:337–339, 1993.

Sessler and Burrell, "Expanded Porphyrins," *Topics in Current Chemistry*, 161:180–273, 1991.

Sessler et al., "Sapphyrins: New Life for an Old Expanded Porphyrin," *Synlett*, 127–134, 1991.

Sessler et al., "Sapphyrins and Heterosapphyrins," *Tetrahedron*, 48(44):9661–9672, 1992.

Shelton and Morrow, "Catalytic Transesterification and Hydrolysis of RNA by Zinc(II) Complexes," *Inorganic Chemistry*, 30:4295–4299, 1991.

Stern et al., "Hydrolysis of RNA by Transition–Metal Complexes," *J. Am. Chem. Soc.*, 112:5357–5359, 1990.

Sumaoka et al., "Remarkably Fast Hydrolysis of 3', 5'–Cyclic Adenosine Monophosphate by Cerium(III) Hydroxide Cluster," *J. Chem. Soc. Chem. Comm.*, 2 pages, 1992.

To and Neiman, "The Potential for Effective Antisense Inhibition of Retroviral Replication Mediated by Retroviral Vectors," *Gene Regulation: Biology of Antisense RNA and DNA*, 261–271, 1992.

Dialog Search Report dated Jun. 9, 1993, printed in USA.

Shelton and Morrow, "Catalytic Transesterification and Hydrolysis of RNA by Zinc(II) Complexes," *Inorg. Chem.*, 30:4295–4299, 1991.

Sessler et al., "Synthesis and Structural Characterization of Lanthanide(III) Texaphyrins," *Inorganic Chemistry*, 32(14):3175–3187, 1993.

Phillips and Wasserman, "Promise of Radiosensitizers and Radioprotectors in the Treatment of Human Cancer," *Cancer Treatment Reports*, 68(1):291–301, 1984.

Wagener and Beyrich, "Radiosensitizer–Biochemie und Tumortherapeutische Erfahrungen," *Pharmazie*, 47:815–824, 1992.

Kolasa et al., "Trivalent Lanthanide Ions Do Not Cleave RNA in DNA–RNA Hybrids", *Inorg. Chem.*, 32:3983–3984, 1993.

Schneider et al., "Catalysis of the Hydrolysis of Phosphoric Acid Diesters b Lanthanide Ions and the Influence of Ligands," *Angew. Chem. Int. Ed. Engl.*, 32(12):1716–1719, 1993.

Hayashi et al., "Site–Selective Hydrolysis of tRNA by Lanthanide Metal Complexes," *Inorg. Chem.*, 32:5899–5900, 1993.

Sessler et al., "Gadolinium(III) Texaphyrin: A Novel MRI Contrast Agent," *Journal of the American Chemical Society*, 115(22):10368–10369, 1993.

Magda et al., "Site-Specific Hydrolysis of RNA by Europium(III) Texaphyrin Conjugated to a Synthetic Oligodeoxyribonucleotide," *Journal of the American Chemical Society*, 116(16):7439–7440, 1994.

Mody et al., "Lutetium(III) Texaphyrin: A Novel Photodynamic Therapy Agents," *Biosis Biosciences Information Service*, Abstract No. 94:379967.

Koenig et al., "PDT of Tumor–Bearing Mice Using Liposome Delivered Texaphyrins," *Biosis Biosciences Information Service*, Abstract No. 93:218413.

Iverson et al., "Interactions Between Expanded Porphyrins and Nucleic Acids," *Chemical Abstracts*, 121(19), Abstract No. 224420, 1994.

Young et al., "Preclinical Evaluation of Gadolinium (III) Texaphyrin Complex. A New Paramagnetic Contrast Agent for Magnetic Resonance Imaging," *Medline US National Library of Medicine (NLM)*, Abstract No. 94229933.

Matthews et al., "Inactivation of Viruses with Photoactive Compounds," *Chemical Abstracts*, 117(3), Abstract No. 22546, 1992.

Ehrenberg et al., "Spectroscopy, Photokinetics and Cellular Effect of Far–Red and Near Infrared Absorbing Photosenstizers," *Chemical Abstracts*, 117(17), Abstract No. 166777, 1992.

Thaller et al., "Potential Use of Radiolabelled Porphyrins for Tumor Scanning," *Porphyrin Photosensitization*, Kessel and Dougherty, Editors, Plenum Press, New York, Publishers, pp. 265–278, 1983.

Magda et al., "Sequence–Specific Photocleavage of DNA by an Expanded Porphyrin with Irradiation Above 700 nm," *J. Am. Chem. Soc.*, 117:3629–3630, 1995.

Sessler et al., "Expanded Porphyrins. Receptors for Cationic, Anionic, and Neutral Substrates," in Transition Metals in Supramolecular Chemistry, L. Fabbrizzi and A. Poggi, Editors, NATO ASI Series, Kluwer, Amsterdam, pp. 391–408, 1994. Bhan and Miller, "Photo–Cross Linking of Psoralen–Derivatized Oligonucleoside Methylphosphonates to Single–Stranded DNA," *Bioconjugate Chem.*, 1:82–88, 1990.

Boutorine et al., "Fullerene–Oligonucleotide Conjugates: Photo–Induced Sequence Specific DNA Cleavage", *Agnew. Chem. Int. Ed. Engl.*, 33 (23/24):2462–2465, 1994.

Dolphin et al., "Porphocyanine: An Expanded Tetrapyrrolic Macrocycle," *J. Am. Chem. Soc.*, 115:9301–9302, 1993.

Ehrenberg et al., "Spectroscopy, Photokinetics and Cellular Effect of Far-Red and Near Infrared Absorbing Photosensitizers," *Proc. SPIE*, 1645:259–263, 1992.

Ehrenberg et al., "The Binding and Photosensitization Effects of Tetrabenzoporphyrins and Texaphyrin in Bacterial Cells," *Lasers in Medical Science*, 8:197–203, 1993.

Le Doan et al., "Sequence–Targeted Photochemical Modifications of Nucleic Acids by Complementary Oligonucleotides Covalently Linked to Porphyrins," *Bioconjugate Chem.*, 1:108–113, 1990.

Le Doan et al., "Sequence–Specific Recognition, Photocrosslinking and Cleavage of the DNA Double Helix by an Oligo–[α]–Thymidylate Covalently Attached to an Azidoproflavine," *Nucleic Acids Res.*, 15:7749–7760, 1987.

Levina et al., "Photomodification of RNA and DNA Fragments by Oligonucleotide Reagents Bearing Arylazide Groups," *Biochimie*, 75:25–27, 1993.

Mastruzzo et al., "Targeted Photochemical Modification of HIV–Derived Oligoribonucleotides by Antisense Oligodeoxynucleotides Linked to Porphyrins," *Photochem. Photobiol.*, 60(4):316–322, 1994.

Fedorova et al., "Palladium(II)–Coproporphyrin I as a Photoactivable Group in Sequence–Specific Modification of Nucleic Acids by Oligonucleotide Derivatives," *FEBS Lett.*, 259(2):335–337, 1990.

Morgan and Skalkos, "Second Generation Sensitizers: Where are We and Where Should We Be Going?" *Proc. SPIE Int. Soc. Opt. Eng. Ser.*, 6:87–106, 1990.

Perrouault et al., "Sequence–Specific Artificial Photo–Induced Endonucleases Based on Triple Helix–Forming Oligonucleotides," *Nature*, 344:358–360, 1990.

Pieles and Englisch, "Psoralen Covalently Linked to Oligodeoxyribonucleotides: Synthesis, Sequence Specific Recognition of DNA and Photo–Cross–Linking to Pyrimidine Residues of DNA," *Nucleic Acids Res.*, 17(1):285–299, 1989.

Praseuth et al., "Sequence–Targeted Photosensitized Reactions in Nucleic Acids by Oligo–α–Deoxynucleotides and Oligo–β–Deoxynucleotides Covalently Linked to Proflavin," *Biochemistry*, 27:3031–3038, 1988.

Praseuth et al., "Sequence–Specific Binding and Photocrosslinking of α and β Oligodeoxynucleotides to the Major Groove of DNA via Triple–Helix Formation," *Proc. Natl. Acad. Sci. USA*, 85:1349–1353, 1988.

Takasugi et al., "Sequence–Specific Photo–Induced Cross–Linking of the Two Strands of Double–Helical DNA by a Psoralen Covalently Linked to a Triple Helix–Forming Oligonucleotide," *Proc. Natl. Acad. Sci. USA*, 88:5602–5606, 1991.

Teare and Wollenzien, "Specificity of Site Directed Psoralen Addition to RNA," *Nucleic Acids Res.*, 17(9):3359–3372, 1989.

Vogel et al., "New Porphycene Ligands: Octaethyl–and Etioporphycene (OEPc and EtioPc)–Tetra– and Pentacoordinated Zinc Complexes of OEPc," *Angew. Chem. Int. Ed. Engl.*, 32(11):1600–1604, 1993.

Wessel et al., "Porphyrins with Aromatic 26π–Electron Systems," *Angew. Chem. Int. Ed. Eng.*, 32(8):1148–1151, 1993.

Abid et al., "Lanthanide Complexes of Some Macrocyclic Schiff Bases Derived from Pyridine–2,6–dicarboxaldehyde and α,ω–Primary Diamines", *Inorg. Chim. Acta*, vol. 95, (1984) 119–125.

Acholla et al., "Binucleating Tetrapyrrole Macrocycles", *J. Am. Chem. Soc.*, vol. 107 (1985) 6902–6908.

Acholla et al., "A Binucleating "Accordian" Tetrapyrrole Macrocycle", *Tetrahedron Lett.*, vol. 25 (1984) 3269–3270.

Ansell, "X–Ray Crystal Structure of the Pentagonal Bipyramidal Nickel(11) Complex $[Ni^{11}(L)(H_2O)_2](BF_4)_2$ and the Selective Stabilisation of the Nickel(1) Oxidation State by a Quinquedentate Macrocyclic Ligand", *J. Chem. Soc., Chem. Commun.* (1982) 546–547.

Bauer et al., "Sapphyrins: Novel Aromatic Pentapyrrolic Macrocycles", *J. Am. Chem. Soc.*, vol. 105, (1983) 6429–6436.

Broadhurst et al., "Preparation of Some Sulphur–containing Polypyrrolic Macrocycles. Sulphur Extrusion from a meso–Thiaphlorin", *J. Chem. Soc., Chem. Commun.* (1970) 807–809.

Broadhurst et al., "18–and 22–π–Electron Macrocycles Containing Furan, Pyrrole, and Thiophene Rings", *J. Chem. Soc., Chem. Commun.* (1969) 1480–1482.

Broadhurst et al., "New Macrocyclic Aromatic Systems Related to Porphins", *J. Chem. Soc., Chem. Commun.* (1969) 23–24.

Broadhurst et al., "The Synthesis of 22 π–Electron Macrocycles. Sapphyrins and Related Compounds", *J. Chem. Soc. Perkin Trans.* 1 (1972) 2111–2116.

Cuellar et al., "Synthesis and Characterization of Metallo and Metal–Free Octaalkylphthalocyanines and Uranyl Decaalkysuperphthalocyanines", *Inorg. Chem.*, vol. 20 (1981) 3766–3770.

Day et al., "Large Metal Ion–Centered Template Reactions. A Uranyl Complex of Cyclopentakis (2–iminoisoindoline)", *J. Am. Chem. Soc.*, vol. 97 (1975) 4519–4527.

De Cola et al., "Hexaaza Macrocyclic Complexes of the Lanthanides", *Inorg. Chem.*, vol. 25 (1986) 1729–1732.

Dougherty, "Photosensitizers: Therapy and Detection of Malignant Tumors", *Photochem. Photobiol.*, vol. 45 (1987) 879–889.

Gosmann et al., "Synthesis of Fourfold Enlarged Porphyrin with an Extremely Large, Diamagnetic Ring–Current Effect", *Angew. Chem., Int. Ed Engl.*, vol. 25 (1986) 1100–1101.

Gossauer, "Syntheses of Some Unusual Polypyrrole Macrocycles", *Bull. Soc. Chim. Belg.*, vol. 92 (1983) 793–795.

Knubel et al., "Biomimetic Synthesis of an octavinylogous Porphyrin with an Aromatic [34] Annulene System", *Angew. Chem., Int. Ed. Engl.*, vol. 27 (1988) 1170–1172.

Lauffer, "Paramagnetic Metal Complexes as Water Proton Relaxation Agents for NMR Imaging: Theory and Design", *Chem. Rev.* vol. 87 (1987) 901–927.

LeGoff et al., "Synthesis of a [1,5,1,5] Platyrin, a 26 π–Electron Tetrapyrrolic Annulene", *J. Org. Chem.* vol. 52 (1987) 710–711.

Marks et al., "Large Metal Ion–Centered Template Reactions. Chemical and Spectral Studies of the "Superphthalocyanine" Dioxocyclopentakis (1–iminoisoindolinato) uranium (VI) and Its Derivatives", *J. Am. Chem. Soc.*, vol. 100 (1978) 1695–1705.

Rexhausen et al., "The Synthesis of a New 22 π–Electron Macrocycle: Pentaphyrin", *J. Chem. Soc., Chem. Commun.* (1983) 275.

Sessler et al., "Synthesis and Crystal Structure of a Novel Tripyrrane–Containing Porphyrinogen–like Macrocycle", *J. Org. Chem.*, vol. 52 (1987) 4394–4397.

Sessler et al., "The Coordination Chemistry of Planar Pentadentate "Porphyrin–Like" Ligands", *Comm. Inorg. Chem.*, vol. 7 (1988) 333–350.

Sessler et al., "An Expanded Porphyrin": The Synthesis and Structure of a New Aromatic Pentadentate Ligand", *J. Am. Chem. Soc.*, vol. 110 (1988) 5586–5588.

Tweedle et al., "Principles of Contrast–Enhanced MRI", in *Magnetic Resonance Imaging*, 2nd ed. Partain, et al., Eds., W. B. Saunders: Philadelphia, vol. I (1988) 793–809.

Vogel et al., "Porphycene—a Novel Porphin Isomer", *Angew. Chem., Int. Ed. Engl.*, vol. 25 (1986) 257–259.

Vogel et al., "2,7,12,17–Tetrapropylporphycene—Counterpart of Octaethylporphyrin in the Porphycene Series", *Angew. Chem., Int. Ed. Engl.*, vol. 26 (1987) 928–931.

Sessler et al., "A Water–Stable Gadolinium (III) Complex Derived from a New Pentadentate "Expanded Porphyrin" Ligand, *Inorg. Chem.*, vol. 28 (1989) 3390–3393.

Sessler et al., "Binding of Pyridine and Benzimidazole to a Cadmium Expanded Porphyrin: Solution and X–ray Structural Studies", *Inorg. Chem.*, vol. 28 (1989) 1333–1341.

Harriman et al., "Metallotexaphyrins: A New Family of Photosensitisers for Efficient Generation of Singlet Oxygen", *J. Chem. Soc., Chem. Commun.*, (1989) 314–316.

Sessler et al., "Expanded Porphyrins: The synthesis and Metal Binding Properties of Novel Tripyrrane–Containing Macrocycles", *J. Coord. Chem.*, vol. 18 (1988) 99–104.

Sessler et al., "A Water–Stable Gadolinium (III) Complex Derived from a New Pentadentate", *Chem. Absts.*, vol. 111:125716e (2 Oct. 1989) p. 720.

Sessler et al., "The Synthesis and Structure of a Novel 22 π–Electron Aromatic Pentadentate Macrocyclic Ligand: An Expanded Porphyrin", Toronto ACS Meeting, Jun. 1988.

Sessler et al., "'Texaphyrin': A Novel 22 π–Electron Aromatic Pentadentate Macrocyclic Ligand", ACS meeting, Los Angeles, Sep. 1988.

Stinson, "Unusual Porphyrin Analog Promises Many Applications", *Chemical and Engineering News*, Aug. 8, 1988, pp. 26–27.

Sessler et al., "Tripyrroledimethine–derived ("Texaphyrin"–type) Macrocycles: Potential Photosensitizers Which Absorb in the Far–red Spectral Region", *SPIE*, vol. 1426, Optical Methods for Tumor Treatment and Early Diagnosis: Mechanism and Technique (1991) 318–329.

"2–Äthylamino–2–methyl–propanol–(1)", *Beilstein's Handbuch*, vol. 4 (1950) p. 785.

"Tentative Rules for Carbohydrate Nomenclature Part 1 (1969)," *Handbook of Biochemistry and Molecular Biology*, 3rd ed., Fasman, Ed., CRC Press, Cleveland, Ohio.

Sessler et al., "Preparation of Lanthanide (III) Texaphyrin Complexes and Their Applications to Magnetic Resonance Imaging and Photodynamic Therapy," Abstracts of Papers, Part 1, 204th ACS National Meeting, Aug. 23–28, 1992, Washington, DC.

Sessler et al., "Synthesis and Applications of Schiff–Base Derived "Expanded Porphyrins," *Abstracts of Papers*, Part 1, 204th ACS National Meeting, Aug. 23–28, 1992, Washington, DC.

Sessler et al., "Texaphyrins: Synthesis and Applications," *Accounts of Chemical Research*, 27(2):43–50, 1994.

Goodchild, John, "Conjugates of Oligonucleotides and Modified Oligonucleotides: A Review of Their Synthesis and Properties," *Bioconjugate Chemistry*, 1(3): 165–187, 1990.

Kobayashi et al., "Uptake of Chlorophyll–Derivatives by Cellular Nuclei and Mitochondria," *Photomed. Photobiol.*, 15:75–84, 1993.

Brown and Truscott, "New Light on Cancer Therapy," *Chemistry in Britain*, 955–958, 1993.

Lin et al., "Use of EDTA Derivatization to Characterize Interactions between Oligodeoxyribonucleoside Methlphosphonates and Nucleic Acids," *Biochemistry*, 28:1054–1061, 1989.

Strobel and Dervan, "Cooperative Site Specific Binding of Oligonucleotides to Duplex DNA," *Journal of the American Chemical Society*, 111(18):7286–7287, 1989.

Dreyer and Dervan, "Sequence–specific Cleavage of Single–Stranded DNA: Oligodeoxynucleotide–EDTA Fe(II)," *Proc. Natl. Acad. Sci, USA*, 82: 968–972, 1985.

Doan et al., "Sequence–targeted Chemical Modifications of Nucleic Acids by Complementary Oligonucleotides Covalently Linked to Porphyrins," *Nucleic Acids Research*, 15(21): 8643–8659, 1987.

Doan et al., "Targeted Cleavage of Polynucleotides by Complementary Oligonucleotides Covalently Linked to Iron–Prophyrins," *Biochemistry*, 26:6736–6739, 1986.

Dervan, Peter B., "Design of Sequence–Specific DNA–Binding Molecules," *Science*, 232:464–471, 1986.

Groves and Farrell, "DNA Cleavage by a Metal Chelating Tricationic Porphyrin," *J. Am. Chem. Soc.*, 111:4998–5000, 1989.

Fiel, Robert J., "Porphyrin–Nucleic Acid Interactions: A Review," *Journal of Biomolecular Structure & Dynamics*, 6(6):1259–1275, 1989.

Vlassov et al., "Photoactivatable Porphyrin Oligonucletide Derivatives for Sequence Specific Chemical Modification and Cleavage of DNA," *Nucleosides & Nucleotides*, 10(1–3):641–643, 1991.

Zuk et al., "Pharmacokinetic and Tissue Distribution Studies of the Photosensitizer bis(Di–Isobutyl Octadecysiloxy) Silicon 2,3–Naphthalocyanine (isoBosinc) in Normal and Tumor–Bearing Rats," *Photochemistry and Photobiology*, 59(1):66–72, 1994.

Lee et al., "Interaction of Psoralen–Derivatized Oligodeoxyribonucleoside Methylphosphonates with Single–Stranded DNA," *Biochemistry*, 27:3197–3203, 1988.

T. D. Mody et al., "Lutetium (III) Texaphyrin: A Novel Photodynamic Therapy Agent," Abstract, *22nd Annual American Society for Photobiology*, Scottsdale, AZ, Jun. 25–29, 1994.

Sessler and Burrell, "Expanded Porphyrins," *Topics in Current Chemistry*, 161:180–273, 1991.

Sessler et al., "Synthesis and Structural Characterization of Lanthanide(III) Texaphyrins," *Inorganic Chemistry*, 32(14):3175–3187, 1993.

Sessler, Jonathan L., "Texas–Sized Molecule," *Discovery*, 13(1):44–49, 1993.

Sessler et al., "Photodynamic Inactivation of Enveloped Viruses Using Sapphyrin, α 22 π–Electron "Expanded Porphyrin": Possible Approaches to Prophylactic Blood Purification Protocols,"*SPIE Photodynamic Therapy: Mechanisms II*. 1203:233–245, 1990.

Maiya et al., "Ground–and Excited–State Spectral and Redox Properties of Cadmium(II) Texaphyrin," *Journal of Physical Chemistry*, 93(24):8111–8115, 1989.

Leff, "Texas 'Son–of–Porphyrin' Molecule Lassos Europium to Kill Drug Resistance Gene," *BioWorld Today*, 5(156):1, 1994.

Young et al., "Preclinical Evaluation of Gadolinium (III) Texaphyrin Complex. A New Paramagnetic Contrast Agent for Magnetic Resonance Imaging," *Investigative Radiology*, 29(3):330–338, 1994.

n = 1 - 7

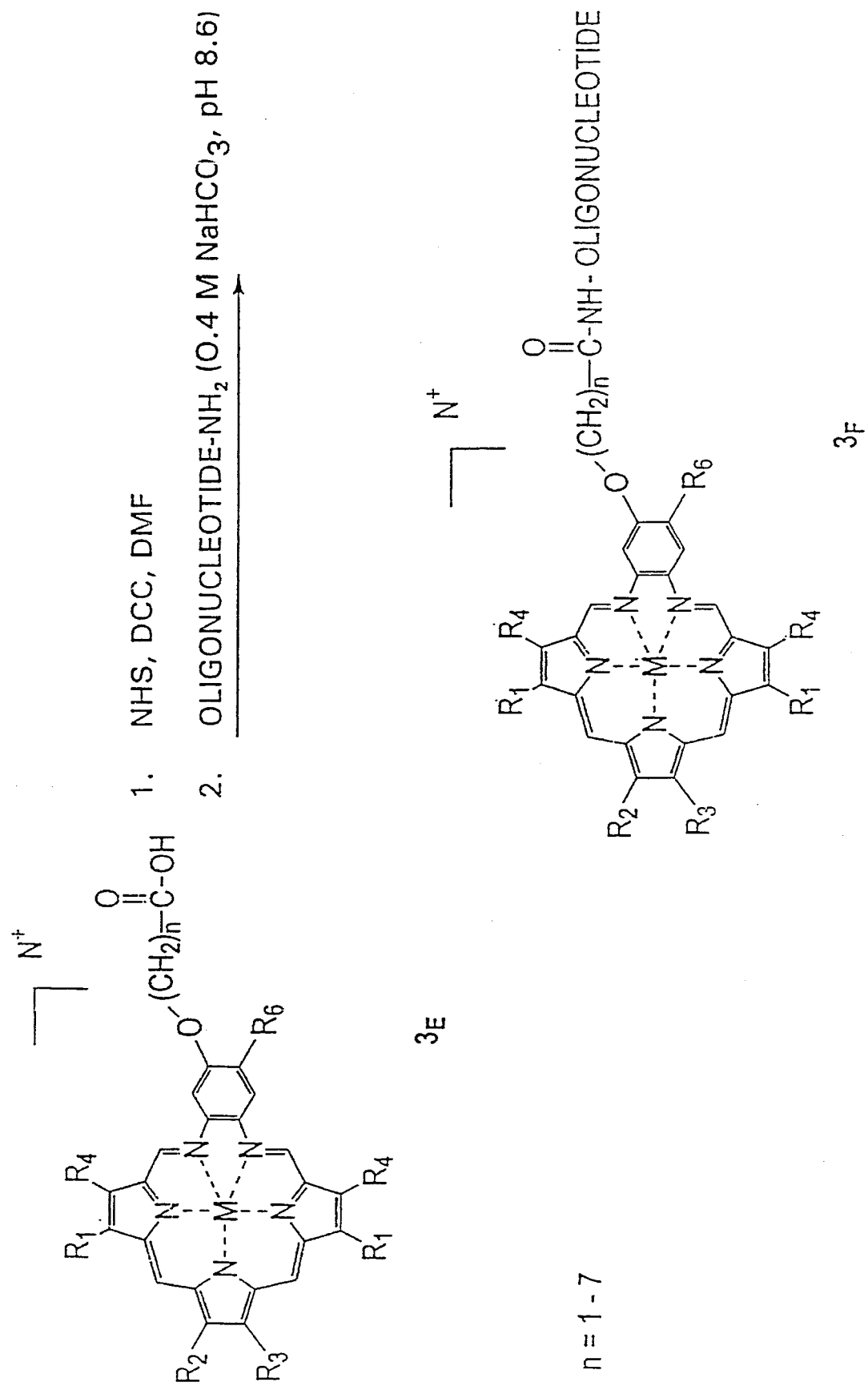

5A  $R_5 = R_6 = OCH_2CH_2CH_2OH$

5B  $R_5 = OCH_2COOH$, $R_6 = H$

5C  $R_5 = OCH_2CO\text{-}DNA$, $R_6 = H$

11A Seq. ID. NO. 4
11B Seq. ID. NO. 5

```
                                MeMeMe  MeMeMeMeMeMe  MeMeMe
                                |||   |  ||||||  |||
                                ooo  oo  oooooo  ooo
                            o  o  o  o  o  o  o  o  o
                            |  |  |  |  |  |  |  |  |
5'- LuTxHN-(CH₂)₆-PO₄-CAU CUG UGA GCC GGG-3'
3'-A AAT AAA ACC TCT GAA GTA GAC ACT CGG CCC ACA AC -5'
```

11C Seq. ID. NO. 6
11D (8B) Seq. ID. NO. 3

```
                                MeMeMe  MeMeMeMeMeMe  MeMeMe
                                |||   |  ||||||  |||
                                ooo  oo  oooooo  ooo
                            o  o  o  o  o  o  o  o  o
                            |  |  |  |  |  |  |  |  |
5'- LuTxHN-(CH₂)₆-PO₄-CUC GGC CAU AGC GAA-3'
3'-A GGT ACC ACT GTA GAA GAG CCG GTA TCG CTT ACA AG -5'
```

FIG. 8

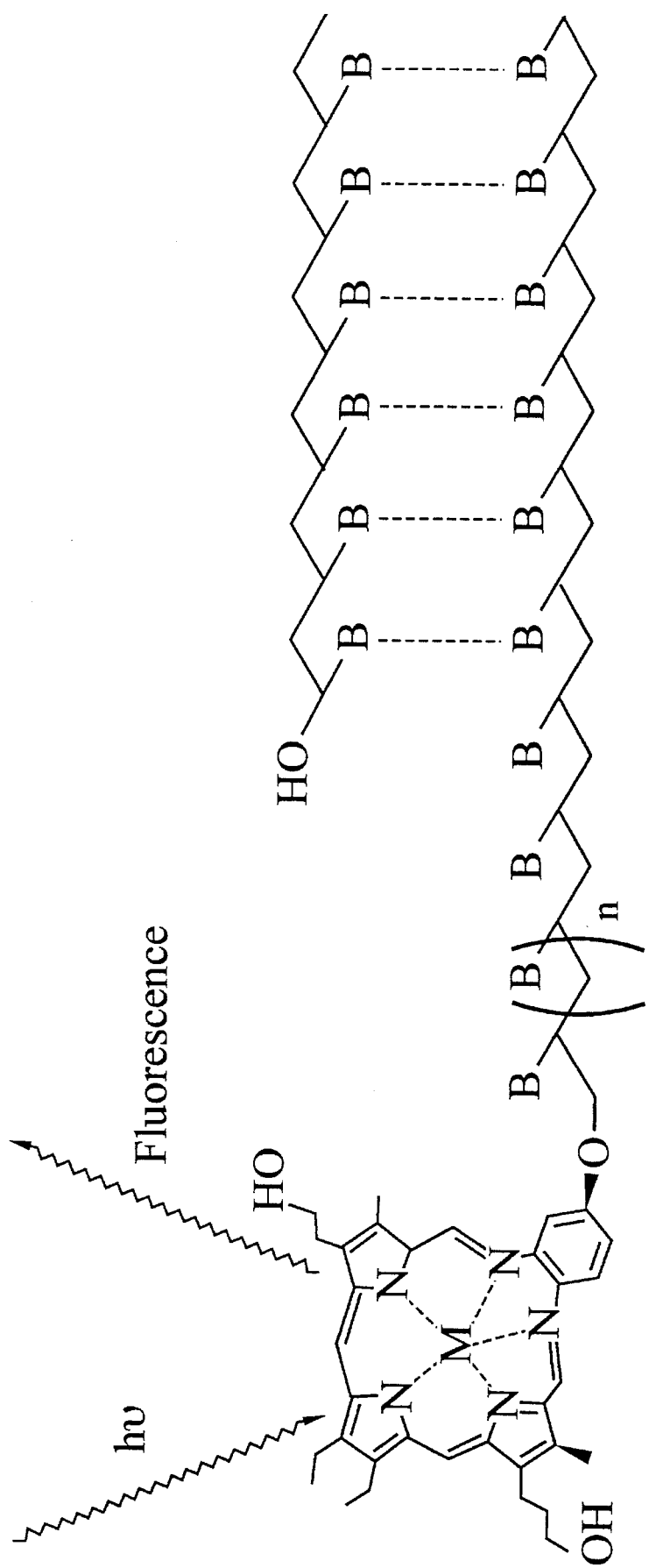
FIG. 9B1

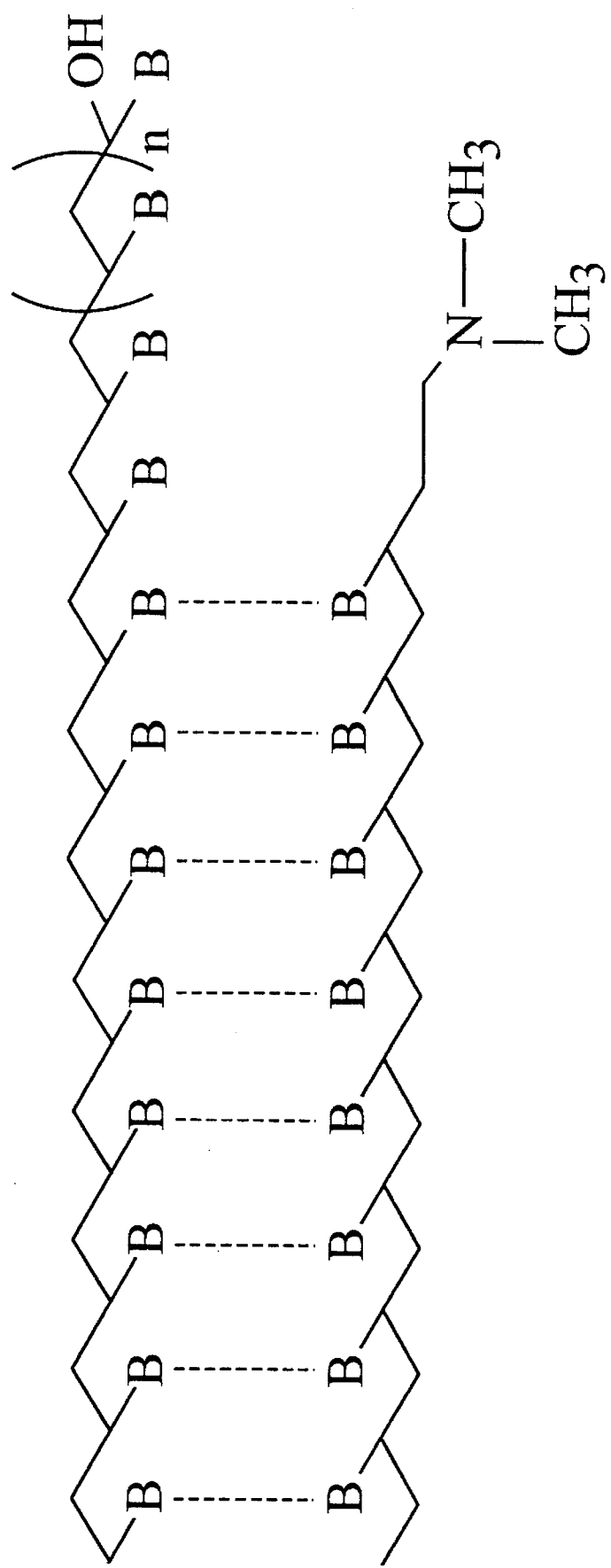
FIG. 9B2

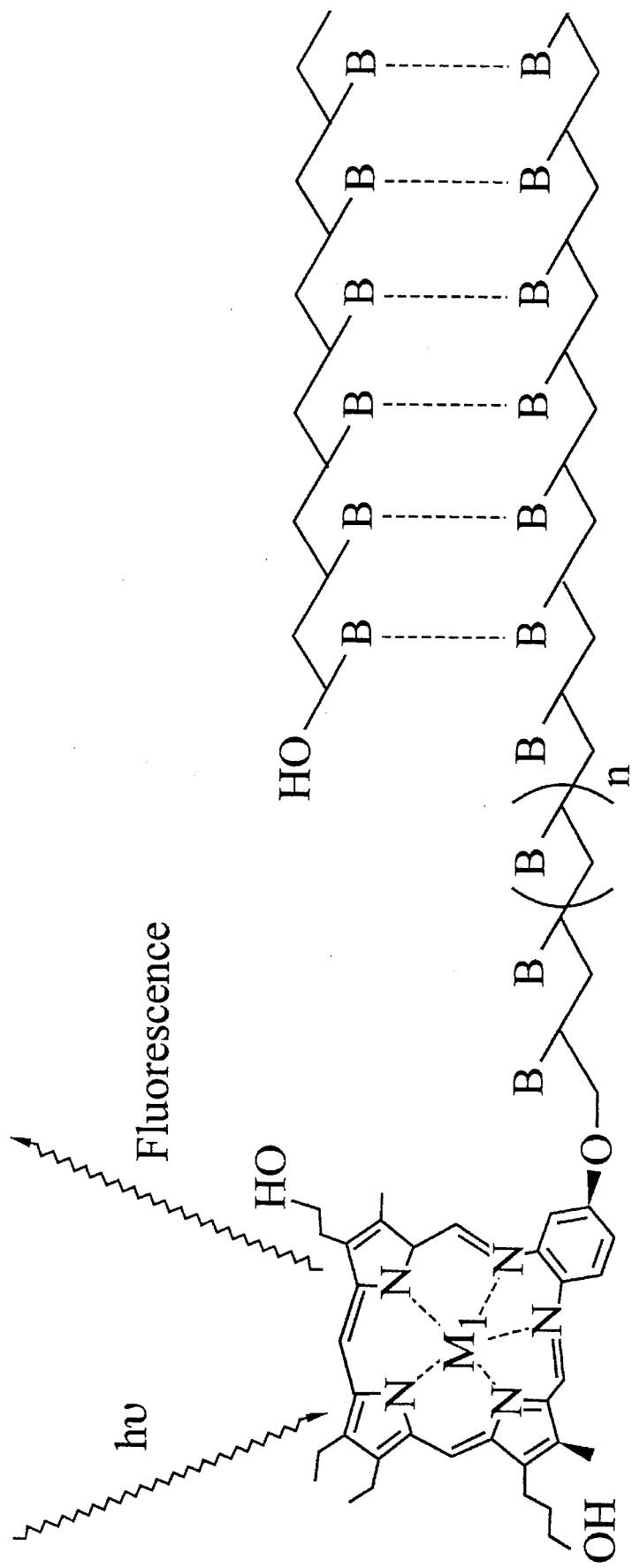
FIG. 10B1

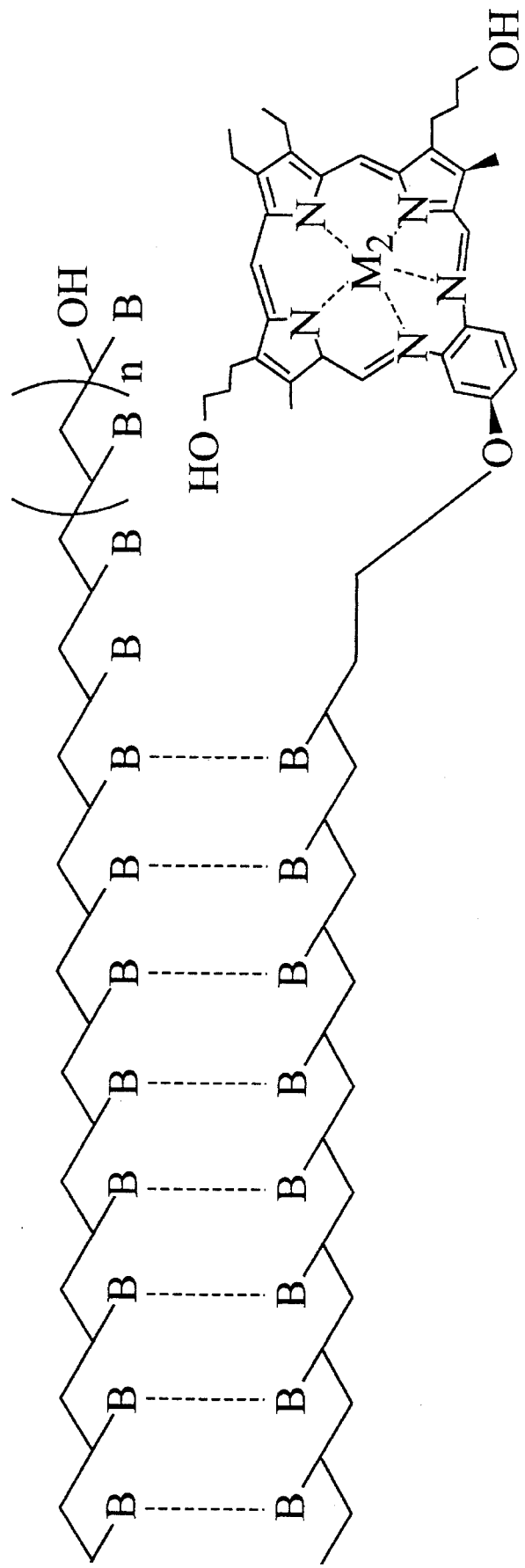
FIG. 10B2

TEXAPHYRINS AND USES THEREOF

Research leading to the present invention was supported in part by the National Science Foundation (CHE 9122161) and the National Institutes of Health (AI 33577 and AI 28845). The U.S. government therefore has certain rights in the invention.

This application is a continuation-in-part application of U.S. Ser. No. 08/112,872, filed Aug. 25, 1993, now U.S. Pat. No. 5,451,576, and PCT/US94/06284 filed Jun. 9, 1994. U.S. Ser. No. 08/112,872, is a divisional application of U.S. Ser. No. 07/822,964, filed Jan. 21, 1992, since issued as U.S. Pat. No. 5,252,720, Oct. 12, 1993. PCT/US94/06284 is a continuation-in-part application of U.S. Ser. No. 08/227,370, filed Apr. 14, 1994. U.S. Ser. No. 08/227,370, is a continuation-in-part application of U.S. Ser. No. 08/075,123, filed Jun. 9, 1993, now abandoned. U.S. Ser. No. 08/075,123, was a continuation-in-part of U.S. Ser. No. 07/822,964, filed Jan. 21, 1992, since issued as U.S. Pat. No. 5,252,720, Oct. 12, 1993. U.S. Ser. No. 07/822,964, was a continuation-in-part application of No. 07/771,393, filed Sep. 30, 1991, now abandoned, which was a continuation-in-part of No. 07/539,975, filed Jun. 18, 1990, since issued as U.S. Pat. No. 5,162,509, on Nov. 10, 1992, and a continuation of international application No. PCT/US90/01208, filed Mar. 6, 1990. U.S. Ser. No. 07/539,975, was a divisional application of U.S. Ser. No. 07/320,293, filed Mar. 6, 1989, since issued as U.S. Pat. No. 4,935,498, Jun. 19, 1990. All of the above-named patents are incorporated by reference herein.

BACKGROUND OF THE INVENTION

Photodynamic therapy (PDT) is a treatment technique that uses a photosensitizing dye, which localizes at, or near, the treatment site, and when irradiated in the presence of oxygen serves to produce cytotoxic materials, such as singlet oxygen ($O_2(^1\Delta_g)$) from benign precursors (e.g. $O_2(^3\Sigma_g^-)$) Other reactive species such as superoxide, hydroperoxyl, or hydroxyl radicals may be involved. At the doses used, neither the light nor the drug has any independent biological effect. In PDT, the photosensitizer acts in a 'catalytic' way, since its function is not to react directly with the cellular targets, but to absorb light energy and to transfer it to molecular oxygen, regenerating ground state photosensitizer.

The effectiveness of PDT is due to three additional factors: i) The photosensitive dyes used in PDT must have the ability to localize at the treatment site relative to surrounding tissue. ii) The high reactivity and short lifetime of activated oxygen means that it has a very short range and is unlikely to escape from the cell in which it is produced; cytotoxicity is therefore restricted to the precise region of tissue absorbing light, perhaps down to the cellular level. iii) Developments in lasers and fiber optics allow a beam of intense light to be delivered precisely to many parts of the body.

For reviews of photodynamic therapy, see U.S. Pat. No. 5,252,720 (incorporated by reference herein); Sindelar et al., (1991); Grossweiner, L. I., (1991); Henderson, B. W. and T. J. Dougherty, (1992); and Moan, J. and K. Berg, (1992). In recent years, considerable effort has been devoted to the synthesis and study of new photosensitizers (a review is found in Brown, S. B. and Truscott, T. G., 1993). The development of more effective photochemotherapeutic agents requires the synthesis of compounds which absorb in the spectral region where living tissues are relatively transparent (i.e., 700–1000 nm), have high triplet quantum yields, and are minimally toxic. The present inventors' texaphyrin molecules absorb strongly in the tissue-transparent 730–770 nm range. The photophysical properties of metallotexaphyrins parallel those of the corresponding metalloporphyrins and the diamagnetic complexes sensitize the production of $^1O_2$ in high quantum yield The texaphyrins of the present invention, being completely synthetic, can be tuned so as to incorporate desired properties.

The present invention also relates to catalysts for the cleavage of DNA, in particular, photo-induced site-specific cleavage of DNA in a biological system. An effective photocatalyst for PDT and DNA cleavage would have the following properties:

1. Easily available
2. Low intrinsic toxicity
3. Long wavelength absorption
4. Efficient photosensitizer for singlet oxygen production
5. Fair solubility in water
6. Selective uptake in lipophilic tissue such as atheroma or tumor tissue
7. Showing high affinity for enveloped viruses
8. Quick degradation and/or elimination after use
9. Chemically pure and stable
10. Easily subject to synthetic modification
11. Efficient at physiological temperature and pH
12. Specific for certain biological substrates
13. Easy administered to a biological system The ability to specifically photo-cleave DNA has important implications for the treatment of various diseases; for destruction of viral DNA; for construction of probes for controlling gene expression at the cellular level and for diagnosis; for footprinting analyses, DNA sequencing, chromosome analyses, gene isolation, recombinant DNA manipulations, and for mapping of large genomes and chromosomes; in chemotherapy; and in site-directed mutagenesis. Potential particular applications for this process further include the subsequent recombination of DNA.

Photodynamic cleavage of DNA is known. For example, Praseuth et al., reported cleavage of plasmid DNA by synthetic water-soluble porphyrins with visible light in the presence of oxygen. Fiel, R. J. (1989) also reported the photosensitized strand cleavage and oxidative-reductive strand scission of DNA by iron porphyrins. In another example, Kobayashi et al. reported cleavage of plasmid DNA by sodium pheophorbide (a derivative of chlorophyll) with visible light in the presence of oxygen. Porphyrin-oligonucleotide derivatives were reportedly used to effect sequence specific modifications of DNA substrates followed by cleavage using hot piperidine (Vlassov et al., 1991; Le Doan et al., 1990). The absorption wavelengths for these porphyrin conjugates were below 700 nm, a range that does not penetrate tissue as effectively as longer wavelengths of light.

The use of ultraviolet light with the drug 8-methoxypsoralen to treat psoriasis is well established. Lee et al. relates to the interaction of psoralen-derivatized oligodeoxyribonucleoside methylphosphonates with single-stranded DNA. Crosslinked photoadducts between pyrimidines and psoralen appear to form. This treatment may result in the development of cancerous cells. Furthermore, irradiation at the short wavelength of about 365 nm does not penetrate the body and is therefore only useful on the body surface. Psoralen-based treatments must allow the drug to leave the body before the patient is exposed to visible light or the reaction will continue on the skin surface.

Sequence specific cleavage of DNA has also been reported for dark reactions using oligonucleotides derivatized with metal complexes. Some examples include oligonucleotide-EDTA-Fe complexes (Strobel, D. A. and P. B. Dervan, 1989; Lin, et al., 1989; Dreyer, G. B. and P. B. Dervan, 1985), oligonucleotide-tricationic porphyrins with metal binding appendages (Groves, J. T. and T. P. Farrell, 1989), oligonucleotide-phenanthroline-copper complexes (Chen, C. H. B. and D. S. Sigman, 1988), oligonucleotide-manganese-porphyrins (Meunier, B. et al., 1993), and iron-porphyrins linked to oligonucleotides (Le Doan et al., 1986, 1987).

Limitations of current photosensitive molecules include lack of good tumor selectivity, and the short wavelength of light required to effect the photoexcitation that is prerequisite to photosensitization. Therefore, characteristics sought in new photosensitizers are the retention or enhancement of tumor localization and absorption in the longer wavelength ranges up to about 800 nm as well as non-toxicity, lack of skin photosensitivity, and ease of production in a pure form.

| LIST OF ABBREVIATIONS | |
|---|---|
| DCA: | Dichloroacetic acid |
| DCC: | Dicyclohexylcarbodiimide |
| DMAP: | Dimethylaminopyridine |
| DMF: | Dimethylformamide |
| DMT: | Dimethoxytrityl protecting group |
| DMT-Cl: | Dimethoxytrityl chloride |
| EDC: | L-Ethyl-3-[3-(dimethylamino)propyl] carbodiimide |
| EDTA: | Ethylenediamine tetraacetic acid |
| IPA: | Isopropylalcohol |
| NHS: | N-hydroxysuccinimide |
| NM: | Nanometers |
| pTSA: | p-Toluenesulfonic acid monohydrate |
| TEA: | Triethylamine |
| TEAB: | Triethylammonium bicarbonate |
| TFA: | Trifluoroacetic acid |
| TsCl: | Tosyl chloride |
| THF: | Tetrahydrofuran |
| Txp(txph)(TX): | Texaphyrin |

SUMMARY OF THE INVENTION

The present invention seeks to solve these problems by providing photosensitive texaphyrins and oligonucleotide conjugates thereof that provide localization to tumors, atheroma, or are site-directing; have absorption in the physiologically important range of 700–900 nm; provide stable chelation for an otherwise toxic metallic cation; provide specificity for targeted sites in a therapeutic application; and are sufficiently nontoxic for in vivo use.

The present invention also involves the discovery that photosensitive texaphyrins catalyze the cleavage of a polymer of deoxyribonucleic acid. Cleavage is enhanced by the presence of oxygen, indicating that singlet oxygen or another oxygen byproduct is the likely toxic agent. A photosensitive texaphyrin may be a diamagnetic metal texaphyrin complex or may be metal-free. Texaphyrins are unique molecules in that they chelate a metal in a very stable complex and, furthermore, allow for derivatization for various biological applications.

U.S. Pat. No. 5,252,720, incorporated herein by reference, provided data that demonstrated the stability and utility of texaphyrin metal complexes for in vivo use in magnetic resonance imaging protocols. The Y(III), Gd(III), and In(III) complexes of texaphyrin were found to be hydrolytically stable in 1:1 methanol-water mixtures with half-lives for decomplexation and/or ligand decomposition exceeding 3 weeks in both cases. The Gd(III) complex of a tetrahydroxylated texaphyrin derivative ("GdT2B2") showed low toxicity and good tissue selectivity in magnetic resonance imaging enhancement. The related texaphyrin diamagnetic metal complex-conjugates of the present invention are expected to have similar stability for chelating diamagnetic metal cations and similar low toxicity for in vivo applications.

Texaphyrin metal complexes possess inherent biolocalization specificity as described in the '720 patent, localizing in lipid rich regions such as, for example, liver, kidney, tumor and atheroma. In one embodiment of the present invention, the texaphyrin metal complexes are further coupled to site-directing molecules to form conjugates for targeted in vivo delivery. "Specificity for targeted sites" means that upon contacting the texaphyrin metal complex-conjugate with the targeted site, for example, under physiological conditions of ionic strength, temperature, pH and the like, specific binding will occur. The interaction may occur due to specific electrostatic, hydrophobic, entropic or other interaction of certain residues of the conjugate with specific residues of the target to form a stable complex under conditions effective to promote the interaction. In a preferred embodiment of the present invention, the interaction between a texaphyrin-oligonucleotide conjugate and the complementary oligonucleotide is an example of antisense technology and will allow cleavage of a polymer of deoxyribonucleic acid that is in the vicinity of the specific binding. The inherent biolocalization properties of texaphyrin further effect targeting of an antisense agent to lipophilic regions, especially tumors and atheroma, for example.

Exemplary site-directing molecules contemplated in the present invention include but are not limited to: polydeoxyribonucleotides, oligodeoxyribonucleotides, polyribonucleotide analogs, oligoribonucleotide analogs; polyamides including peptides having affinity for a biological receptor and proteins such as antibodies; steroids and steroid derivatives; hormones such as estradiol, or histamine; hormone mimics such as morphine; and further macrocycles such as sapphyrins and rubyrins. The oligonucleotides may be derivatized at the bases, the sugars, the ends of the chains, or at the phosphate groups of the backbone to promote in vivo stability. Modifications of the phosphate groups are preferred in one embodiment of the invention since phosphate linkages are sensitive to nuclease activity. Preferred derivatives are the methylphosphonates, phosphotriesters, phosphorothioates, and phosphoramidates. Additionally, the phosphate linkages may be completely substituted with non-phosphate linkages such as amide linkages. Appendages to the ends of the oligonucleotide chains also provide exonuclease resistance. Sugar modifications may include alkyl groups attached to an oxygen of a ribose moiety in a ribonucleotide. In particular, the alkyl group is preferably a methyl group and the methyl group is attached to the 2' oxygen of the ribose. Other alkyl groups may be ethyl or propyl.

It is understood that the terms "nucleotide", "polynucleotide" and "oligonucleotide", as used herein and in the appended claims, refer to both naturally-occurring and synthetic nucleotides, poly- and oligonucleotides and to analogs and derivatives thereof such as methylphosphonates, phosphotriesters, phosphorothioates and phosphoramidates and the like. Deoxyribonucleotides and ribonucleotide analogs are contemplated as site-directing molecules in the present invention.

The term "texaphyrin-oligonucleotide conjugate" means that an oligonucleotide is attached to the texaphyrin in a 5' or 3' linkage or both types of linkages to allow the texaphyrin to be an internal residue in the conjugate. The oligonucleotide or other site-directing molecule may be attached either directly to the texaphyrin via a linker, or a couple of variable length. During catalysis, for example, the texaphyrin portion of a texaphyrin metal complex-oligonucleotide conjugate is placed in the vicinity of the substrate upon binding of the oligonucleotide to the targeted nucleic acid substrate. A "sapphyrin-oligonucleotide conjugate" is referred to in the same way as described above for a texaphyrin-oligonucleotide conjugate except that the texaphyrin is replaced with a sapphyrin.

A couple may be described as a linker, i.e., the covalent product formed by reaction of a reactive group designed to attach covalently another molecule at a distance from the texaphyrin macrocycle. Exemplary linkers or couples are amides, amine, thioether, ether, or phosphate covalent bonds as described in the examples for attachment of oligonucleotides. In most preferred embodiments, oligonucleotides and other site-directing molecules are covalently bonded to the texaphyrin via a carbon-nitrogen, carbon-sulfur, or a carbon-oxygen bond.

The cleavage of DNA described herein is a photolytic cleavage. It is believed that the cleavage is not hydrolytic where a water molecule is added across a bond to break the bond, nor is the cleavage believed to be solely oxidative where an oxidation reaction in the absence of light causes breakage of the bond.

It will be apparent to one of skill in the art in light of the present disclosure that the site-specific cleavage of DNA has important ramifications in a variety of applications. Potential particular applications for this process include antisense applications; the specific cleavage and possible subsequent recombination of DNA; destruction of viral DNA; construction of probes for controlling gene expression at the cellular level and for diagnosis; and cleavage of DNA in footprinting analyses, DNA sequencing, chromosome analyses, gene isolation, recombinant DNA manipulations, mapping of large genomes and chromosomes, in chemotherapy and in site-directing mutagenesis.

An embodiment of the present invention is a preferred texaphyrin having the structure:

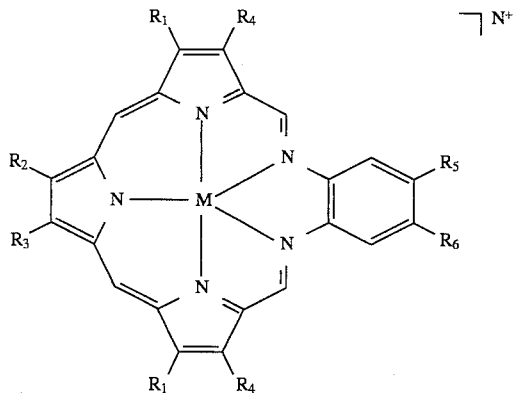

where M is H, a divalent metal cation selected from the group consisting of Ca(II), Mn(II), Co(II), Ni(II), Zn(II), Cd(II), Hg(II), Fe(II), Sm(II) and UO(II) or a trivalent metal cation selected from the group consisting of Mn(III), Co(III), Ni(III), Fe(III), Ho(III), Ce(III), Y(III), In(III), Pr(III), Nd(III), Sm(III), Eu(III), Gd(III), Tb(III), Dy(III), Er(III), Tm(III), Yb(III), Lu(III), La(III), and U(III). Preferred metals include Lu(III), Dy(III), Eu(III), or Gd(III).

The nonmetallated form of texaphyrin may be used, in particular, where fluorescence is the preferred means of detection of the texaphyrin. M may be H or $CH_3$ in a nonmetallated form of texaphyrin. A texaphrin having a methyl group attached to a ring nitrogen (M is $CH_3$) is described in related copending application U.S. Ser. No. 08/135,118, incorporated by reference herein. In the above texaphyrin, $R_1$ is $(CH_2)_2CH_2OH$, $R_2$ and $R_3$ are $CH_2CH_3$, $R_4$ is $CH_3$, $R_5$ and $R_6$ are $O(CH_2CH_2O)_2CH_2CH_2OCH_3$ and N is an integer less than or equal to 2.

A method of treating a host harboring atheroma or benign or malignant tumor cells is an aspect of the present invention. The method comprises the steps of: i) administering to the host an effective amount of a photosensitive texaphyrin, and ii) photoirradiating the photosensitive texaphyrin in proximity to the atheroma or tumor cells. The term "photosensitive" means that upon irradiation, texaphyrin effects either the generation of oxygen products that are cytotoxic or means that the texaphyrin is fluorescent, or both. Cytotoxic oxygen products may be singlet oxygen, hydroxyl radicals, superoxide, or hydroperoxyl radicals. The texaphyrin may be a diamagnetic metal complex or a metal-free species. Diamagnetic metals would include preferably, Lu(III), La(III), In(III), Zn(II) or Cd(II). Most preferably, the diamagnetic metal is Lu(III).

The above-described method may further comprise the step of determining localization sites of the photosensitive texaphyrin in the host by reference to the texaphyrin. "By reference to the texaphyrin" as used herein means that the location may be found by localization such as magnetic resonance imaging if the texaphyrin contains a metal that is paramagnetic, gamma ray detection if the metal is gamma emitting, or by using monochromatic X-ray photon sources or fluorescent spectroscopy. Gamma emitting metals for radioimmunodiagnostics are described in U.S. Pat. No. 5,252,720, incorporated by reference herein. A preferred gamma emitting metal is [111]In(III). In the case of a texaphyrin that is non-metallated, fluorescence imaging is the preferred means of detection.

"Selective biolocalization" means having an inherently greater affinity for certain tissues relative to surrounding tissues. Texaphyrins have biolocalization specificity for lipid rich tissue, such as atheroma and tumor, for example. Importantly, hydroxylated texaphyrins have a lipid-water distribution coefficient that is optimal for localization to lipophilic regions, yet sufficiently water soluble to allow ease of handling.

The abovenamed method may further include a step of administering to the host a photosensitive texaphyrin diamagnetic metal complex. Preferably, the complex has essentially identical biolocalization property to the texaphyrin administered in step (i).

These steps may be combined in a method of treating a host harboring atheroma or benign or malignant tumor cells. The method comprises the administration to the host as a first agent, a detectable texaphyrin; determining localization sites in the host by reference to such detectable texaphyrin; followed by administration to the host as a second agent, a texaphyrin-diamagnetic metal complex exhibiting the ability to generate singlet oxygen upon exposure to light; and photoirradiating the second agent in proximity to said atheroma or tumor cells. Preferably, the first and second agents are water soluble while retaining lipophilicity and exhibit selective biolocalization in such atheroma or tumor cells relative to surrounding tissue. A further preferred embodiment is where the host is harboring atheroma.

The first agent is further defined in a preferred embodiment as being a texaphyrin-paramagnetic metal complex, said paramagnetic metal serving as a detectable metal. In this case, determination of localization sites occurs by magnetic resonance imaging. The paramagnetic metal is most preferably Gd(III).

In another embodiment of this method, the first agent is a photosensitive texaphyrin that exhibits fluorescence. This may be a non-metallated texaphyrin or a texaphyrin-metal complex that exhibits fluorescence. Determination of localization sites occurs by said fluorescence of the photosensitive texaphyrin. In some instances, the first and second agents may be the same photosensitive agent. In this case, the step of administering the second agent following determination of localization sites may be eliminated. In a preferred embodiment, the first agent is a non-metallated texaphyrin and the second agent is a texaphyrin-diamagnetic metal complex. In another preferred embodiment, both the first agent and the second agent are texaphyrin-diamagnetic metal complexes, and more preferably they are the same complex. The diamagnetic metal is preferably Lu(III).

A further variation of this method uses as a first agent a gamma-emitting radioisotope-texaphyrin complex, said gamma-emitting radioisotope serving as a detectable metal. Determination of localization sites occurs by gamma body scanning.

"Essentially identical biolocalization property" means the second agent is a texaphyrin derivative having about the same selective targeting characteristics in tissue as demonstrated by the first agent.

In one embodiment of the above-described method, the complex of the first agent and the complex of the second agent independently have the structure:

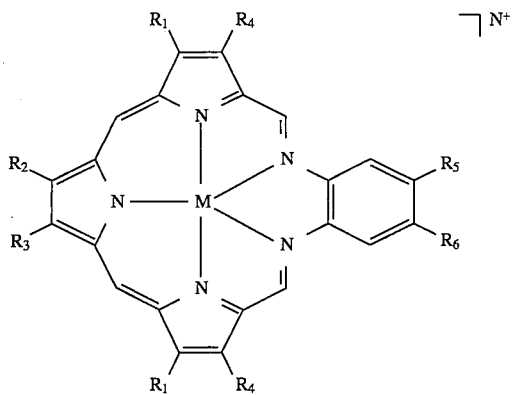

wherein M is H or a detectable metal cation in the first agent and a diamagnetic metal cation in the second agent; $R_1$, $R_2$, $R_3$, $R_4$, $R_5$ and $R_6$ are independently hydrogen, hydroxyl, alkyl, hydroxyalkyl, alkoxy, hydroxyalkoxy, saccharide, carboxyalkyl, carboxyamidealkyl, a site-directing molecule, or a couple to a site-directing molecule where at least one of $R_1$, $R_2$, $R_3$, $R_4$, $R_5$ and $R_6$ is hydroxyl, hydroxyalkoxy, saccharide, alkoxy, carboxyalkyl, carboxyamidealkyl, hydroxyalkyl, a site-directing molecule or a couple to a site-directing molecule; and N is an integer less than or equal to 2. The photoirradiating is preferably at wavelengths where biological tissue is relatively transparent, ie. the 700–900 nm range and where laser excitation is possible. A preferred range of wavelength of light is 700–770

In the detection and treatment of atheroma or benign or malignant tumor cells, a preferred paramagnetic metal complex is the Gd(III) complex of 4,5-diethyl-10,23-dimethyl-9,24-bis(3-hydroxypropyl)- 16,17-bis[2-[2-(2-methoxyethoxy)ethoxy]ethoxy]- 13,20,25,26,27-pentaazapentacyclo[20.2.1.1$^{3,6}$.1$^{8,11}$.0$^{14,19}$] heptacosa-1,3,5,7,9,11 (27),12, 14(19),15,17,20,22(25),23-tridecaene ("GdT2BET") and a preferred diamagnetic metal complex is the Lu(III) complex of 4,5-diethyl-10,23-dimethyl-9,24-bis(3-hydroxypropyl)-16,17-bis[2-[2-(2-methoxyethoxy)ethoxy]ethoxy]- 13,20, 25,26,27-pentaazapentacyclo[20.2.1.1$^{3,6}$.1$^{8,11}$.0$^{14,19}$] heptacosa-1,3,5,7,9,11(27),12,14(19),15,17,20,22(25),23-tridecaene ("LuT2BET").

A preferred method of treating a host harboring tumor cells or atheroma comprises the steps of administering to the host an effective amount of a texaphyrin-diamagnetic metal complex, the complex exhibiting selective biolocalization in the tumor cells or atheroma relative to surrounding tissue; and photoirradiating the texaphyrin-diamagnetic metal complex in proximity to the tumor cells or atheroma. The photoirradiating is carried out preferably at about 700–900 nm, and more preferably at 700–770 nm.

A further embodiment of the present invention is a method of detecting the presence of a photosensitive texaphyrin in solution or in tissue comprising the steps of i) irradiating a solution or tissue in which presence of a photosensitive texaphyrin is suspected; and ii) monitoring fluorescence emitted from the irradiated solution or tissue wherein fluorescence indicates the presence of a photosensitive texaphyrin. The irradiating is carried out using light of a wavelength range of about 700–800 nm while monitoring the emitted fluorescence at wavelengths that are about 5–40 nm further to the red (i.e. longer wavelengths). For example, in aqueous solution, the fluorescence of LuT2BET is monitored 14 nm to the red of the irradiation wavelength.

In the above method of treating a host harboring atheroma or benign or malignant tumor cells, the localization sites of the texaphyrin may be determined by fluorescence. In this case, the texaphyrin may be metallated, provided the metal is diamagnetic, or may be metal-free.

A further embodiment of the present invention provides a method of light-induced cleavage of a polymer of deoxyribonucleic acid. The method comprises the steps of contacting the polymer with a photosensitive texaphyrin and exposing the photosensitive texaphyrin to light for a time sufficient to cleave the polymer. In a preferred embodiment, the exposing step is carried out in the presence of oxygen. A texaphyrin as used herein is an aromatic pentadentate expanded porphyrin analog with appended functional groups. Such pendant groups may enhance solubility or biolocalization or may provide coupling sites for site-directing molecules such as oligonucleotides. The texaphyrin may be a metal complex of texaphyrin, preferred metals are diamagnetic metals.

The polymer may be a solution or a suspension of DNA or may be cellular DNA in vitro or in vivo. DNA is preferably cleaved over RNA. However, treatment of RNA with 1 μM LuB2T2 results in hydrolysis products both in the presence and in the absence of light. This reaction with RNA, therefore, is not photoinduced and produces different products than the photocleavage reaction of the present invention. In the present light-dependent cleavage, the light may have a wavelength range of about 650–900 nm, preferably 700–800 nm, and most preferably 730–770 nm.

The texaphyrin metal complex for use in light-induced cleavage of a polymer of deoxyribonucleic acid may have the structure:

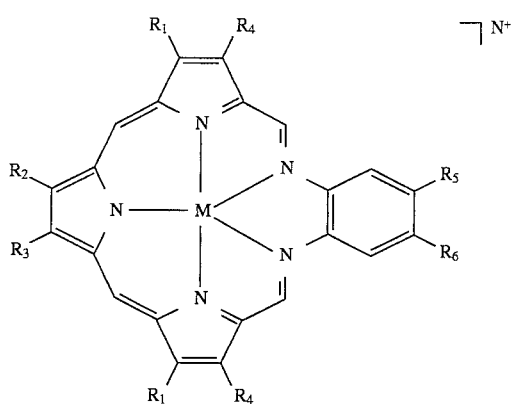

In this texaphyrin, M is H or a diamagnetic metal cation. $R_1$, $R_2$, $R_3$, $R_4$, $R_5$ and $R_6$ are independently hydrogen, hydroxyl, alkyl, hydroxyalkyl, alkoxy, hydroxyalkoxy, saccharide, carboxyalkyl, carboxyamidealkyl, a site-directing molecule or a couple to a site-directing molecule. A site-directing molecule is the conjugate of a texaphyrin metal complex-conjugate. A preferred diamagnetic metal cation is Lu(III), La(III), In(III), Zn(II) or Cd(II). A most preferred diamagnetic metal cation is Lu(III).

N will typically be an integer less than or equal to 2. In the context of the basic macrocycle with a divalent or trivalent metal cation, N is 1 or 2; however, one skilled in the art in light of the present disclosure would realize that the value of N would be altered due to charges present on substituents $R_1$–$R_6$ and charges present on the covalently bound site-directing molecule, for example, charges of the phosphate groups on an oligonucleotide.

$R_1$, $R_2$, $R_3$, $R_4$, $R_5$ and $R_6$ may also independently be amino, carboxy, carboxamide, ester, amide sulfonato, aminoalkyl, sulfonatoalkyl, amidealkyl, aryl, etheramide or equivalent structures conferring the desired properties. In a preferred embodiment, at least one of $R_1$, $R_2$, $R_3$, $R_4$, $R_5$ and $R_6$ is a site-directing molecule or is a couple to a site-directing molecule. For bulky R groups on the benzene ring portion of the molecule such as oligonucleotides, one skilled in the art would realize that derivatization at one position on the benzene portion is more preferred.

Hydroxyalkyl means alkyl groups having hydroxyl groups attached. Alkoxy means alkyl groups attached to an oxygen. Hydroxyalkoxy means alkyl groups having ether or ester linkages, hydroxyl groups, substituted hydroxyl groups, carboxyl groups, substituted carboxyl groups or the like. Saccharide includes oxidized, reduced or substituted saccharide; hexoses such as D-glucose, D-mannose or D-galactose; pentoses such as D-ribose or D-arabinose; ketoses such as D-ribulose or D-fructose; disaccharides such as sucrose, lactose, or maltose; derivatives such as acetals, amines, and phosphorylated sugars; oligosacchrides, as well as open chain forms of various sugars, and the like. Examples of amine-derivatized sugars are galactosamine, glucosamine, and sialic acid. Carboxyamidealkyl means alkyl groups with secondary or tertiary amide linkages or the like. Carboxyalkyl means alkyl groups having hydroxyl groups, carboxyl or amide substituted ethers, ester linkages, tertiary amide linkages removed from the ether or the like.

For the above-described texaphyrins, hydroxyalkoxy may be alkyl having independently hydroxy substituents and ether branches or may be $C_{(n-x)}H_{((2n+1)-2x)}O_xO_y$ or $OC_{(n-x)}H_{((2n+1)-2x)}O_xO_y$ where n is a positive integer from 1 to 10, x is zero or a positive integer less than or equal to n, and y is zero or a positive integer less than or equal to $((2n+1)-2x)$. The hydroxyalkoxy or saccharide may be $C_nH_{((2n+1)-q)}O_yR^a_q$, $OC_nH_{((2n+1)-q)}O_yR^a_q$ or $(CH_2)_nCO_2R^a$ where n is a positive integer from 1 to 10, y is zero or a positive integer less than $((2n+1)-q)$, q is zero or a positive integer less than or equal to 2n+1, and $R^a$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$. In this case, m is a positive integer from 1 to 10, w is zero or a positive integer less than or equal to m, z is zero or a positive integer less than or equal to $((2m+1)-2w)$, and R is H, alkyl, hydroxyalkyl, or $C_mH_{((2m+1)-r)}O_zR^b_r$ where m is a positive integer from 1 to 10, z is zero or a positive integer less than $((2m+1)-r)$, r is zero or a positive integer less than or equal to 2m+1, and $R^b$ is independently H, alkyl, hydroxyalkyl, or saccharide.

Carboxyamidealkyl may be alkyl having secondary or tertiary amide linkages or $(CH_2)_nCONHR^a$, $O(CH_2)_nCONHR^a$, $(CH_2)_nCON(R^a)_2$, or $O(CH_2)_nCON(R^a)_2$ where n is a positive integer from 1 to 10, and $R^a$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$, $N(R)OCC_{(m-w)}H_{((2m+1)-2w)}O_wO_z$, or a site-directing molecule. In this case, m is a positive integer from 1 to 10, w is zero or a positive integer less than or equal to m, z is zero or a positive integer less than or equal to $((2m+1)-2w)$, and R is H, alkyl, hydroxyalkyl, or $C_mH_{((2m+1)-r)}O_zR^b_r$. In this case, m is a positive integer from 1 to 10, z is zero or a positive integer less than $((2m+1)-r)$, r is zero or a positive integer less than or equal to 2m+1, and $R^b$ is independently H, alkyl, hydroxyalkyl, or saccharide. In a preferred embodiment, $R^a$ is an oligonucleotide.

Carboxyalkyl may be alkyl having a carboxyl substituted ether, an amide substituted ether or a tertiary amide removed from an ether or $C_nH_{((2n+1)-q)}O_yR^c_q$ or $OC_nH_{((2n+1)-q)}O_yR^c_q$ where n is a positive integer from 1 to 10; y is zero or a positive integer less than $((2n+1)-q)$, q is zero or a positive integer less than or equal to 2n+1, and $R^c$ is $(CH_2)_nCO_2R^d$, $(CH_2)_nCONHR^d$, $(CH_2)_nCON(R^d)_2$ or a site-directing molecule. In this case, n is a positive integer from 1 to 10, $R^d$ is independently H, alkyl, hydroxyalkyl, saccharide, $C_{(m-w)}H_{((2m+1)-2w)}O_wO_z$, $O_2CC_{(m-w)}H_{((2m+1)-2w)}O_wO_z$ or $N(R)OCC_{(m-w)}H_{((2m+1)-2w)}O_wO_z$. In this case, m is a positive integer from 1 to 10, w is zero or a positive integer less than or equal to m, z is zero or a positive integer less than or equal to $((2m+1)-2w)$, and R is H, alkyl, hydroxyalkyl, or $C_mH_{((2m+1)-r)}O_zR^b_r$. In this case, m is a positive integer from 1 to 10, z is zero or a positive integer less than $((2m+1)-r)$, r is zero or a positive integer less than or equal to 2m+1, and $R^b$ is independently H, alkyl, hydroxyalkyl, or saccharide. In a preferred embodiment, $R^c$ is an oligonucleotide.

In presently preferred texaphyrins, $R_1$ is hydroxyalkyl and $R_2$, $R_3$ and $R_4$ are alkyl; or at least one of $R_1$, $R_2$, $R_3$, $R_4$, $R_5$ and $R_6$ is a site-directing molecule or a couple to a site-directing molecule. Alternatively, $R_3$, $R_5$ or $R_6$ may be a site-directing molecule or a couple to a site-directing molecule. A site-directing molecule is a hormone or is preferably an oligonucleotide or a couple to an oligonucleotide. The oligonucleotide may be a deoxyribonucleotide or a ribonucleotide analog. A preferred ribonucleotide analog, for example, has methyl groups on the 2' oxygen of the ribose.

In a further preferred texaphyrin for the above-described method, $R_1$ is $(CH_2)_2CH_2OH$, $R_2$ and $R_3$ are $CH_2CH_3$, $R_4$ is $CH_3$ and $R_5$ and $R_6$ are $OCH_2CH_2CH_2OH$. Alternatively, $R_5$ is a site-directing molecule or a couple thereto, preferably an oligonucleotide or a couple thereto, more preferably $O(CH_2)_nCO$-oligonucleotide where n is 1–7 and preferably 1–3; and $R_6$ is H. In a further presently preferred embodiment, $R_1$ is $(CH_2)_2CH_2OH$, $R_2$ and $R_3$ are $CH_2CH_3$, $R_4$ is $CH_3$, $R_5$ is $O(CH_2CH_2O)_2CH_2CH_2OCH_3$, and $R_6$ is a site-directing molecule or a couple thereto, preferably an oligonucleotide or a couple thereto, more preferably $O(CH_2)_nCO$-oligonucleotide where n is 1–7 and preferably 1–3. In other presently preferred embodiments, $R_1$–$R_6$ are as in Table 1 for texaphyrins A1–A22.

In a further preferred embodiment of the above described method, the oligonucleotide has complementary binding affinity for the DNA in a region proximal to the cleavage site. The oligonucleotide may have complementary binding affinity for viral DNA and upon cleavage by the texaphyrin-oligonucleotide conjugate, the virus would be killed. The oligonucleotide may have complementary binding affinity for oncogenes or may have binding specificity for localization to a treatment site. A hormone may have binding specificity for a biological receptor and the receptor is localized to a treatment site. The hormone or hormone mimic may be estradiol, histamine or morphine, for example.

This method of site specific cleavage of DNA involves two sources of specificity. A complementary oligonucleotide is designed to base pair with the targeted substrate and the second source of specificity for in vitro or in vivo applications is the positioning of the laser light. Such positioning of laser light, either by manual or mechanical means, would be particularly advantageous when the oligonucleotide cleavage reaction in question is to be effected at a particular biological locus, such as, for instance, a deep-seated tumor site. Here, the fact that the texaphyrins absorb light at wavelengths where bodily tissues are relatively transparent (700–900 nm) is particularly advantageous. This procedure allows for the effective implementation of light-based oligonucleotide strategies at loci deep within the body with relatively little deleterious light-based photosensitization of other tissues where the texaphyrin conjugates are not localized.

The use of texaphyrin metal complexes to cleave DNA in vivo as a treatment procedure relies on the effective localization of the complex to the site of desired cleavage. A site of desired cleavage may be a position novel to undesired organisms in terms of health care. A site of desired cleavage may be a DNA encoding a product deleterious to the host or may be a normal DNA that is deleterious in some way. The binding of a conjugate to a DNA double helix will form a triple helix which has sufficient stability for effective cleavage to occur.

The data of Examples 10 and 11 demonstrate that diamagnetic metal-texaphyrin-oligonucleotide conjugates may be developed into DNA antisense reagents. This antisense strategy provides a clear and rational method for new drug design because there is one requirement, namely that the antisense probe hybridize to its target molecule. The hybridization requirement is very well understood via complementary Watson-Crick or Hoogsteen base pairing. Unlike the present methods in the art which require screening of thousands of compounds and X-ray crystal structure analysis, the information needed for antisense technology is the sequence of the target. Treating native DNA with this new texaphyrin-oligonucleotide conjugate results in the conjugate binding to a complementary DNA sequence via the appended oligonucleotide. The diamagnetic metal-texaphyrin complex then cleaves the DNA proximal to this specific site. Two texaphyrin molecules may be attached to a conjugated oligonucleotide enhancing the cleavage activity. Also, a greater number of texaphyrins attached to the olignucleotide will cause the antisense agent to take on the pharmacodynamic and biodistribution properties of the texaphyrin such as selective localization in tumors.

The texaphyrin oligonucleotide-conjugate would have immediate applications for anti-viral and anti-bacterial therapy as well as cancers (an oligonucleotide complementary to an oncogene, for example) and inflammatory responses that are caused by the overexpression of certain proteins. Antisense technology is discussed in U.S. Pat. Nos. 5,194,428, 5,110,802 and 5,216,141, all of which are incorporated by reference herein. Metal-free and diamagnetic metallated texaphyrin compounds, methods for making and methods for using them are described in U.S. Pat. Nos. 4,935,498, 5,162,509, 5,252,720, 5,272,142, 5,256,399, and 5,292,414; and in pending applications U.S. Ser. No. 08/098,514, 08/100,093, now U.S. Pat. No. 5,432,171, 08/112,786, now U.S. Pat. No. 5,439,570, 08/112,786, 08/112,872, now U.S. Pat. No. 5,451,578, 08/135,118, 08/168,668, now U.S. Pat. No. 5,369,101, 08/196,964, 08/227,370, 08/207,845, and 08/236,218; each patent and application is incorporated by reference herein. Sapphyrin compounds are disclosed in U.S. Pat. Nos. 5,041,078, 5,159,065, 5,120,411 and 5,302,714; and in application 07/964,607, now U.S. Pat. No. 5,457,195; each patent and application is incorporated by reference herein.

A further embodiment of the present invention is a method of incorporating sapphyrin or texaphyrin before, during, or after chemical synthesis of an oligomer to form a sapphyrin- or texaphyrin- oligonucleotide conjugate. This method comprises the steps of obtaining an automated or manual DNA synthesizer having a solid support. Further steps include reacting derivatized nucleotides, and a sapphyrin, or a texaphyrin in a desired order to form a sapphyrin- or a texaphyrin- oligonucleotide conjugate. For example, an oligonucleotide may be formed by repeated steps of reacting nucleotides on the solid support. Sapphyrin or texaphyrin may be coupled in the final step to form a conjugate with a 5' linkage. Alternatively, a sapphyrin or texaphyrin may be coupled to the solid support followed by the addition of nucleotides to form a conjugate with a 3' linkage. A third possibility is the coupling of nucleotides followed by a macrocycle, such as texaphyrin or sapphyrin, then followed by nucleotides to form a conjugate where an internal residue is a macrocycle.

The oligonucleotide may be linked to the sapphyrin or texaphyrin in a 3' linkage, a 5' linkage, or a linkage internal to the oligonucleotide. The texaphyrin or sapphyrin may be coupled as a phosphoramidite, H-phosphonate, or phosphate triester derivative and may be coupled to the growing end of the oligonucleotide in the synthesizer during or in the final step of synthesis.

Another embodiment of the present invention is a method for targeted intracellular DNA cleavage. The method comprises the introduction into a cell of a texaphyrin coupled to an oligonucleotide having complementary binding affinity for a targeted DNA, whereby cleavage of the targeted DNA is catalyzed by the texaphyrin. The DNA may be oncogene DNA or may be normal DNA which needs to be destroyed, for example, due to improper timing of expression. The oligonucleotide coupled to the texaphyrin may be DNA, a DNA analog, or an RNA analog oligonucleotide. The texaphyrin may be a free base texaphyrin or a metallated form of texaphyrin. The metal is preferably a diamagnetic metal, most preferably Lu(III).

A method for inhibiting the expression of a gene in an animal comprising the administration to the animal of a texaphyrin oligonucleotide-conjugate is a further embodiment of the present invention. The oligonucleotide may have complementary binding affinity for regulatory regions of the gene or for regions encoding exons or introns. The oligonucleotide may be complementary to either strand of the DNA or to the duplex DNA. A further embodiment of the present invention is a method for inhibiting the expression of a gene in a particular tissue of an animal comprising administering to the animal a texaphyrin having specificity for the tissue. The texaphyrin may have appended an oligonucleotide complementary to the target gene.

A further embodiment of the present invention is a texaphyrin conjugate wherein two or more separate texaphyrin complexes are attached to an oligonucleotide, one at the 3', one at the 5' end, and/or one or more at an internal residue. The texaphyrin may be metal free or may be metallated. A metal ion of each of the texaphyrin complexes may be the same or it may be different. Similarly, each of the texaphyrins may be different. Use of a dual texaphyrin complex-conjugate should effect the cleavage of DNA with increased efficiency due to the concerted activity of the metal complexes. For diagnosis and treatment purposes, the administration of such a conjugate with one texaphyrin complex having a diamagnetic metal species and the other having a paramagnetic species would allow binding, imaging, and cleavage, all effected by one conjugate. In this case, binding is effected by the oligonucleotide, imaging is accomplished by MRI due to the presence of the paramagnetic metal ion, and cleavage is accomplished by the photosensitive texaphyrin containing a diamagnetic metal cation. Therefore, the biodistribution and cellular penetration of the conjugate may be determined.

Following long-standing patent law convention, the terms "a" and "an" mean "one or more" when used in this application, including the claims.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2A, FIG. 2B and FIG. 2C demonstrate the covalent coupling of texaphyrin metal complexes with amine, thiol or hydroxy linked oligonucleotides.

FIG. 6A shows the synthesis of a texaphyrin metal complex 3'-linked-oligonucleotide conjugate. FIG. 6B and FIG. 6C show an approach that results in a 5' linked oligonucleotide conjugate. FIG. 6D shows the synthesis of a 5'-linked sapphyrin-oligonucleotide conjugate. FIG. 6E shows the synthesis of a precursor sapphyrin that may be linked to two oligonucleotides. FIG. 6F and FIG. 6G show the synthesis of sapphyrin oligonucleotide conjugate via the H-phosphonate method. Example 9 provides the details of these stepwise synthesis schemes.

FIG. 8 shows lutetium texaphyrin-RNA analog oligonucleotide conjugates hybridized to template DNA. The RNA analog is the 2'-O-methylated derivative of the ribonucleotide.

FIG. 9A, 9Bi and FIG. 9Bii depicts a texaphyrin "fluorescent switch" for detecting a sequence in DNA as described in Example 15. "B" represents a base present in nucleic acid.

FIG. 10A, FIG. 10Bi and FIG. 10Bii depicts a further texaphyrin "fluorescent switch" for detecting a sequence in DNA having a different texaphyrin at each end of the probe as described in Example 15. $M_1$ is H or a diamagnetic metal cation, $M_2$ is a paramagnetic metal cation or a diamagnetic metal cation with lower excited state energetics as compared to $M_1$. "B" represents a base present in nucleic acid.

DETAILED DESCRIPTION OF THE PREFERRED EMBODIMENTS

Figure 1A:
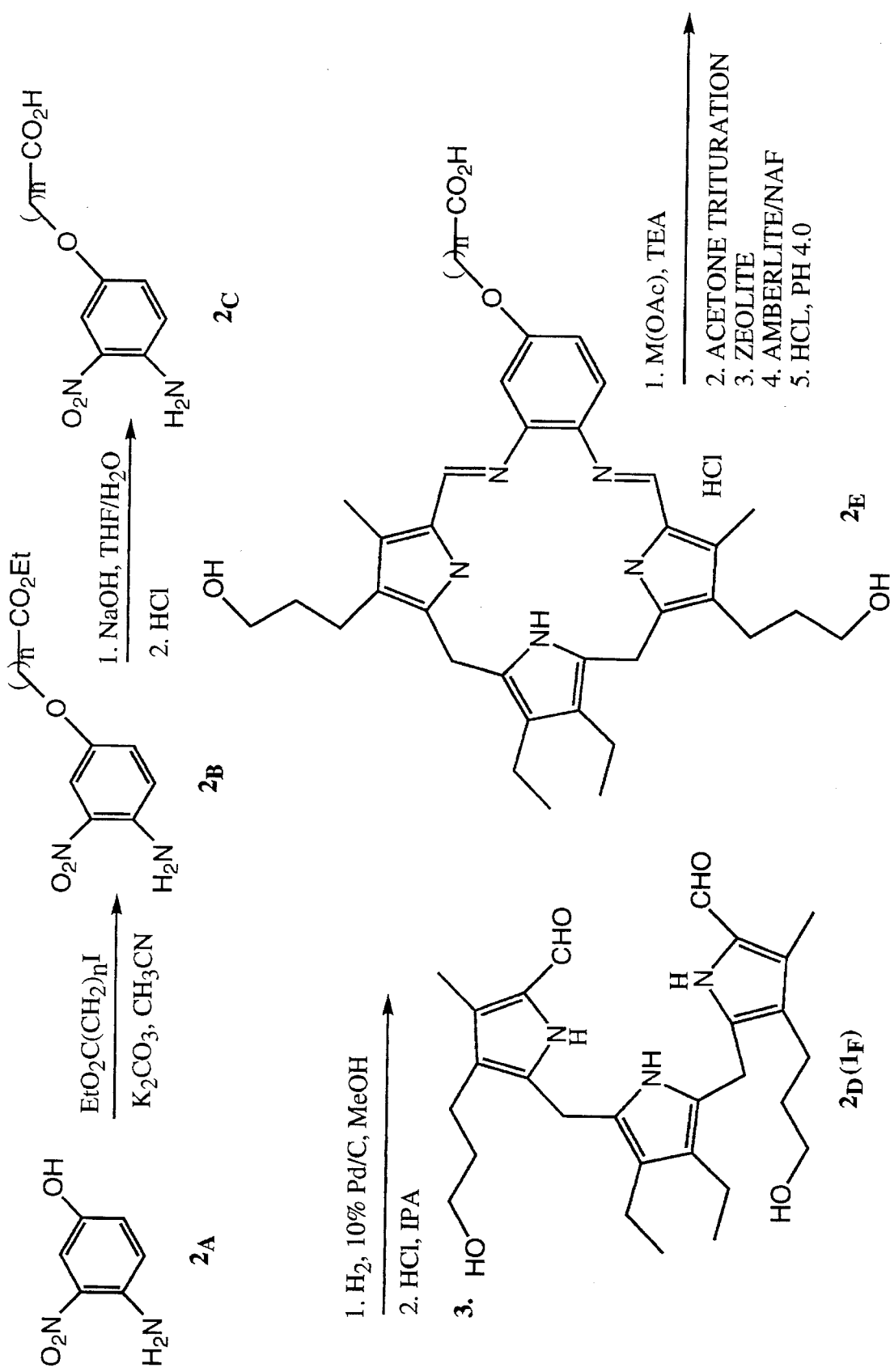
FIG. 1A and FIG. 1B schematically summarize the synthesis of an oligonucleotide conjugate of a texaphyrin metal complex, $2_H$.

The present invention involves the use of photosensitive texaphyrins for the photodynamic treatment of tumor cells and atheroma in vivo and for the photoinduced cleavage of a polymer of deoxyribonucleic acid. The photosensitive texaphyrin may be a free base texaphyrin or may be metallated with a diamagnetic metal.

More particularly, the invention involves the site-specific cleavage of a polymer of deoxyribonucleic acid using a photosensitive texaphyrin metal complex-oligonucleotide conjugate where the oligonucleotide is a site-directing molecule having sequence complementarity to a portion of the DNA to be cleaved. A preferred diamagnetic metal is Lu(III), La(III), In(III), Zn(II), or Cd(II) and a most preferred diamagnetic metal is Lu(III).

An individual skilled in the art of organic synthesis in light of the present disclosure is able to prepare a large variety of photosensitive texaphyrins, all of which are expected to cleave DNA, an important biological species. Potential particular applications for this process include the specific cleavage and possible subsequent recombination of DNA; destruction of viral DNA; construction of probes for controlling gene expression at the cellular level and for diagnosis; and cleavage of DNA in footprinting analyses, DNA sequencing, chromosome analyses, gene isolation, recombinant DNA manipulations, mapping of large genomes and chromosomes, in chemotherapy, and in site-directing mutagenesis.

The methods of the present invention are useful in photodynamic therapy, the targeted light-induced killing of cells in the vicinity of a photosensitive molecule. Examples 12–14 provide data demonstrating the in vivo killing of tumor cells and destruction of atheromatous plaque.

Texaphyrins of the present invention may be metal free or may be in a complex with a metal. For generating singlet oxygen, the preferred metal is a diamagnetic metal. Divalent and trivalent metal complexes of texaphyrins are by convention shown with a formal charge of $N^+$, where N=1 or 2, respectively. It is understood by those skilled in the art that the complexes described in the present invention have one or more additional ligands providing charge neutralization and/ or coordinative saturation to the metal ion. Such ligands include chloride, nitrate, acetate, and hydroxide, among others.

Exemplary texaphyrins of the present invention are listed in Table 1.

The bacterial strain used to harbor the plasmid DNA, pGEM3Z, was *E. coli* DH5α from Bethesda Research Laboratories (Gaithersburg, Md.). The plasmid used was pGEM3Z from Promega (Madison, Wisc.) with the 4.3 kb fragment of mouse MDR1a inserted at the EcoRI site.

TABLE 1

Representative Substituents for Texaphyrin Macrocycles of the Present Invention

| TXP | $R_1$ | $R_2$ | $R_3$ | $R_4$ | $R_5$ | $R_6$ |
|---|---|---|---|---|---|---|
| A1 | $CH_2(CH_2)_2OH$ | $CH_2CH_3$ | $CH_2CH_3$ | $CH_3$ | $O(CH_2)_3OH$ | $O(CH_2)_3OH$ |
| A2 | " | " | " | " | $O(CH_2CH_2O)_3CH_3$ | $O(CH_2CH_2O)_3CH_3$ |
| A3 | " | " | " | " | $O(CH_2)_n CON$-linker-site-directing molecule, n = 1–7 | " |
| A4 | " | " | " | " | $O(CH_2)_n CON$-linker-site-directing molecule | H |
| A5 | " | " | " | " | $OCH_2CO$-hormone | " |
| A6 | " | " | " | " | $O(CH_2CH_2O)_3CH_3$ | " |
| A7 | " | " | " | " | $OCH_2CON$-linker-site-directing molecule | $O(CH_2CH_2O)_3CH_3$ |
| A8 | " | " | " | " | $OCH_2CO$-hormone | " |
| A9 | " | " | " | " | $O(CH_2CH_2O)_{120}CH_3$ | $O(CH_2CH_2O)_3CH_2$—$CH_2$—N-imidazole |
| A10 | " | " | " | " | saccharide | H |
| A11 | " | " | " | " | $OCH_2CON(CH_2CH_2OH)_2$ | " |
| A12 | " | " | " | " | $CH_2CON(CH_3)CH_2$—$(CHOH)_4CH_2OH$ | " |
| A13 | " | COOH | COOH | " | $CH_2CON(CH_3)CH_2$—$(CHOH)_4CH_2OH$ | " |
| A14 | " | $COOCH_2CH_3$ | $COOCH_2CH_3$ | " | $CH_2CON(CH_3)CH_2$—$(CHOH)_4CH_2OH$ | " |
| A15 | $CH_2CH_2CON(CH_2CH_2OH)_2$ | $CH_2CH_3$ | $CH_2CH_3$ | " | $CH_2CON(CH_3)CH_2$—$(CHOH)_4CH_2OH$ | " |
| A16 | $CH_2CH_2ON(CH_3)CH_2$—$(CHOH)_4CH_2OH$ | " | " | " | $OCH_3$ | $OCH_3$ |
| A17 | $CH_2(CH_2)_2OH$ | " | " | " | $O(CH_2)_n COOH$, n = 1–7 | H |
| A18 | " | " | " | " | $(CH_2)_n$—CON-linker-site-directing molecule, n = 1–7 | " |
| A19 | " | " | " | " | $YCOCH_2$-linker-site-directing molecule Y = NH, O | " |
| A20 | $CH_2CH_3$ | $CH_3$ | $CH_2CH_2COOH$ | " | $O(CH_2)_2CH_2OH$ | $O(CH_2)_2CH_2OH$ |
| A21 | " | " | $CH_2CH_2CON$-oligo | " | " | " |
| A22 | $CH_2(CH_2)_2OH$ | $CH_2CH_3$ | $CH_2CH_3$ | " | $O(CH_2)_3CO$-histamine | H |

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Cleavage of Plasmid DNA Using a Texaphyrin-Lu(III) Complex

The present example demonstrates the use of a texaphyrin diamagnetic complex for the cleavage of DNA, in particular, the use of a Lu(III)txp complex for the cleavage of plasmid DNA, pGEM3Z and pBR322.

Growth conditions were LB (Luria broth) with ampicillin at 100 μg/mL. Cultures were inoculated and gently shaken overnight at 37° C.

A mini-prep of plasmid pGEM3Z DNA was obtained as follows. The pellet from 1.5 mL of an overnight culture was resuspended in 110 μl of solution A (25 mM Tris pH 8.9, 25 mM EDTA, 20% glucose and 1 mg/mL lysozyme). This suspension was left 5 min at room temperature, then 220 μl of solution B (0.2N NaOH, 1% SDS) was gently added. The tubes were mixed well and left to stand 5 min at room temperature. Then, 180 μl of 3M Na/K Acetate pH 5.2 (30 mL of 5M potassium acetate (KAc) and 20 mL of glacial acetic acid) was added, the tubes were mixed well, and spun 10 min. The cleared supernatant was transferred to fresh tubes and extracted with chloroform/isoamyl alcohol (24:1). The extracted aqueous layer was then precipitated with 1.0 mL of ethanol (200 proof) at room temperature. Tubes were mixed well and spun 10 minutes at room temperature. Pellets were dried briefly and resuspended in 100 μl of 1×TE.

A large scale preparation of plasmid PGEM32 DNA was obtained as follows. The pellet from 1 L of an overnight culture was resuspended in 25 mL of solution A, lysed with 50 mL of solution B, and precipitated with 40 mL of 3M Na/KAc. The cleared lysate was filtered through sterile gauze and extracted with 100 mL of chloroform. The cleared, extracted lysate was then precipitated at room temperature with 70 mL of isopropyl alcohol. The pellet was then resuspended in 2 mL of 1×TE. 2 gm of CsCl was added and dissolved. The solution was loaded into ultracentrifuge tubes with 0.5 mL of 10% sarcosyl and 0.5 mL of ethidium bromide (15 mg/mL). A solution of CsCl in 1×TE (1 gm/mL) was added as all overlay until the tube was full. Tubes were spun until equilibrium was reached. Bands were pulled with a needle and syringe and were rebanded with more fresh overlay solution in the same or smaller size tubes and spun again. The respun band was pulled again with a needle and syringe, extracted 6× with butanol, dialyzed against several changes of 1×TE, and ethanol precipitated. The pellet was resuspended in 1×TE and the concentration determined by UV spectroscopy.

Approximately 800 ng of plasmid DNA (10 µl, 10 mM Tris, 1 mM EDTA) were mixed with stock solutions of LuB2T2 txp in DMSO to a final volume of 20 µL. Concentrations of 50, 100, and 200 µM LuB2T2 txp were tested. A control containing DMSO only was also included. The tubes containing the mixtures were allowed to incubate for 3 hours at 37° C. All samples were in duplicate: one tube was left in a bacterial incubator wrapped in foil (the "dark" sample) and the second tube was kept in a tissue culture incubator with fluorescent lights on (the "light" sample). After 3 hours, the samples were loaded onto 0.8% agarose gels in 1×TAE and electrophoresis was carried out with ethidium bromide present. HindIII digested λ DNA was included as molecular weight markers.

DNA bands were present in the control lane and in the lane for the 50 µM LuB2T2txp sample held in the dark. The sample exposed to light at 50 µM LuB2T2 was degraded. In all the other samples with greater concentrations of texaphyrin, the DNA was precipitated by the LuB2T2txp.

Further samples of supercoiled plasmid pGEM3Z was purified by cesium chloride density gradient centrifugation, after which ~200 ng was mixed with various concentrations of LuB2T2txp in distilled water to a final volume of 20 µL. Concentrations of 1, 5, 10, 25 and 50 µM of LuB2T2txp were tested. Following the procedures described above, light and dark samples were incubated for 2 hours and the samples were then applied to a 0.8% 1×TAE agarose gel and electrophoresis was carried out in the presence of ethidium bromide. A control without LuTxp was also run. Hind III digested λ DNA was included as molecular weight markers.

At 25 µM texaphyrin incubated in the light, less material was present in the lower band (supercoiled DNA) and it had shifted up to the higher band (nicked circle), indicating some DNA strand cleavage. There was no difference for the 25 µM txp sample held in the dark or at lower concentrations of LuTxp compared to the control. Therefore, DNA is not degraded at these lower concentrations under these conditions. At 50 µM LuB2T2txp, the DNA was precipitated.

To determine the degradation potential of texaphyrins for linearized DNA, 250 ng of linearized DNA (obtained by digestion of pGEM3Z plasmid and gel isolation) was mixed with either LuB2T2 txp or with lutetium acetate in distilled water to a final volume of 20 µL. The samples were: 50 µM LuB2T2txp; 50 µM LuB2T2txp+ 25 mM EDTA; 50 µM LuB2T2txp+free phosphate at 100, 10, or 1 µM; 25 µM LuB2T2txp; 25 µM LuB2T2txp+25 mM EDTA; 50 µM Lu acetate; 50 µM Lu acetate+25 mM EDTA; 50 µM Lu acetate+free phosphate at 100, 10 or 1 µM; and 100 µM phosphate only, as the control. Following the procedures described above, light and dark samples were incubated for 2 hours and then individually separated by electrophoresis on a 0.8% 1×TAE agarose gel with ethidium bromide.

LuB2T2txp precipitated the linearized DNA at 50 µM with or without EDTA or free phosphate. At 25 µM LuB2T2txp, both with and without EDTA, there was a difference between the light and dark samples; the light reaction resulted in DNA degradation while the dark reaction left the material intact. The presence of free phosphate had no effect on the degradation of DNA. Free lutetium, either alone or in the presence of phosphate, did not degrade DNA. The band containing free lutetium with EDTA showed a barely detectable loss of intensity and also smearing, so that there may have been some precipitation of DNA, possibly due to the high concentration of EDTA.

In another experiment, 350 ng of linearized pGEM3Z DNA were mixed with 1, 5, 10, 25, or 50 µM of LuB2T2txp, and samples were separated by electrophoresis on agarose gels as described above. At 50 µM LuB2T2 txp, the DNA was precipitated by the LuB2T2 txp. At 25 µM of the texaphyrin in the light sample, there was a less intense signal, indicating degradation of the DNA. The DNA was not degraded for the 25 µM txp dark reaction or the lower concentrations of the texaphyrin.

In a further experiment, pBR322 plasmid DNA was found to be cleaved by LuB2T2 Txp at a concentration of 4 µM. The experimental conditions were as follows: Irradiated solutions contained 100 µl 0.1 SSC buffer (saline sodium citrate: 15 mM NaCl, 1.5 mM sodium citrate, pH 7.0), 32 µM pBR322 DNA phosphates and either 0 or 4 µM LuTxp. Plasmid pBR322 was purchased from Gibco BRL and contained greater than 90% supercoiled DNA. Solutions were irradiated at room temperature with a high pressure Xenon lamp through a pyrex filter to stop UV light of wavelengths below about 300 nM. Samples were irradiated in a quartz cuvette measuring 1 mm in diameter and received approximately 3400 W/m$^2$. After irradiation, 3 µl 50% glycerol/water loading buffer containing bromophenol blue was added to 9 µl irradiated solution. The samples were analyzed on a 0.8% agarose gel containing ethidium bromide in tris-acetate buffer at 90 V for 30 minutes. The DNA was detected by fluorescence using a UV lamp.

No nicking or cleavage was seen in a control sample without texaphyrin or in a control sample with texaphyrin but without light. In the presence of LuTxp and light for 5, 10, and 20 minutes, the supercoiled form of the DNA gradually disappeared and the relaxed form appeared. A small amount of linear DNA was also formed.

The mechanism of cleavage of DNA is not known at this time, however, it has been observed by the present inventors that light plays an important role in the cleavage mechanism since cleavage occurs in the light but not in the dark. Diamagnetic metal cations such as In(III), La(III), Zn(II), or Cd(II) may also effect cleavage since texaphyrin complexes of these metal cations are photosensitive.

EXAMPLE 2

A Texaphyrin-Paramagnetic Metal Complex Does Not Effect DNA Cleavage

The present example demonstrates the activity of a diamagnetic metal Lu(III)texaphyrin complex for light-activated cleavage of DNA, and compares it with the lack of cleavage activity by a paramagnetic metal Dy(III)texaphyrin complex. DNA samples were incubated with the diamagnetic metal texaphyrin complex, LuB2T2, or the paramagnetic metal texaphyrin complex, DyB2T2, in the dark or in the light and separated by electrophoresis on a polyacrylamide gel.

Figure 7:
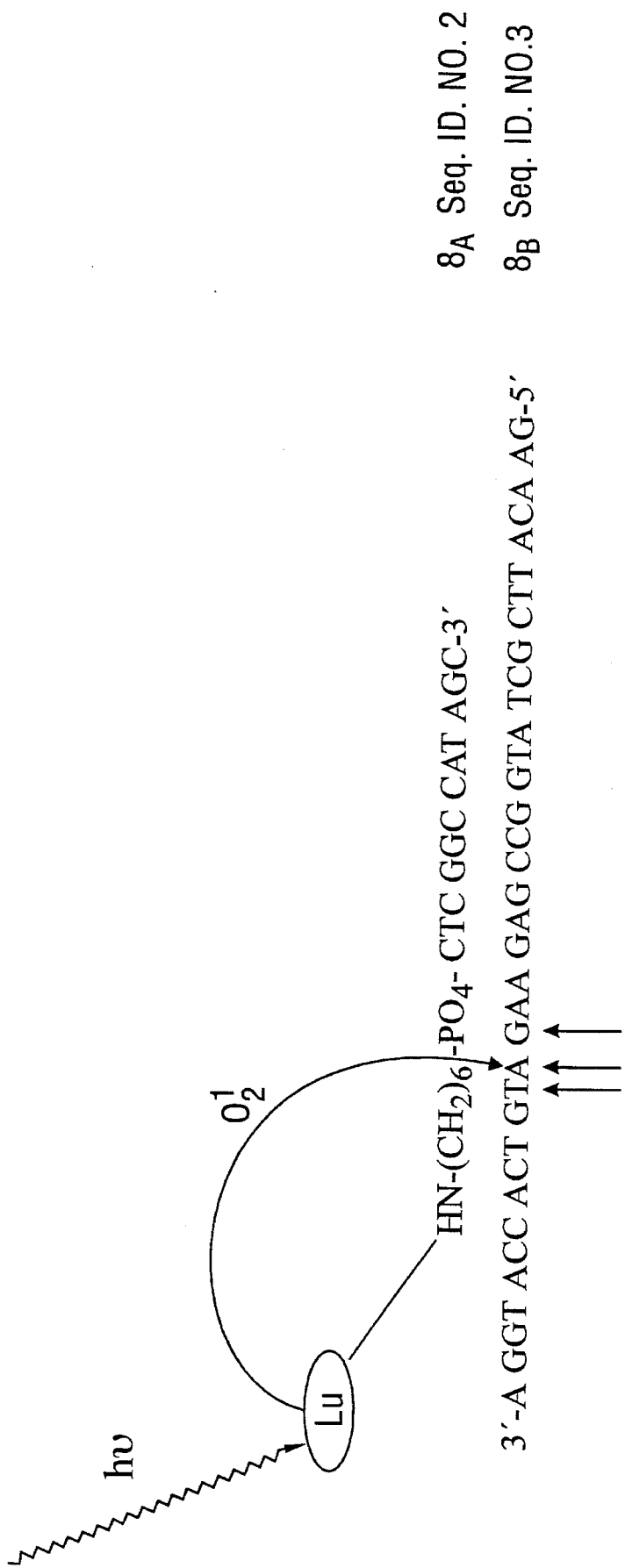
FIG. 7 shows site-specific cleavage of DNA by a Lu(III)Txp-oligodeoxynucleotide conjugate.

Ten μL (approximately 200,000 cpm) of 5'-$^{32}$P-labelled DNA 36-mer ($A_2$ of FIG. 7) was added to a solution of 10 μL of 4× buffer (400 mM NaCl, 200 mM HEPES, pH 7.5, 100 μM EDTA). To this was added 20 μL of either 2 μM lutetium(III) B2T2 texaphyrin (LuB2T2txp) or 2 μM dysprosium(III) B2T2 texaphyrin (DyB2T2txp) in deionized water to give a final volume of 40 μL reaction solution in an Eppendorf tube. Final texaphyrin complex concentration was 1 μM. Two tubes of reaction mixture containing LuB2T2txp and two tubes of reaction mixture containing DyB2T2txp were prepared. An additional reaction mixture was prepared in the same way, except that an equal volume of water was substituted for the texaphyrin solution, as the control. One of each of the LuB2T2txp and DyB2T2txp tubes was left in a bacterial incubator wrapped in foil (the "dark" sample) and the second tube containing each complex was kept in a tissue culture incubator with fluorescent lights on (the "light" sample). The control tube was kept in the light and was not incubated. The texaphyrin tubes were incubated overnight (ca. 14 hours) at 37° C., after which all samples were loaded onto a polyacrylamide gel and separated by electrophoresis following procedures described herein. Lane 1, control; lane 2, LuB2T2 in the dark; lane 3, LuB2T2 in the light; lane 4, DyB2T2 in the dark; lane 5, DyB2T2 in the light.

In the control sample, a DNA band was present corresponding to the 36-mer substrate. In the DyB2T2txp lanes, both light and dark, and the LuB2T2txp dark lane, a DNA band of the same size was present. However, the DNA was degraded in the LuB2T2txp sample exposed to light indicating that, in the presence of light, the diamagnetic texaphyrin complex cleaved the DNA.

EXAMPLE 3

Synthesis of a T2B1 TXP metal complex-oligonucleotide conjugate

Figure 1B:
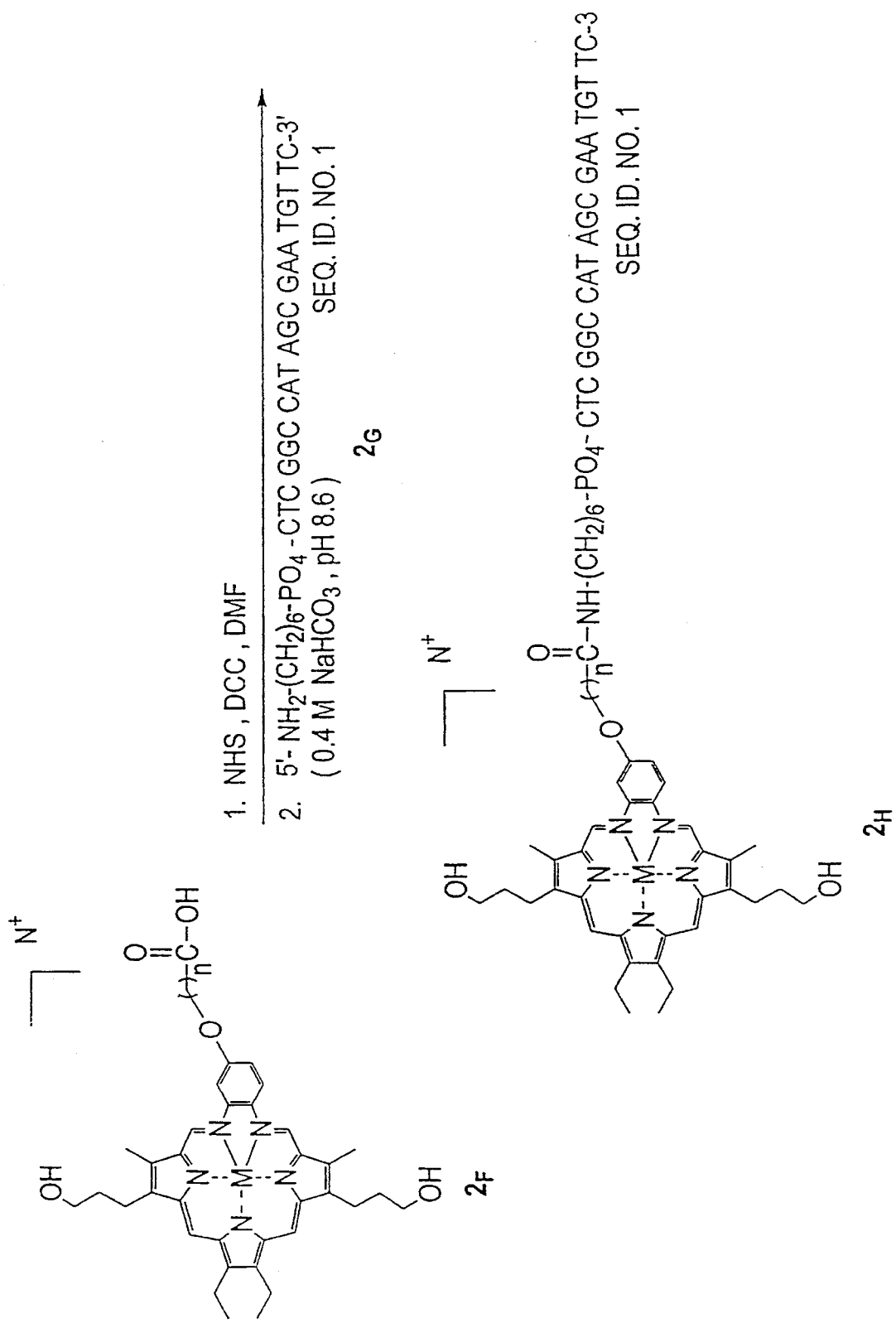

The present example provides for the synthesis of a texaphyrin metal complex-oligonucleotide conjugate useful for site-directed cleavage of a complementary DNA (see FIG. 1A and FIG. 1B).

4-Amino-1-[1-(ethyloxy)acetyl-2-oxy]-3-nitrobenzene $2_B$, n=1. Potassium carbonate (14.0 g, 101 mmol) and 4-amino-3-nitrophenol $2_A$ (10.0 g, 64.9 mmol) were suspended in 150 mL dry acetonitrile. Ethyl-2-iodoacetate (10 mL, 84.5 mmol) (or ethyl iodobutyrate may be used, in that case n=3) was added via syringe, and the suspension was stirred at ambient temperature for ca. 21 h. Chloroform (ca. 375 mL) was added and was used to transfer the suspension to a separatory funnel, whereupon it was washed with water (2×ca. 100 mL). The water washes were in turn washed with CHCl$_3$ (ca. 100 mL) and the combined CHCl$_3$ extracts were washed with water (ca. 100 mL). Solvents were removed on a rotary evaporator, and the residue was redissolved in CHCl$_3$ (ca. 500 mL) and precipitated into hexanes (1.5 L). After standing two days, the precipitate was filtered using a coarse fritted funnel and dried in vacuo to provide 14.67 g compound $2_B$, n=1 (94.1%). TLC: Rf=0.43, CHCl$_3$.

4-Amino-1-[1-(hydroxy)acetyl-2-oxy]-3-nitrobenzene $2_C$, n=1. 4-Amino-1-[1-(ethyloxy)acetyl-2-oxy]-3-nitrobenzene $2_B$, n=1, (10.00 g, 37.3 mmol) was dissolved in tetrahydrofuran (100 mL), aqueous sodium hydroxide (1M solution, 50 mL) was added and the solution was stirred at ambient temperature for ca. 21 h. Tetrahydrofuran was removed on a rotary evaporator, and water (100 mL) was added. The solution was washed with CHCl$_3$ (ca. 200 mL), then neutralized by addition of hydrochloric acid (1M solution, 50 mL). The precipitate which formed was filtered after standing a few minutes, washed with water, and dried in vacuo to provide 8.913 g compound $2_C$, n=1 (99.5%). TLC: Rf= 0.65, 10% methanol/CHCl$_3$.

16-[1-(Hydroxy)acetyl-2-oxy]-9,24-bis(3-hydroxypropyl)- 4,5-diethyl-10,23-dimethyl-13,20,25,26,27-pentaazapentacyclo[20.2.1.1$^{3,6}$.1$^{8,11}$.0$^{14,19}$] heptacosa-3,5,8,10,12, 14(19), 15,17,20,22,24-undecaene $2_E$, n=1. 4-Amino-1-[1-(hydroxy)acetyl- 2-oxy]-3-nitrobenzene $2_C$, n=1 (1.800 g, 8.49 mmol) was dissolved in methanol (100 mL) in a 1L flask. Palladium on carbon (10%, 180 mg) was added, and the atmosphere inside the flask was replaced with hydrogen at ambient pressure. A grey precipitate was formed after ca. 3 h, and the supernatant was clear. Methanol was removed in vacuo, taking precautions to prevent exposure to oxygen, and the compound was dried overnight in vacuo. Isopropyl alcohol (500 mL) and HCl (12M, 400 μL) were added, and the suspension was allowed to stir for ca. 15'. 2,5-Bis[(3-hydroxypropyl-5-formyl-4-methylpyrrol-2-yl)methyl]-3,4-diethylpyrrole $2_D$ (n=1) (4.084 g, 8.49 mmol) was added, and the reaction stirred at room temperature under argon for 3 hours. Hydrochloric acid was again added (12M, 400 μL) and the reaction again was allowed to stir for an additional 3.5 h. The resulting red solution was filtered through celite, and the filtercake was washed with isopropyl alcohol until the filtrate was colorless. Solvent was reduced to a volume of ca. 50 mL using a rotary evaporator, whereupon the solution was precipitated into rapidly stirring Et$_2$O (ca. 700 mL). Compound $2_E$ (n=1) was obtained as a red solid (5.550 g, 98.4%) upon filtering and drying in vacuo. TLC: R$_f$=0.69, 20% methanol/CHCl$_3$ (streaks, turns green on plate with I$_2$).

Metal complex of 16-[1-(hydroxy)acetyl-2-oxy]-9,24-bis(3-hydroxypropyl)- 4,5-diethyl-10,23-dimethyl-13,20, 25,26,27-pentaazapentacyclo [20.2.1.1$^{3,6}$.1$^{8,11}$.0$^{14,19}$]heptacosa- 1,3,5,7,9,11(27),12,14(1 9),15,17,20,22(25),23-tridecaene $2_F$, n=1. Approximately equal molar amounts of the protonated form of the macrocycle, 16-[1-(hydroxy) acetyl-2-oxy]-9,24-bis(3-hydroxypropyl)- 4,5-diethyl-10, 23-dimethyl-13,20,25,26,27-pentaazapentacyclo[ 20.2. 0.1.1$^{3,6}$.1$^{8,11}$.0$^{14,19}$] heptacosa- 3,5,8,10,12,14(19),15,17,20, 22,24-undecaene hydrochloride $2_E$, n=1, and a metal acetate pentahydrate were combined with triethylamine in methanol, and were heated to reflux under air for 5.5 h. The reaction was cooled to room temperature, and stored at −20° C. overnight. Solvent was removed on a rotary evaporator, acetone was added, and the suspension was stirred on a rotary evaporator for 2 h. The suspension was filtered and the precipitate dried briefly in vacuo, whereupon a solution was formed in methanol (ca. 250 mL) and water (25 mL). The pH was adjusted to 4.0 using HCl (1M), HCl-washed zeolite LZY54 was added (ca. 5 g) and the suspension was stirred on the rotary evaporator for ca. 6 h. Amberlite™ IRA-900 ion exchange resin (NaF treated, ca. 5 g) was added, and the suspension was stirred for an additional hour. The suspension was filtered, the resin was washed with methanol (ca. 100 mL), and the filtrate was adjusted to pH 4.0 using HCl (1M). Solvents were removed on a rotary evaporator, using ethanol (abs.) to remove traces of water.

After drying in vacuo, the compound was dissolved in methanol (25 mL) and precipitated into rapidly stirring $Et_2O$ (300 mL). Compound $2_F$, n=1, was obtained as a precipitate after filtering and drying in vacuo. An analytical sample was prepared by treating 50 mg of $2_F$, n=1, dissolved in methanol (25 mL) with acetic acid-washed zeolite, then acetic acid-washed Amberlite™ for ca. 1 h. After reducing methanol to a minimum volume, the solution was precipitated into rapidly stirring $Et_2O$ (70 mL), filtered, and dried in vacuo.

Postsynthetic modification of oligodeoxynucleotide-amine $2_G$ with metal complex $2_F$, n=1. The metal complex of 16-[1-(hydroxy)acetyl- 2-oxy]-9,24-bis(3-hydroxypropyl)-4,5-diethyl- 10,23-dimethyl-13,20,25,26,27-pentaazapentacyclo [20.2.1.1$^{3,6}$.1$^{8,11}$.0$^{14,19}$]heptacosa-1,3,5,7,9, 11(27),12, 14(19),15,17,20,22(25),23-tridecaene $2_F$, n=1, (about 30 μmol) and N-hydroxysuccinimide (43 μmol) were dried together overnight in vacuo. The compounds were dissolved in dimethylformamide (anhydrous, 500 μL) and dicyclohexylcarbodiimide (10 mg, 48 μmol) was added. The resulting solution was stirred under argon with protection from light for 8 h, whereupon a 110 μL aliquot was added to a solution of oligodeoxynucleotide $2_G$ (87 nmol) in a volume of 350 μL of 0.4M sodium bicarbonate buffer in a 1.6 mL Eppendorf tube. After vortexing briefly, the solution was allowed to stand for 23 h with light protection. The suspension was filtered through 0.45 μm nylon microfilterfuge tubes, and the Eppendorf tube was washed with 250 μL sterile water. The combined filtrates were divided into two Eppendorf tubes, and glycogen (20 mg/mL, 2 μL) and sodium acetate (3M, pH 5.4, 30 μL) were added to each tube. After vortexing, ethanol (absolute, 1 mL) was added to each tube to precipitate the DNA. Ethanol was decanted following centrifugation, and the DNA was washed with an additional 1 mL aliquot of ethanol and allowed to air dry. The pellet was dissolved in 50% formamide gel loading buffer (20 μL), denatured at 90° C. for ca. 2', and loaded on a 20% denaturing polyacrylamide gel. The band corresponding to conjugate $2_H$, n=1, was cut from the gel, crushed, and soaked in 1×TBE buffer (ca. 7 mL) for 1–2 days. The suspension was filtered through nylon filters (0.45 μm) and desalted using a Sep-pak™ reverse phase cartridge. The conjugate was eluted from the cartridge using 40% acetonitrile, lyophilized overnight, and dissolved in 1 mM HEPES buffer, pH 7.0 (500 μL). The solution concentration was determined using UV/vis spectroscopy.

EXAMPLE 4

Figure 2A:
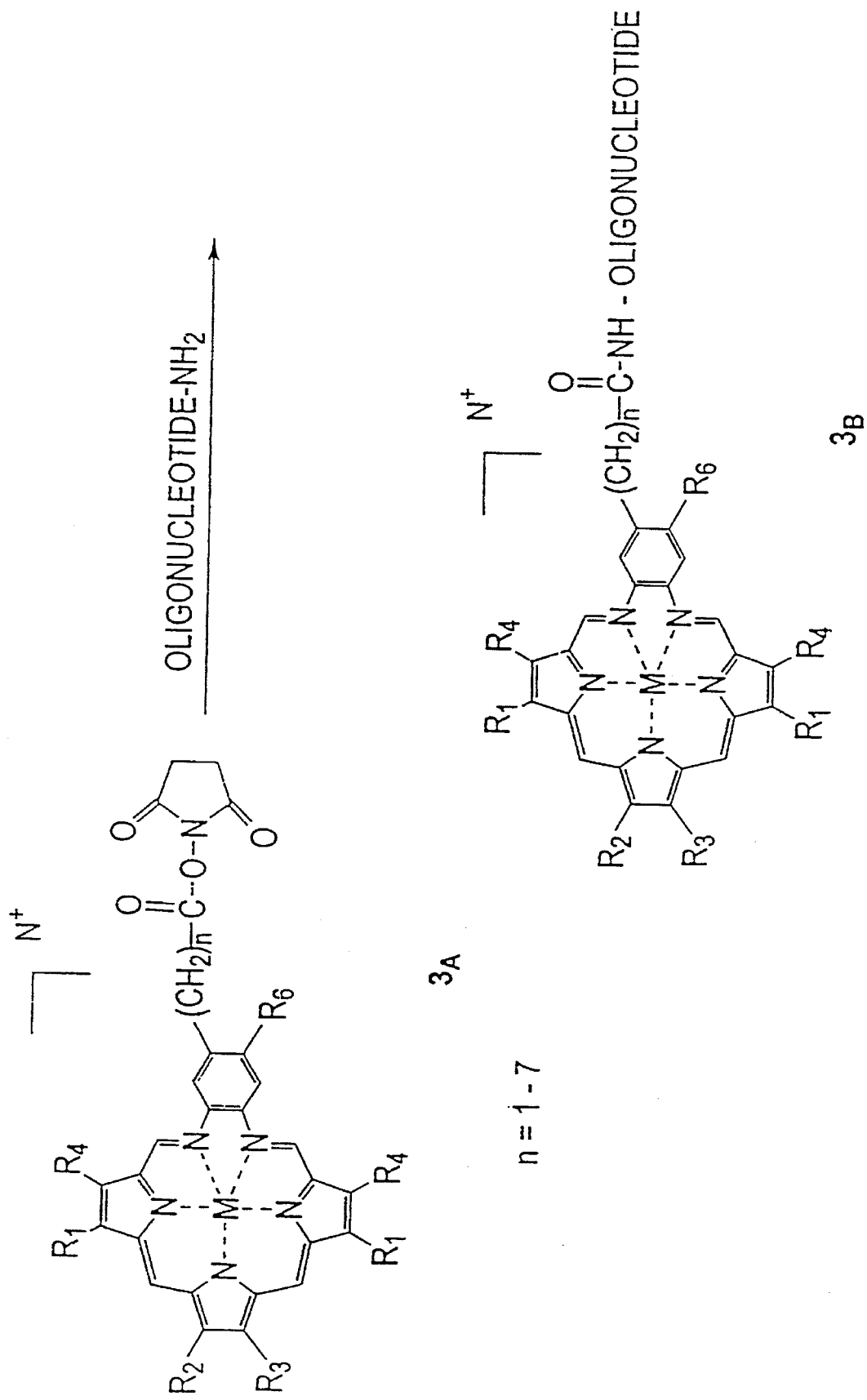
Figure 2B:
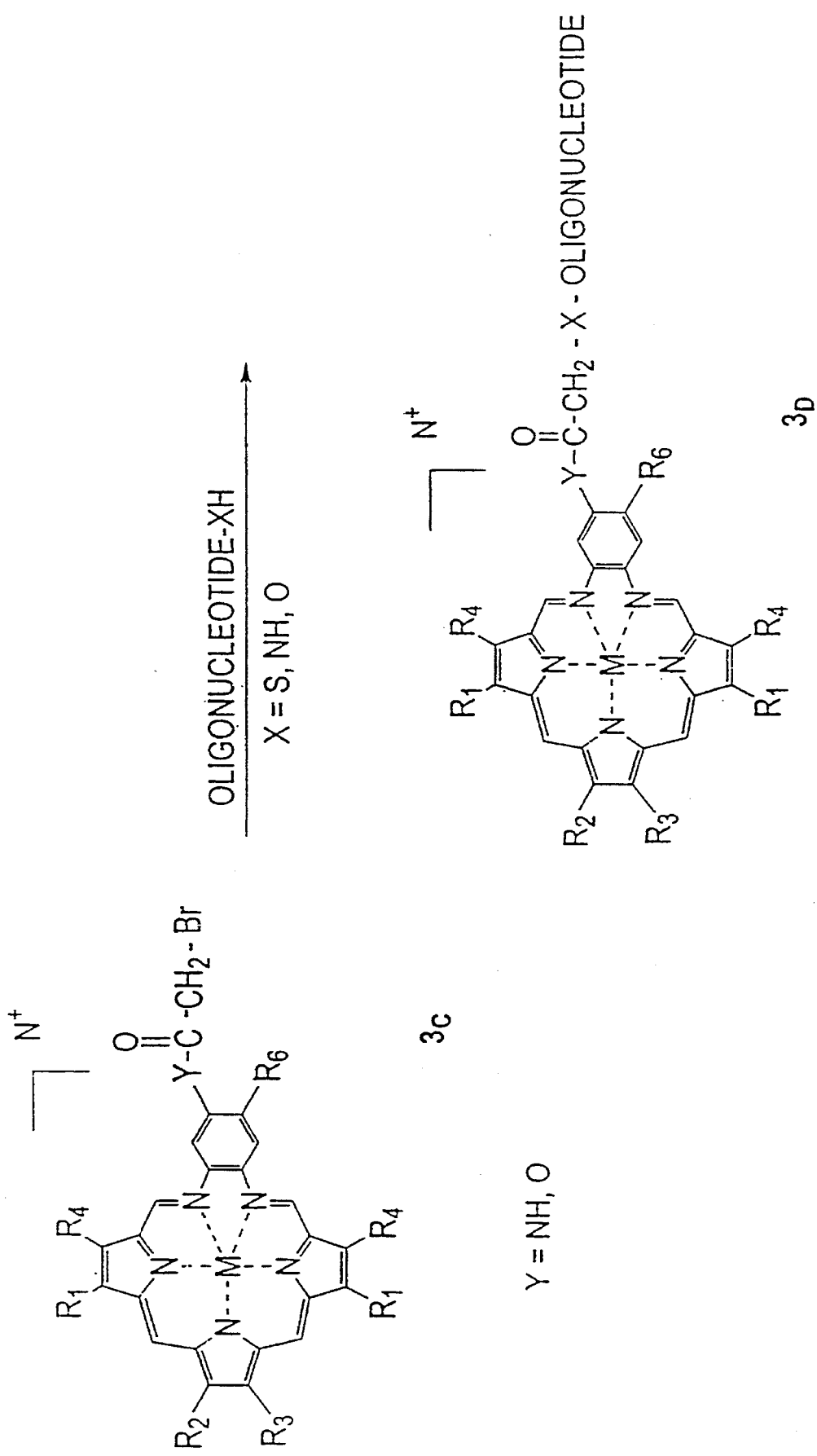
Figure 3A:
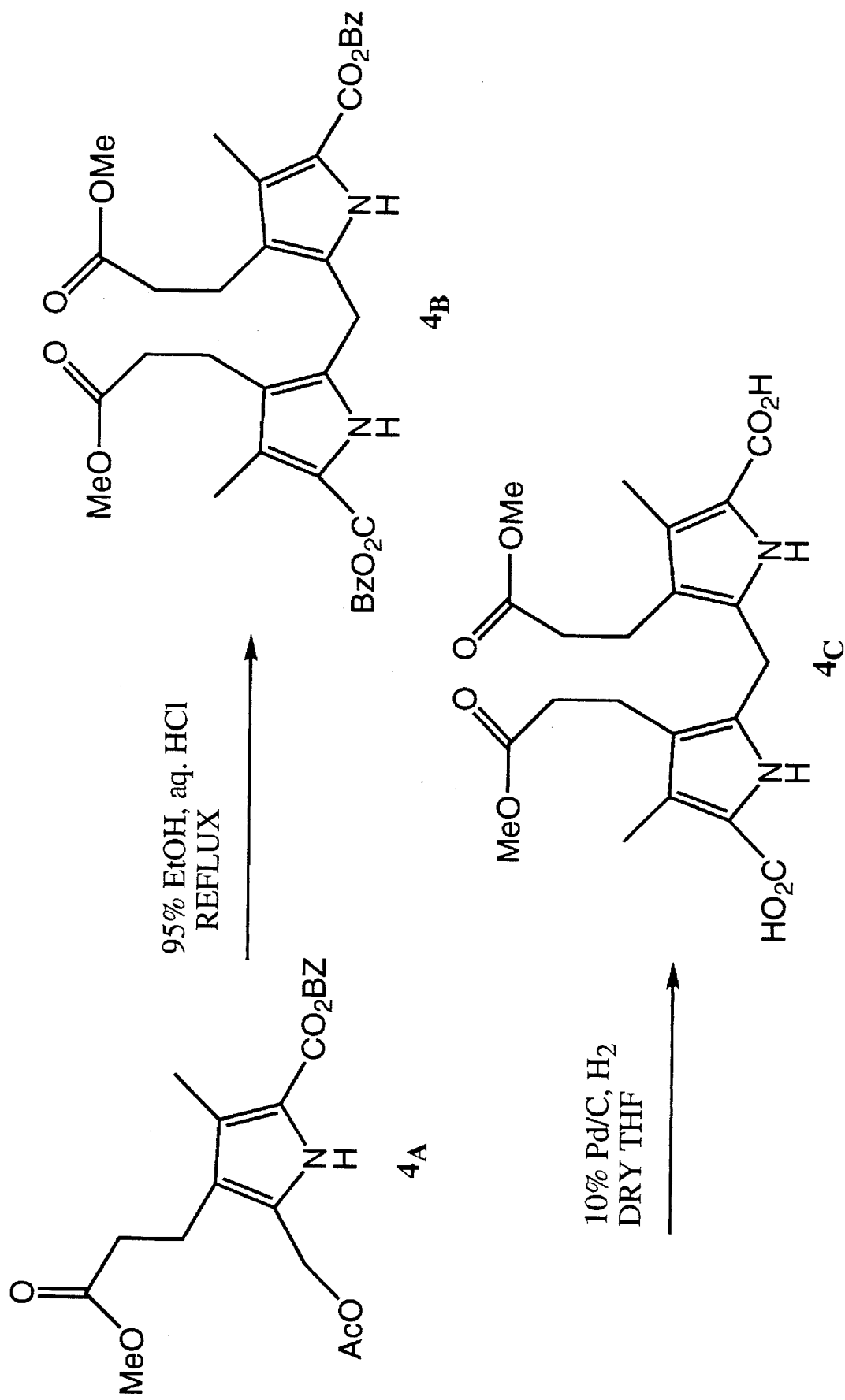
FIG. 3A, FIG. 3B, FIG. 3C, and FIG. 3D demonstrate the synthesis of diformyl monoacid tripyrrane $4_H$ and oligonucleotide conjugate $4_J$.
Figure 3B:
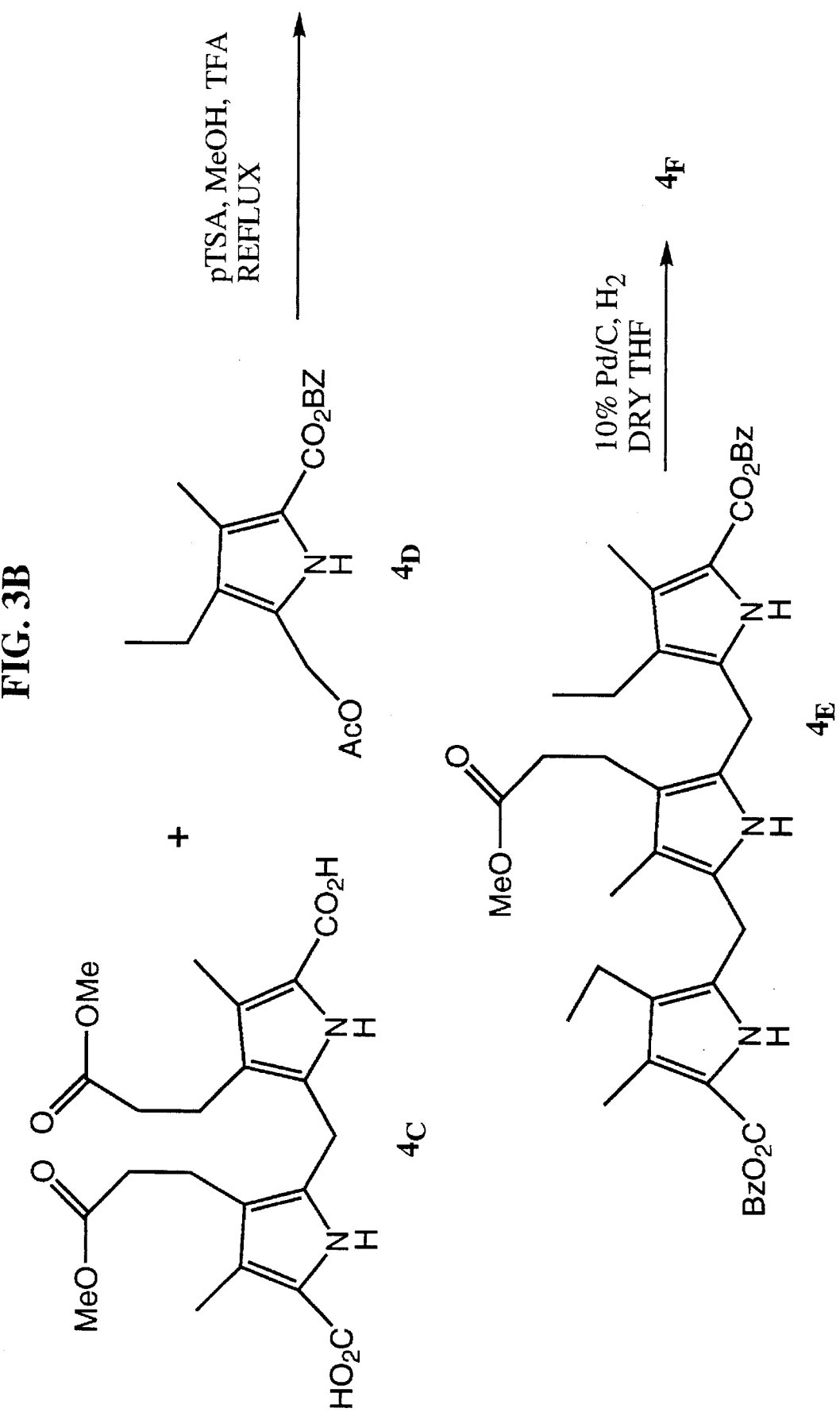
Figure 3C:
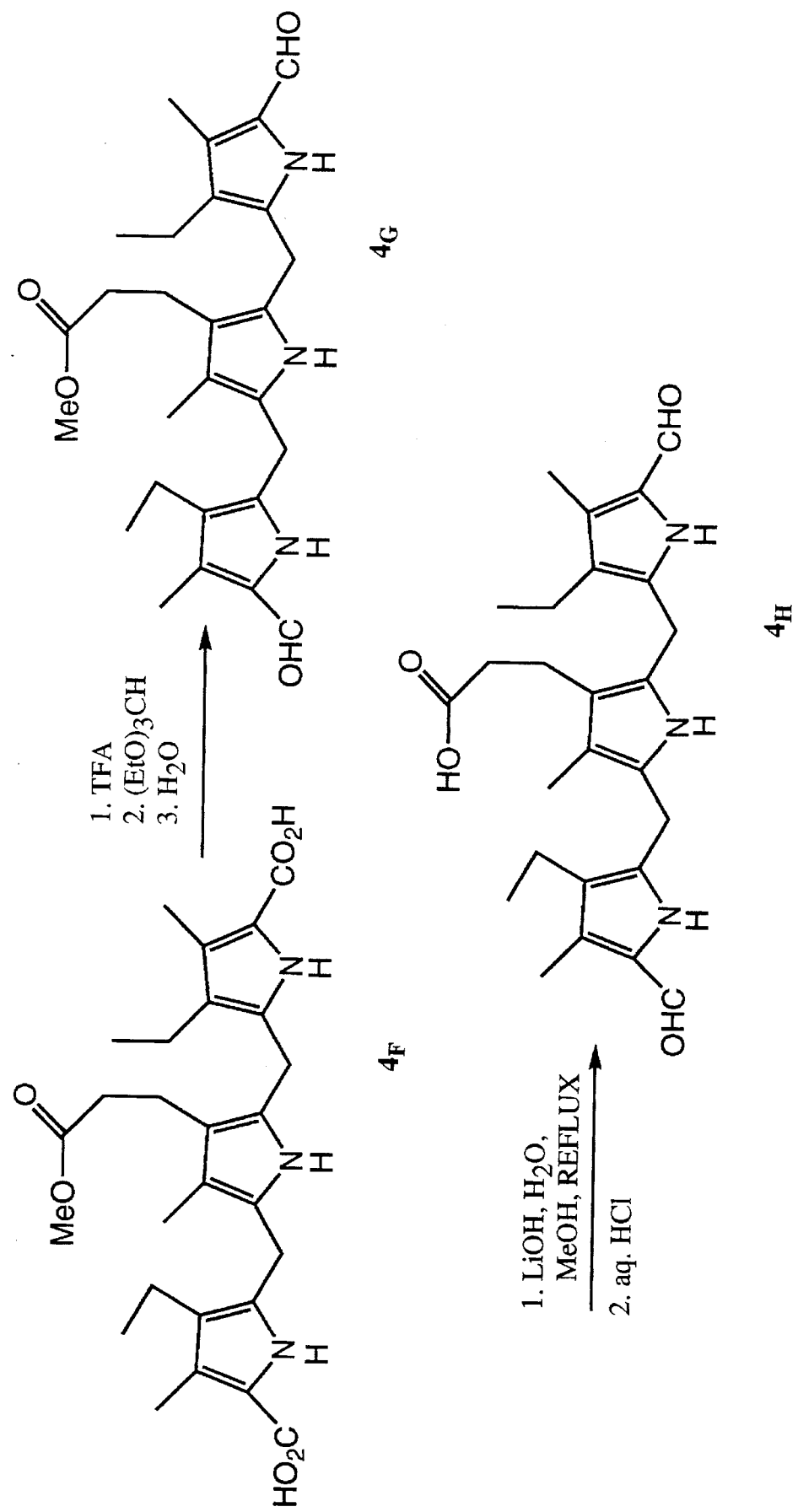
Figure 3D:
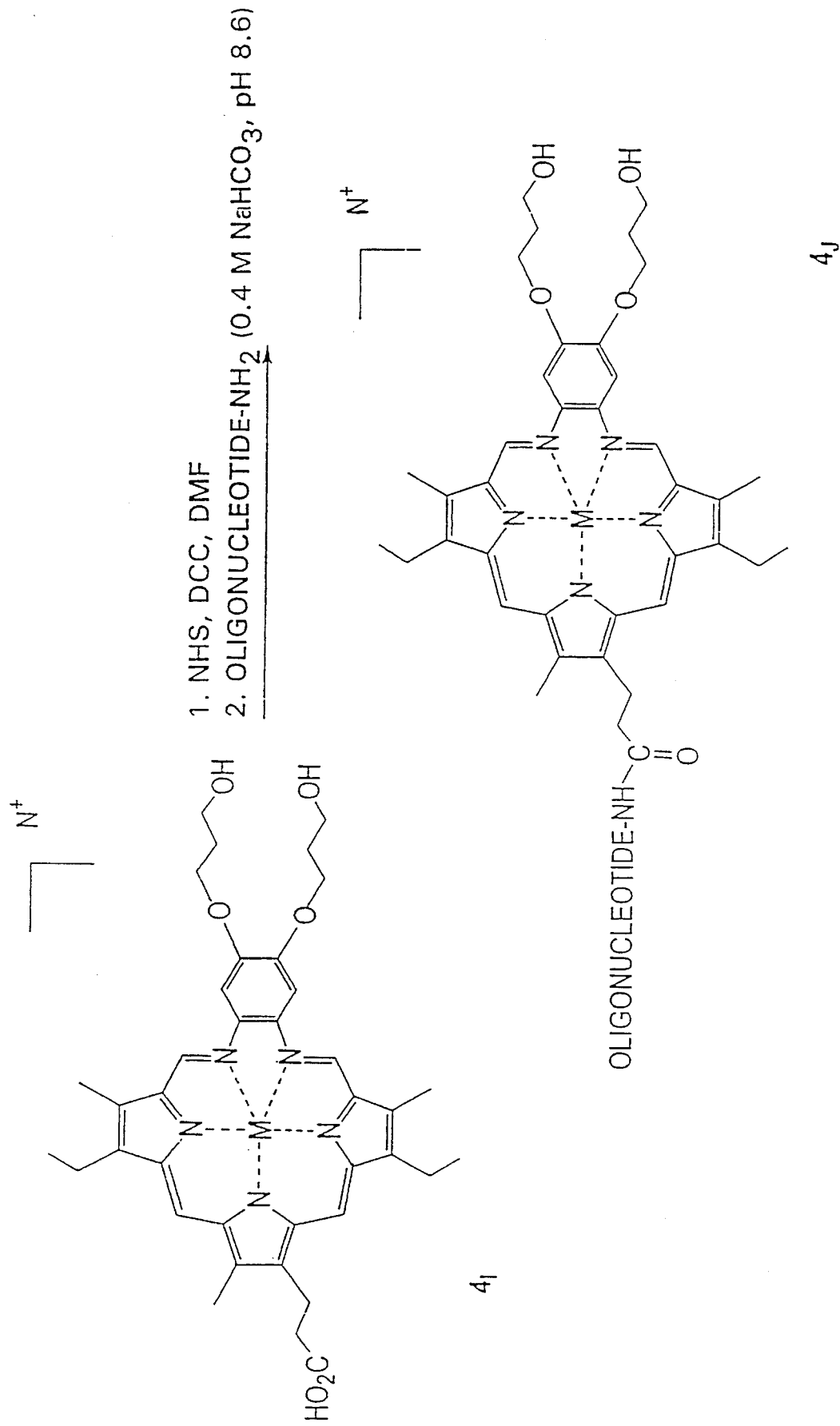

Synthesis of texaphyrin metal complexes with amine-, thiol- or hydroxy-linked oligonucleotides Amides, ethers, and thioethers are representative of linkages which may be used for coupling site-directing molecules such as oligonucleotides to texaphyrin metal complexes (see FIG. 2A, FIG. 2B and FIG. 2C). Oligonucleotides or other site-directing molecules functionalized with amines at the 5'-end, the 3'-end, or internally at sugar or base residues are modified post-synthetically with an activated carboxylic ester derivative of the texaphyrin complex. In the presence of a Lewis acid such as $FeBr_3$, a bromide derivatized texaphyrin (for example, $3_C$ of FIG. 2B) will react with an hydroxyl group of an oligonucleotide to form an ether linkage between the texaphyrin linker and the oligonucleotide. Alternatively, oligonucleotide analogues containing one or more thiophosphate or thiol groups are selectively alkylated at the sulfur atom(s) with an alkyl halide derivative of the texaphyrin complex. Oligodeoxynucleotide-complex conjugates are designed so as to provide optimal catalytic interaction between the targeted DNA phosphodiester backbone and the texaphyrino Oligonucleotides are used to bind selectively compounds which include the complementary nucleotide or oligo- or polynucleotides containing substantially complementary sequences. As used herein, a substantially complementary sequence is one in which the nucleotides generally base pair with the complementary nucleotide and in which there are very few base pair mismatches. The oligonucleotide may be large enough to bind probably at least 9 nucleotides of complementary nucleic acid.

Oligonucleotides are used, for example, as hybridization probes in blot analyses, primers for polymerase chain reaction (PCR) amplification, and for site-specific mutagenesis. Oligonucleotide-derived products are being used for the detection of genetic diseases and for proviral HIV, the causative agent of Acquired Immunodeficiency Syndrome (AIDS). They are also being considered as potential chemotherapeutic agents, for example, in gene therapy, and in an antisense capacity.

For general reviews of synthesis of DNA, RNA, and their analogues, see *Oligonucleotides and Analogues*, F. Eckstein, Ed., 1991, IRL Press, New York; *Oligonucleotide Synthesis*, M. J. Gait, Ed., 1984, IRL Press Oxford, England; Caracciolo et al. (1989); *Bioconjugate Chemistry*, Goodchild, J. (1990); or for phosphonate synthesis, Matteucci, Md. et al., *Nucleic Acids Res.* 14:5399 (1986) (the references are incorporated by reference herein).

In general, there are three commonly used solid phase-based approaches to the synthesis of oligonucleotides containing conventional 5'-3' linkages. These are the phosphoramidite method, the phosphonate method, and the triester method.

A brief description of a current method used commercially to synthesize oligomeric DNA is as follows: Oligomers up to ca. 100 residues in length are prepared on a commercial synthesizer, eg., Applied Biosystems Inc. (ABI) model 392, that uses phosphoramidite chemistry. DNA is synthesized from the 3' to the 5' direction through the sequential addition of highly reactive phosphorous(III) reagents called phosphoramidites. The initial 3' residue is covalently attached to a controlled porosity silica solid support, which greatly facilitates manipulation of the polymer. After each residue is coupled to the growing polymer chain, the phosphorus(III) is oxidized to the more stable phosphorus(V) state by a short treatment with iodine solution. Unreacted residues are capped with acetic anhydride, the 5'-protective group is removed with weak acid, and the cycle may be repeated to add a further residue until the desired DNA polymer is synthesized. The full length polymer is released from the solid support, with concomitant removal of remaining protective groups, by exposure to base. A common protocol uses saturated ethanolic ammonia.

The phosphonate based synthesis is conducted by the reaction of a suitably protected nucleotide containing a phosphonate moiety at a position to be coupled with a solid phase-derivatized nucleotide chain having a free hydroxyl group, in the presence of a suitable activator to obtain a phosphonate ester linkage, which is stable to acid. Thus, the oxidation to the phosphate or thiophosphate can be conducted at any point during synthesis of the oligonucleotide or after synthesis of the oligonucleotide is complete. The phosphonates can also be converted to phosphoramidate derivatives by reaction with a primary or secondary amine in the presence of carbon tetrachloride.

In the triester synthesis, a protected phosphodiester nucleotide is condensed with the free hydroxyl of a growing nucleotide chain derivatized to a solid support in the presence of coupling agent. The reaction yields a protected phosphate linkage which may be treated with an oximate solution to form unprotected oligonucleotide.

To indicate the three approaches generically, the incoming nucleotide is regarded as having an "activated" phosphite/phosphate group. In addition to employing commonly used solid phase synthesis techniques, oligonucleotides may also be synthesized using solution phase methods such as diester synthesis. The methods are workable, but in general, less efficient for oligonucleotides of any substantial length.

Preferred oligonucleotides resistant to in vivo hydrolysis may contain a phosphorothioate substitution at each base (*J. Org. Chem.*, 55:4693–4699, (1990) and Agrawal, (1990)). Oligodeoxynucleotides or their phosphorothioate analogues may be synthesized using an Applied Biosystem 380B DNA synthesizer (Applied Biosystems, Inc., Foster City, Calif.).

EXAMPLE 5

Synthesis of diformyl monoacid tripyrrane $4_H$ and oligonucleotide conjugate $4_J$.

The present example provides for the synthesis of a texaphyrin metal complex-oligonucleotide conjugate where the oligonucleotide is attached to the tripyrrane portion of the molecule (See FIG. 3A, FIG. 3B, FIG. 3C and FIG. 3D).

Dimethylester Dibenzylester Dipyrromethane $4_B$: A three-neck 1000 mL round-bottom flask set with a magnetic stirring bar, a thermometer, a heating mantle, and a reflux condenser attached to an argon line was charged with methylester acetoxypyrrole $4_A$ (100.00 g; 267.8 mmol), 200 proof ethyl alcohol (580 mL), and deionized water (30 mL.) The reaction mixture was heated up and when the resulting solution began to reflux, 12N aq. hydrochloric acid (22 mL) was added all at once. The flask contents were stirred under reflux for two hours. The heating element was replaced by a 0° C. bath and the resulting thick mixture was stirred for two hours prior to placing it in the freezer overnight.

The mixture was filtered over medium fritted glass funnel, pressed with a rubber dam, and washed with hexanes until the filtrate came out colorless. The collected solids were set for overnight high vacuum drying at 30° C. to afford slightly yellowish solids (65.85 g, 214.3 mmol, 80.0% yield.)

Dimethylester Diacid Dipyrromethane, $4_C$: All the glassware was oven dried. A three-neck 2000 mL round-bottom flask set with a magnetic stirring bar, a hydrogen line, and a vacuum line was charged with dimethylester dibenzylester dipyrromethane $4_B$ (33.07 g, 53.80 mmol), anhydrous tetrahydrofuran (1500 mL), and 10% palladium on charcoal (3.15 g.) The flask was filled with dry hydrogen gas after each of several purges of the flask atmosphere prior to stirring the reaction suspension under a hydrogen atmosphere for 24 hours.

The solvent of the reaction suspension was removed under reduced pressure. The resulting solids were dried under high vacuum overnight.

The dry solids were suspended in a mixture of saturated aqueous sodium bicarbonate (1500 mL) and ethyl alcohol (200 mL), and stirred at its boiling point for five minutes. The hot suspension was filtered over celite. The filtrate was cooled down to room temperature and acidified to pH 6 with 12N aqueous hydrochloric acid. The resulting mixture was filtered over medium fritted glass. The collected solids were dried under high vacuum to constant weight (21.63 g, 49.78 mmol, 92.5% yield.)

Methylester Dibenzylester Tripyrrane, $4_E$ A three-neck 2000 mL round-bottom flask set with a heating mantle, a magnetic stirring bar, a thermometer, and a reflux condenser attached to an argon line was charged with dimethylester diacid dipyrromethane $4_C$ (21.00 g, 48.33 mmol), ethyl acetoxy pyrrole $4_D$ (30.50 g), p-toluenesulfonic acid monohydrate (1.94 g), trifluoroacetic acid (39 mL), and methyl alcohol (1350 mL.) The flask contents were heated and stirred under reflux for two hours. The heating element was replaced with a 0° C. and the stirring was continued for half an hour prior to placing the resulting mixture in a freezer overnight.

The cold mixture was filtered over medium fritted glass. The collected solids were washed with hexanes and dried under high vacuum overnight (13.05 g, 19.25 mmol, 39.8% yield.)

Methylester Diacid Tripyrrane $4_F$: All the glassware was oven dried. A three-neck 500 mL round-bottom flask set with a magnetic stirring bar, a hydrogen line, and a vacuum line was charged with methylester dibenzylester tripyrrane $4_E$ (12.97 g, 19.13 mmol), anhydrous tetrahydrofuran (365 mL), and 10% palladium on charcoal (1.13 g.) The flask was filled with dry hydrogen gas after each of several purges of the flask atmosphere prior to stirring the reaction suspension for 24 hours under a hydrogen atmosphere at room temperature.

The reaction suspension was filtered over celite. The solvent of the filtrate was removed under reduced pressure to obtain a foam which was dried under high vacuum overnight (10.94 g, 21.99 mmol, 87.0% pure.)

Monoacid Tripyrrane $4_H$: All the glassware was oven dried. A three-neck 500 mL round-bottom flask set with a mechanical stirrer, a thermometer, a 0° C. bath, and an addition funnel set with an argon line was charged with methylester diacid tripyrrane $4_F$ (10.20 g, 17.83 mmol). Trifluoroacetic acid (32.5 mL) was dripped into the reaction flask from the addition funnel over a 45 minute period keeping the flask contents below 5° C. The resulting reaction solution was stirred at 0° C. for 15 minutes, and then at 20° C. for three hours. Triethylorthoformate (32.5 mL) was dripped into the flask from the addition funnel over a 20 minute period keeping the flask contents below −25° C. by means of a dry ice/ethylene glycol bath. The reaction solution was stirred for one hour at −25° C. and then a 0° C. bath was set up. Deionized water (32.5 mL) was dripped into the reaction flask from the addition funnel keeping the flask contents below 10° C. The resulting two phase mixture was stirred at room temperature for 75 minutes and then added 1-butanol (200 mL.) The solvents were removed under reduced pressure. The resulting dark oil was dried under high vacuum overnight to obtain black solids (11.64 g.)

A three-neck 2000 mL round-bottom flask set with a thermometer, a heating mantle, a magnetic stirring bar, and a reflux condenser attached to an argon line, was charged with the crude methylester diformyl tripyrrane $4_G$ (11.64 g), methyl alcohol (900 mL), deionized water (60 mL), and lithium hydroxide monohydrate (4.7 g.) The flask contents were heated, stirred under reflux for two hours, cooled down to room temperature, added deionized water (250 mL), acidified with 12N aq. HCl to pH 5, and then stirred at 0° C. for one hour. The resulting mixture was filtered over medium fritted glass funnel. The collected solids were dried under high vacuum to constant weight prior to their purification by column chromatography (silica gel, MeOH in $CH_2Cl_2$, 0–10%; 3.64 g, 8.06 mmol, 45.2% yield.)

The monoacid tripyrrane $4_H$ is condensed with a derivatized ortho-phenylene diamine, for example, $1_G$ to form a nonaromatic precursor which is then oxidized to an aromatic metal complex, for example, $4_I$. An oligonucleotide amine may be reacted with the carboxylic acid derivatized texaphyrin $4_I$ to form the conjugate $4_J$ having the site-directing molecule on the T (tripyrrane) portion of the molecule rather than the B (benzene) portion.

EXAMPLE 6

Figure 4:
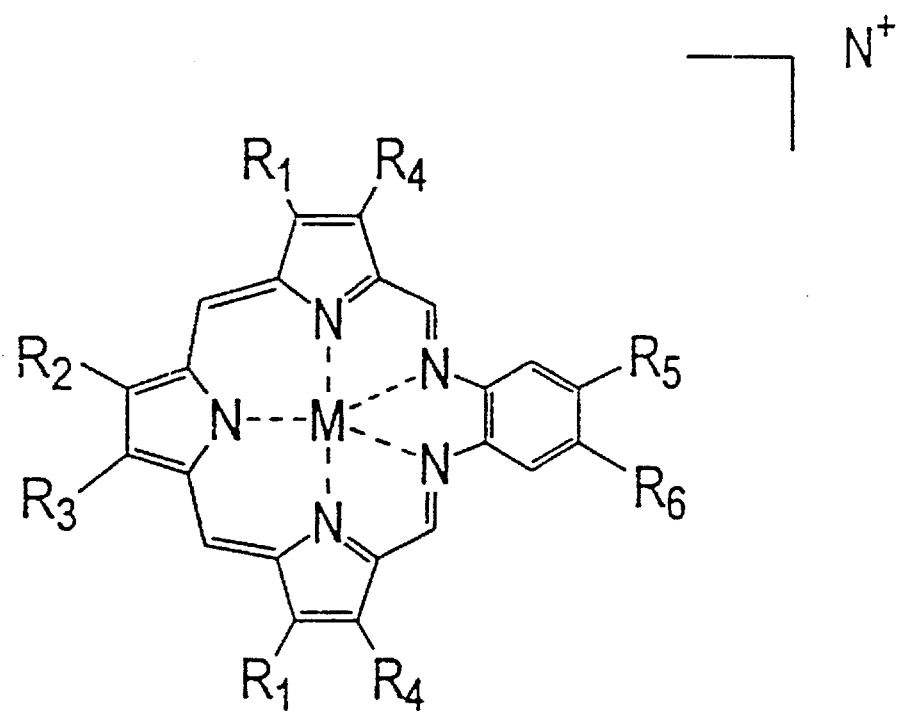
FIG. 4 shows texaphyrin-metal complexes useful for the present invention.

Synthesis of Texaphyrin-Oligonucleotide Conjugates having a Texaphyrin Attached to the 3' end Two oligodeoxyribonucleotides of 12 bases each were synthesized to contain alkylamine groups at the 3' terminal phosphate (Keystone Labs, Menlo Park, Calif.). Oligonucleotides were HPLC purified and precipitated using LiCl prior to use. Reaction of a carboxylic acid functionalized metal texaphyrin complex $5_B$ (FIG. 4), such as the Lu(III)texaphyrin complex, with carbodiimide and N-hydroxysuccinimide produced the corresponding activated ester, which was added directly to a solution of the chosen oligodeoxynucleotide amine. The resulting txp-metal complex-oligonucleotide conjugates were purified by electrophoresis.

These 3'-conjugates may be of particular importance in certain embodiments of the present invention, since attachment of large groups (such as the present texaphyrin complexes) to the 3' end of oligonucleotides renders the oligonucleotide resistant to cellular exonucleases.

In a similar manner, an embodiment of the present invention is the addition of particular ligands to the 3' end of an oligonucleotide having its 5' end conjugated to a texaphyrin. The function of the 3' ligand is to aid in the uptake of the conjugate into the cell. Such ligands are known in the art and include, but are not limited to, cholesterol and polylysine.

A further embodiment of the present invention in the cleavage of DNA using texaphyrin metal complex-oligonucleotide conjugates is the use of a set of two conjugates, one having the texaphyrin metal complex conjugated to the 5' end of an oligomer and the other having a texaphyrin metal complex conjugated to the 3' end of an oligomer and the oligomers are complementary to the same DNA substrate, one just upstream from the other, so as to position both texaphyrin metal complexes in proximity to the targeted cleavage site. The distance separating the two catalytic groups may be varied by preparing a nested set of oligomer-5'-conjugates of varying lengths and comparing the cleavage efficiencies that result upon the simultaneous binding of the two conjugates to the DNA template.

EXAMPLE 7

Synthesis of a Texaphyrin Metal Complex-Oligonucleotide Dual Conjugate

An oligodeoxyribonucleotide having 12 bases was synthesized to contain alkylamine groups at both the 3' and the 5' ends (Keystone Labs, Menlo Park, Calif.). This oligomer was reacted with an excess of a carboxylic acid functionalized metal-texaphyrin complex $5_B$, following the procedures of Example 6, to give a dual conjugate having a texaphyrin-metal complex at both the 3'- and the 5'-ends of the 12-mer.

The use of two texaphyrin-metal complexes conjugated to the same oligonucleotide, one at each end, should effect the cleavage of DNA with increased efficiency due to the concerted activity of the metal complexes. In this embodiment, it is preferred that both of the texaphyrin complexes contain the same metal, preferably a diamagnetic metal cation and more preferably lutetium(III).

Further, a dual conjugate provides versatility in the functions that may be accomplished by this one molecule. For example, the oligonucleotide provides binding specificity, one texaphyrin metal complex may provide for imaging (having Gd(III) as the metal ion, for example) while the other provides for DNA cleavage. Such a dual conjugate allows for 2 functions, imaging and cleavage, to be effected by one molecule.

EXAMPLE 8

Synthesis of Texaphyrin T2BET Metal Complexes

The synthesis of texaphyrins is provided in U.S. Pat. Nos. 4,935,498, 5,162,509 and 5,252,720, all incorporated by reference herein. The present example provides the synthesis of a preferred texaphyrin, named T2BET, having substituents containing ethoxy groups.

Lutetium(III) acetate hydrate was purchased from Strem Chemicals, Inc. (Newburyport, Mass.) and gadolinium(III) acetate tetrahydrate was from Aesar/Johnson Matthey (Ward Hill, Mass.). The LZY-54 zeolite was purchased from UOP (Des Plaines, Ill.). Acetone, glacial acetic acid, methanol, ethanol, isopropyl alcohol, and n-heptanes were purchased from J. T. Baker (Phillipsburg, N.J.). Triethylamine and Amberlite 904 anion exchange resin were purchased from Aldrich (Milwaukee, Wisc.). All chemicals were ACS grade and used without further purification.

Figure 5A:
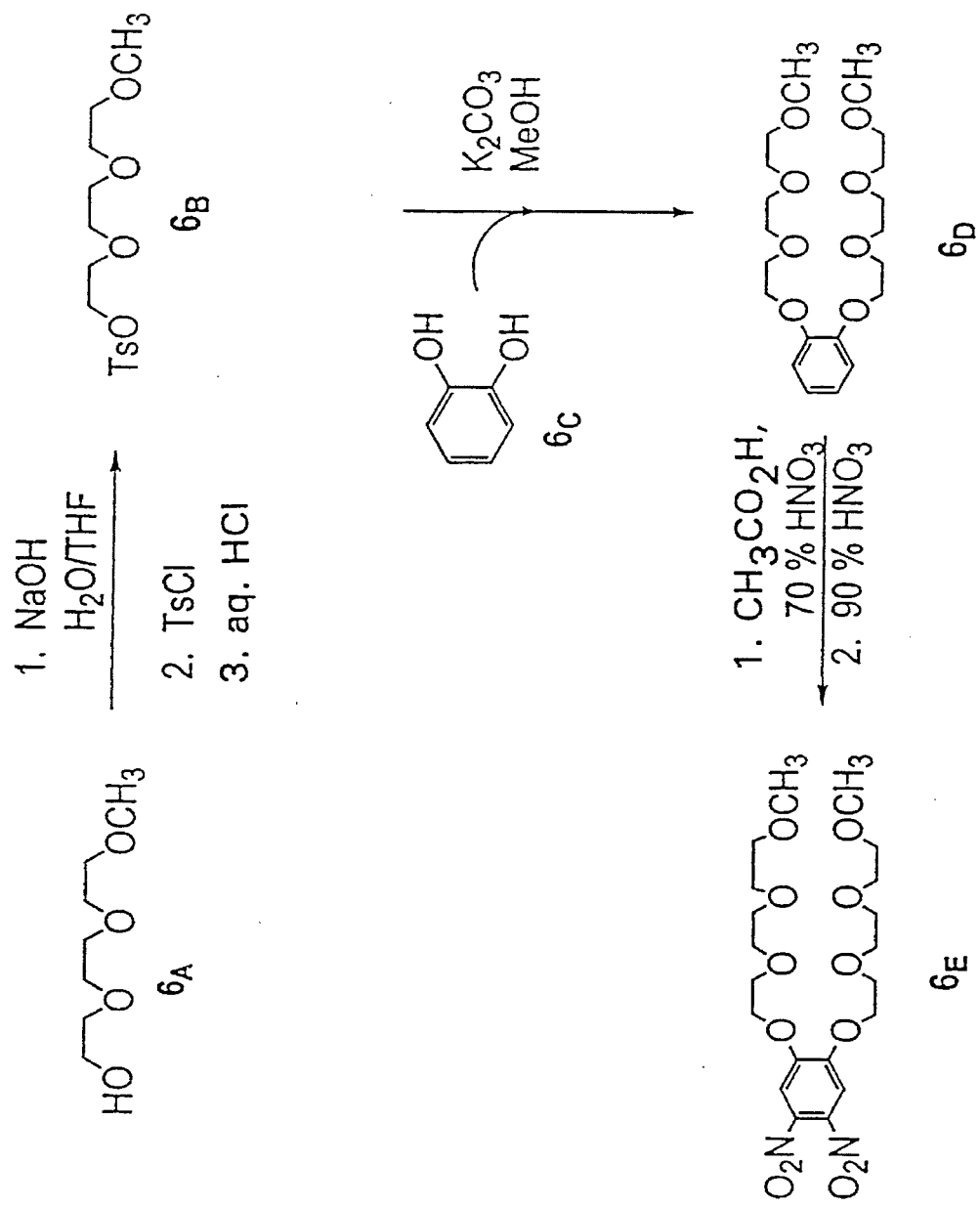
FIG. 5A, FIG. 5B and FIG. 5C show the synthesis of a preferred texaphyrin of the present invention, T2BET.
Figure 5B:
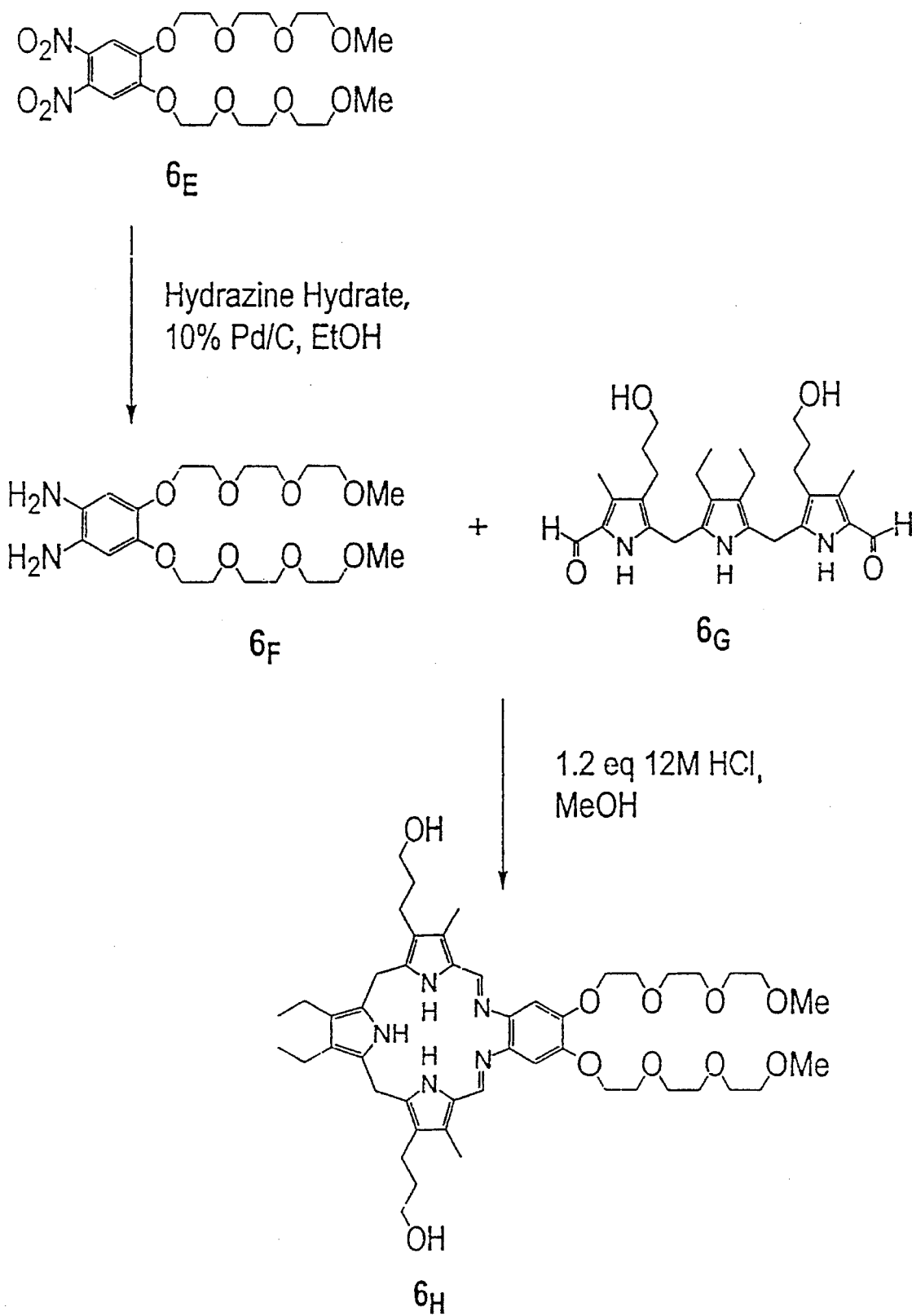
Figure 5C:
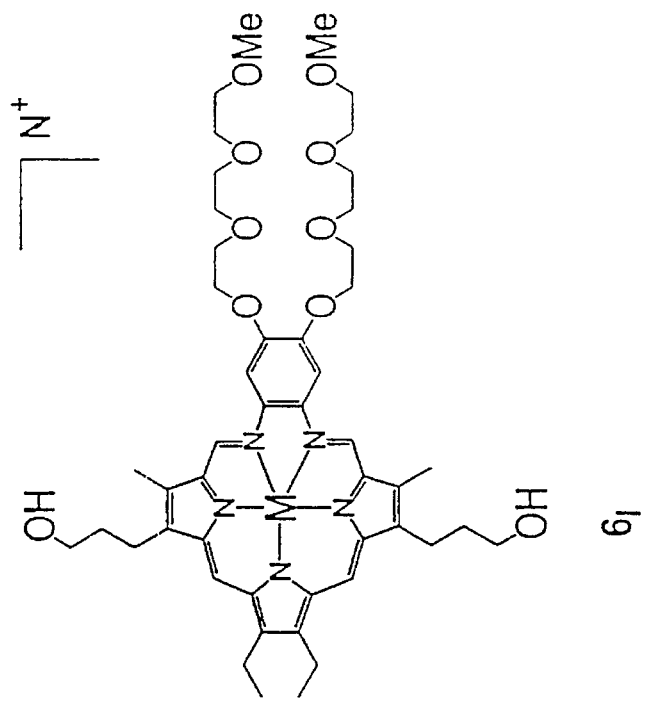
Figure 5C:
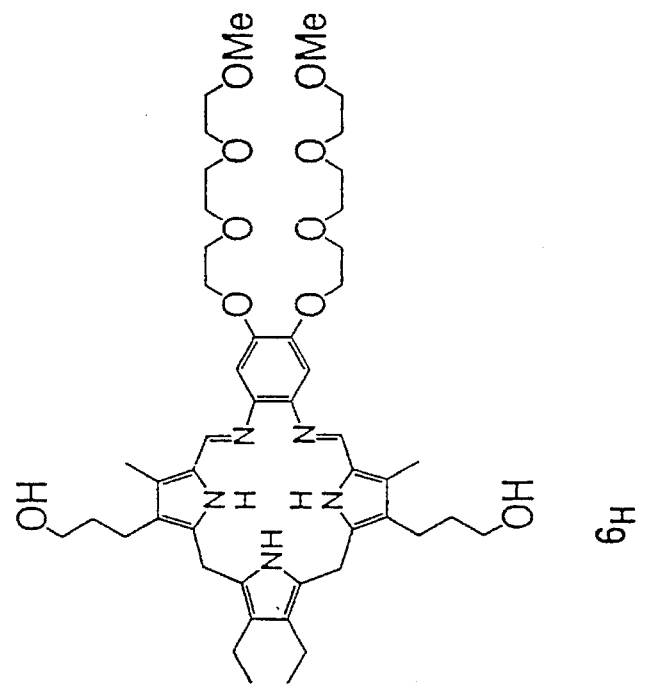

Synthesis of the gadolinium (III) complex of 4,5-diethyl-10,23-dimethyl-9,24-bis(3-hydroxypropyl)-16,17-bis[2-[2-(2-methoxyethoxy)ethoxy]ethoxy]-pentaazapentacyclo [20.2.1.1$^{3,6}$.1$^{8,11}$.0$^{14,19}$]heptacosa-1,3,5,7,9,11(27),12,14,16,18,20,22(25),23-tridecaene ($6_F$, FIG. 5A, FIG. 5B AND FIG. 5C). The critical intermediate 1,2-bis[2-[2-(2-methoxyethoxy)ethoxy)ethoxy]-4,5-dinitrobenzene, $6_E$ was prepared according to the three-step synthetic process outlined in FIG. 5A.

Synthesis of triethylene glycol monomethyl ether monotosylate, $6_B$: In an oven dried 12 L three-necked round-bottom flask, equipped with a magnetic stir bar and a 1000 mL pressure-equalizing dropping funnel, a solution of NaOH (440.0 g, 11.0 mol) in water (1800 mL) was added, and the mixture was cooled to 0° C. A solution of triethylene glycol monomethyl ether $6_A$ (656.84 g, 4.0 mol) in THF (1000 mL) was added. The clear solution was stirred vigorously at 0° C. for 15 min and a solution of tosyl chloride (915.12, 4.8 mol) in THF (2.0 L) was added dropwise over a 1 h period. The reaction mixture was stirred for an additional 1 h at 0° C., and 10% HCl (5.0 L) was added to quench the reaction (to pH 5–7). The two-phase mixture was transferred to a 4 L separatory funnel, the organic layer removed, and the aqueous layer extracted with t-butylmethyl ether (3×250 mL). The combined organic extracts were washed with brine (2×350 mL), dried (MgSO$_4$), and evaporated under reduced pressure to afford $6_B$, 1217.6 g (95%) as a light colored oil. This material was taken to the next step without further purification.

Synthesis of 1,2-bis[2-[2-(2-methoxyethoxy)ethoxy] ethoxy]benzene $6_D$. In a dry 5 L round-bottom flask equipped with an overhead stirrer, reflux condenser, and a gas line, K$_2$CO$_3$ (439.47 g, 3.18 mol) and MeOH (1800 mL) were combined under an argon atmosphere. To this well-stirred suspension, catechol $6_C$ (140.24 g, 1.27 mol) was added, and the mixture was heated to reflux. $6_B$ (1012.68 g, 3.18 mol) was then added in one portion. The suspension was stirred at reflux for 24 h, cooled to room temperature, and filtered through Celite. The pad was rinsed with 500 mL of methanol and the combined filtrates were evaporated under reduced pressure. The resulting brown residue was taken up in 10% NaOH (800 mL), and methylene chloride (800 mL) was added with stirring. The mixture was transferred to a 2 L separatory funnel, the organic layer removed and the aqueous layer extracted with methylene chloride (3×350 mL). The organic extracts were combined, washed with brine (350 mL), dried ($MgSO_4$), evaporated under reduced pressure, and the residue dried in vacuo for several hours to yield 485.6 g (95%) of 1,2-bis[2-[ 2-(2-methoxyethoxy)ethoxy]ethoxy]benzene $6_D$. For $6_D$: bp. 165°–220° C., (0.2–0.5 mm Hg); FAB MS, $M^+$: m/e 402; HRMS, $M^+$: 402.2258 (calcd. for $C_{20}H_{34}O_8$, 402.2253).

Synthesis of 1,2-bis[2-[2-(2-methoxyethoxy)ethoxy]ethoxy]- 4,5-dinitrobenzene $6_E$. In an oven dried 1 L round-bottom flask, $6_D$ (104 g, 0.26 mol) and glacial acetic acid (120 mL) were combined and cooled to 5° C. To this well stirred solution, concentrated nitric acid (80 mL) was added dropwise over 15–20 min. The temperature of the mixture was held below 40° C. by cooling and proper regulation of the rate of addition of the acid. After addition the reaction was allowed to stir for an additional 10–15 min and was then cooled to 0° C. Fuming nitric acid (260 mL) was added dropwise over 30 min while the temperature of the solution was held below 30° C. After the addition was complete, the red colored solution was allowed to stir at room temperature until the reaction was complete (ca. 5 h, TLC: 95/5; $CH_2Cl_2$/MeOH) and then poured into well stirred ice water (1500 mL). Methylene chloride (400 mL) was added, the two-phase mixture was transferred to a 2 L separatory funnel and the organic layer was removed. The aqueous layer was extracted with $CH_2Cl_2$(2×150 mL) and the combined organic extracts were washed with 10% NaOH (2×250 mL) and brine (250 mL), dried ($MgSO_4$), and concentrated under reduced pressure. The resulting orange oil was dissolved in acetone (100 mL), and the solution layered with n-hexanes (500 mL), and stored in the freezer. The resulting precipitate was collected by filtration yield 101.69 g (80%) of $6_E$, as a yellow solid. For $6_E$: mp 43°–45° C.; FAB MS, $(M+H)^+$: m/e 493; HRMS, $(M+H)^+$: 493.2030 (calcd. for $C_{20}H_{33}N_2O_{12}$, 493.2033).

Synthesis of 1,2-diamino-4,5-bis[2-[2-(2-methoxyethoxy)ethoxy]ethoxy]benzene, $6_F$, FIG. 5B. In an oven dried 500 mL round bottom flask, equipped with a Claisen adapter, pressure equalizing dropping funnel, and reflux condenser, 1,2-bis[2-[2-( 2-methoxyethoxy)ethoxy]ethoxy] -4,5-dinitrobenzene $6_E$ (20 g, 0.04 mol) was dissolved in absolute ethanol (200 mL). To this clear solution, 10% palladium on carbon (4 g) was added and the dark black suspension was heated to reflux under an argon atmosphere. Hydrazine hydrate (20 mL) in EtOH (20 mL) was added dropwise over 10 min to avoid bumping. The resulting brown suspension was heated at reflux for 1.5 h at which time the reaction mixture was colorless and TLC analysis (95/5; $CH_2Cl_2$/MeOH) displayed a low $R_f$ UV active spot corresponding to the diamine. Therefore, the mixture was hot filtered through Celite and the pad rinsed with absolute ethanol (50 mL). The solvent was removed under reduced pressure and the resulting light brown oil was dried in vacuo (in the dark) for 24 h to yield 15.55 g (89%) of 1,2-diamino-bis[2-[2-(2-methoxyethoxy)ethoxy]ethoxy]benzene $6_F$. For $6_F$: FAB MS, $M^+$: m/e 432; HRMS, $M^+$: 432.2471 (calcd. for $C_{20}H_{36}N_2O_8$, 432.2482). This material was taken to the next step without further purification.

Synthesis of 4,5-diethyl-10,23-dimethyl-9,24-bis(3-hydroxypropyl)- 16,17-bis[2-[2-(2-methoxyethoxy)ethoxy] ethoxy]- 13,20,25,26,27-pentaazapentacyclo[20.2.1.1$^{3,6}$.1$^{8,11}$.0$^{14,19}$] heptacosa-3,5,8,10,12,14,16,18,20,22,24-undecaene ($6_H$). In an oven dried 1 L round-bottom flask, 2,5-bis[(5-formyl-3-(3-hydroxypropyl)- 4-methyl-pyrrol-2-yl)methyl]-3,4-diethylpyrrole $6_G$ (The synthesis of $6_G$ is provided in U.S. Pat. No. 5,252,720, incorporated by reference herein.) (30.94 g, 0.0644 mol) and 4,5-diamino-bis[2-[2-(2-methoxyethoxy)ethoxy]ethoxy]benzene $6_F$ (28.79 g, 0.0644 mol) were combined in absolute methanol (600 mL) under an argon atmosphere. To this well stirred suspension, a mixture of concentrated hydrochloric acid (6.7 mL) in absolute methanol (200 mL) was added in one portion. The mixture was gradually heated to 50° C., at which time the reaction went from a cloudy suspension of starting materials to a dark red homogeneous solution as the reaction proceeded. After 3 h the reaction was judged complete by TLC analysis and UV/visible spectroscopy ($\lambda_{max}$ 369 nm). The reaction mixture was cooled to room temperature, 60 g of activated carbon (DARCO™) was added, and the resulting suspension was stirred for 20 min. The dark suspension was filtered through Celite to remove the carbon, the solvent evaporated to dryness, and the crude $6_H$ dried in vacuo overnight. $6_H$ was recrystallized from isopropyl alcohol/n-heptane to afford 50 g (85%) of a scarlet red solid. For $6_H$: $^1$H NMR ($CD_3OD$): δ 1.11 (t, 6H, $CH_2CH_3$), 1.76 (p, 4H, pyrr-$CH_2CH_2CH_2OH$), 2.36 (s, 6H, pyrr-$CH_3$), 2.46 (q, 4H, $CH_2CH_3$), 2.64 (t, 4H, pyrr-CH $_2CH_2CH_2OH$), 3.29 [s, 6H, ($CH_2CH_2O)_3CH_3$], 3.31 (t, 4H, pyrr-CH $_2CH_2CH_2OH$), 3.43–3.85 (m, 20H, $CH_2CH_2OCH_2CH_2OCH_2CH_2O$), 4.0 (s, 4H, (pyrr)$_2$-$CH_2$), 4.22 (t, 4H, $PhOCH_2CH_2O$), 7.45 (s, 2H, PhH), 8.36 (s, 2H, HC=N); UV/vis: [(MeOH) $\lambda_{max}$, nm]: 369; FAB MS, $[M+H]^+$: m/e 878.5; HRMS, $[M+H]^+$: m/e 878.5274 (calcd. for $[C_{48}H_{72}N_5O_{10}]^+$, 878.5279).

Synthesis of the gadolinium (III) complex of 4,5-diethyl-10,23-dimethyl-9,24-bis(3-hydroxypropyl)-16,17-bis[2-[2-(2-methoxyethoxy)ethoxy]ethoxy]pentaazapentacyclo [20.2.1.1$^{3,6}$.1$^{8,11}$.0$^{14,19}$]heptacosa- 1,3,5,7,9,11(27),12,14,16,18,20,22(25),23-tridecaene $6_I$. $6_I$ was prepared according to the process outlined in FIG. 5C. In a dry 2 L three-necked round-bottom flask, $6_H$ (33.0 g, 0.036 mol) and gadolinium(III) acetate tetrahydrate (15.4 g, 0.038 mol) were combined in methanol (825 mL). To this well stirred red solution, gadolinium(III) acetate tetrahydrate (15.4 g, 0.038 mol) and triethylamine (50 mL) were added and the reaction was heated to reflux. After 1.5 h, air was bubbled (i.e., at reflux) for 4 h into the dark green reaction solution with aid of a gas dispersion tube (flow rate=20 cm$^3$/min). At this point, the reaction mixture was carefully monitored by UV/Visible spectroscopy (i.e., a spectrum is taken every 0.5–1 h, ~1 drop diluted in 4–5 mL MeOH). The reaction was deemed complete by UV/Vis (In MeOH ratio: 342 nm/472 nm=0.22–0.24) after 4 h. The dark green reaction was cooled to room temperature, filtered through Celite into a 2 L round-bottom flask, and the solvent removed under reduced pressure. The dark green solid was suspended in acetone (1 L) and the resulting slurry was stirred for 1 h at room temperature. The suspension was filtered to remove the red/brown impurities (incomplete oxidation products), the solids rinsed with acetone (200 mL), and air dried. The crude complex (35 g) was dissolved in MeOH (600 mL), stirred vigorously for 15 min, filtered through Celite, and transferred to a 2 L Erlenmeyer flask. An additional 300 mL of MeOH and 90 mL water were added to the flask, along with acetic acid washed LZY-54 zeolite (150 g). The suspension was agitated with an overhead mechanical stirrer for approximately 3–4 h. The zeolite extraction is deemed complete with the absence of free Gd(III). [To test for free gadolinium, the crude $6_I$ was spotted heavily onto a reverse phase TLC plate (Whatman KC8F, 1.5×10 cm) and the chromatogram developed using 10% acetic acid in methanol. The green complex moved up the TLC plate close to the solvent front. Any free gadolinium metal will remain at the origin under these conditions. After developing the chromatogram, the plate was dried and the lower ¼ of the plate stained with an Arsenazo III solution in methanol (4 mg Arsenazo III in 10 mL methanol). A very faint blue spot (indicative of free metal) was observed at the origin against a pink background indicating very little free gadolinium metal.] The zeolite was removed through a Whatman #3 filter paper and the collected solids rinsed with MeOH (200 mL). The dark green filtrate was loaded onto a column of Amberlite IRA-904 anion exchange resin (30 cm length×2.5 cm diameter) and eluted through the resin (ca. 10 mL/min flow rate) into a 2 L round bottom flask with 300 mL 1-butanol. The resin was rinsed with an additional 100 mL of MeOH and the combined eluent evaporated to dryness under reduced pressure. The green shiny solid $6_I$ was dried in vacuo for several hours at 40° C. To a well stirred ethanoic solution (260 mL) of $6_I$ at 55°–60° C., n-heptanes (ca. 600 mL) was added dropwise (flow=4 mL/min) from a 1 L pressure-equalizing dropping funnel. During the course of 1.5 h (300 mL addition) the green complex, $6_I$ began to crystallize out of the dark mixture. After complete addition, the green suspension was cooled and stirred for 1 h at room temperature. The suspension was filtered, the solids rinsed with acetone (250 mL), and dried in vacuo for 24 h to afford 26 g (63%). UV/vis: [(MeOH) $\lambda_{max}$, nm]: 316, 350, 415, 473, 739; FAB MS, (M–20 Ac)$^+$: m/e 1030; HRMS, (M–20 Ac)$^+$: m/e 1027.4036 (calcd. for $C_{48}H_{66}{}^{155}GdN_5O_{10}$, 1027.4016). Anal. calcd. for $[C_{52}H_{72}GdN_5O_{14}]\cdot 0.5H_2O$: C, 53.96; H, 6.36; N, 6.05, Gd, 13.59. Found: C, 53.73; H, 6.26; N, 5.82; Gd, 13.92.

Synthesis of the Lutetium(III) Complex of $6_H$. The macrocyclic ligand $6_H$ was oxidatively metallated using lutetium(III) acetate hydrate (9.75 g, 0.0230 mol) and triethylamine (22 mL) in air-saturated methanol (1500 mL) at reflux.[1] After completion of the reaction (as judged by the optical spectrum of the reaction mixture), the deep green solution was cooled to room temperature, filtered through a pad of celite, and the solvent removed under reduced pressure. The dark green solid was suspended in acetone (600 mL), stirred for 30 min at room temperature, and then filtered to wash away the red/brown impurities (incomplete oxidation products and excess triethylamine). The crude complex was dissolved into MeOH (300 mL), stirred for ~30 min, and then filtered through celite into a 1 L Erlenmeyer flask. An additional 50 mL of MeOH and 50 mL of water were added to the flask along with acetic acid washed LZY-54 zeolite (40 g). The resulting mixture was agitated or shaken for 3 h, then filtered to remove the zeolite. The zeolite cake was rinsed with MeOH (100 mL) and the rinse solution added to the filtrate. The filtrate was first concentrated to 150 mL and then loaded onto a column (30 cm length×2.5 cm diameter) of pretreated Amberlite IRA-904 anion exchange resin (resin in the acetate form). The eluent containing the bis-acetate lutetium(III) texaphyrin complex was collected, concentrated to dryness under reduced pressure, and recrystallized from anhydrous methanol/t-butylmethyl ether to afford 11.7 g (63%) of a shiny green solid. For the complex: UV/vis: [(MeOH) $\lambda_{max}$, nm (log $\epsilon$)]: 354,414, 474 (5.10), 672, 732; FAB MS, [M–OAc$^-$]$^+$: m/e 1106.4; HRMS, [M–OAc$^-$]$^+$: m/e 1106.4330 (calcd. for $[C_{48}H_{66}N_5O_{10}Lu(OAc)]^+$, 1106.4351). Anal. calcd. for $[C_{48}H_{66}N_5O_{10}Lu](OAc)_2H_2O$: C, 52.74; H, 6.30; N, 5.91. Found: C, 52.74; H, 6.18; N, 5.84.

EXAMPLE 9

Stepwise Synthesis of Texaphyrin- and Sapphyrin-Oligonucleotide Conjugates

The present example provides synthetic procedures in which a texaphyrin or a sapphyrin is inserted directly into a nucleic acid synthesis scheme, preferably on a solid support. Texaphyrin and sapphyrin macrocycles were not known to be stable under the basic conditions employed in the synthesis of oligonucleotides. For example, until the results presented herein were obtained, it was thought that texaphyrin, being a Schiff base, may be unstable to the basic conditions employed during oligonucleotide synthesis, specifically during the ammonia and ethanol cleavage and deprotection steps. It was also possible that the meso positions of sapphyrin would be unstable to the same basic conditions. Therefore, the stepwise synthesis of sapphyrin oligonucleotide conjugates presented herein was a surprising and unexpected result. The synthesis of sapphyrin-nucleobase conjugates is described in U.S. Ser. No. 07/964,607 and PCT/US93/09994, incorporated by reference herein.

It is contemplated that the stepwise synthesis provided herein may be performed manually or may be automated, and may be in a solution-phase or on a solid support. Solid support synthesis may be accomplished using an automated or a manual nucleic acid synthesizer. Common solid supports are CPG (control pore glass) and CPS (control pore silica). Other possible solid supports include polystyrene, polyamide/Kieselguhr, and cellulose paper. A preferred embodiment of this method is automated synthesis on a solid support. Attachment of a texaphyrin or sapphyrin to an oligonucleotide during stepwise synthesis obviates the need for a postmodification protocol and a second purification of the product. This results in an improved yield and greatly facilitates scale-up. The texaphyrin may be a free base texaphyrin or may be a texaphyrin metal complex.

The finding that Ln(III) texaphyrins, notably DyT2B2 and EuT2B1, are stable to treatment with ethanolic ammonia for 24 h at ambient temperature suggests that it is possible to derivatize oligomers with lanthanide(III) texaphyrin complexes during stepwise synthesis.

A texaphyrin or metal complex thereof may be inserted into the synthesis scheme of an oligonucleotide in a variety of ways. Possible linkages include amide, phosphate, thioether, amino, and ether linkages. An amide linkage represents the reaction of an activated carboxylic acid derivative of a macrocycle and an amino linker attached to an oligonucleotide. Activation may be achieved in solution phase or on a solid support using DCC and NHS, EDC, or activated esters of NHS, nitrophenyl, pentachlorophenyl, acid anhydride, or sulfonyl chloride. In addition, for the solid support reaction, activation may be in the form of an acid chloride. A phosphate linkage represents the reaction of an activated phosphate derivative of a macrocycle and the 5' hydroxyl group on an oligonucleotide. The activated phosphate may be a phosphoramidite, an H-phosphonate, a triester, or a diester.

Figure 6A:
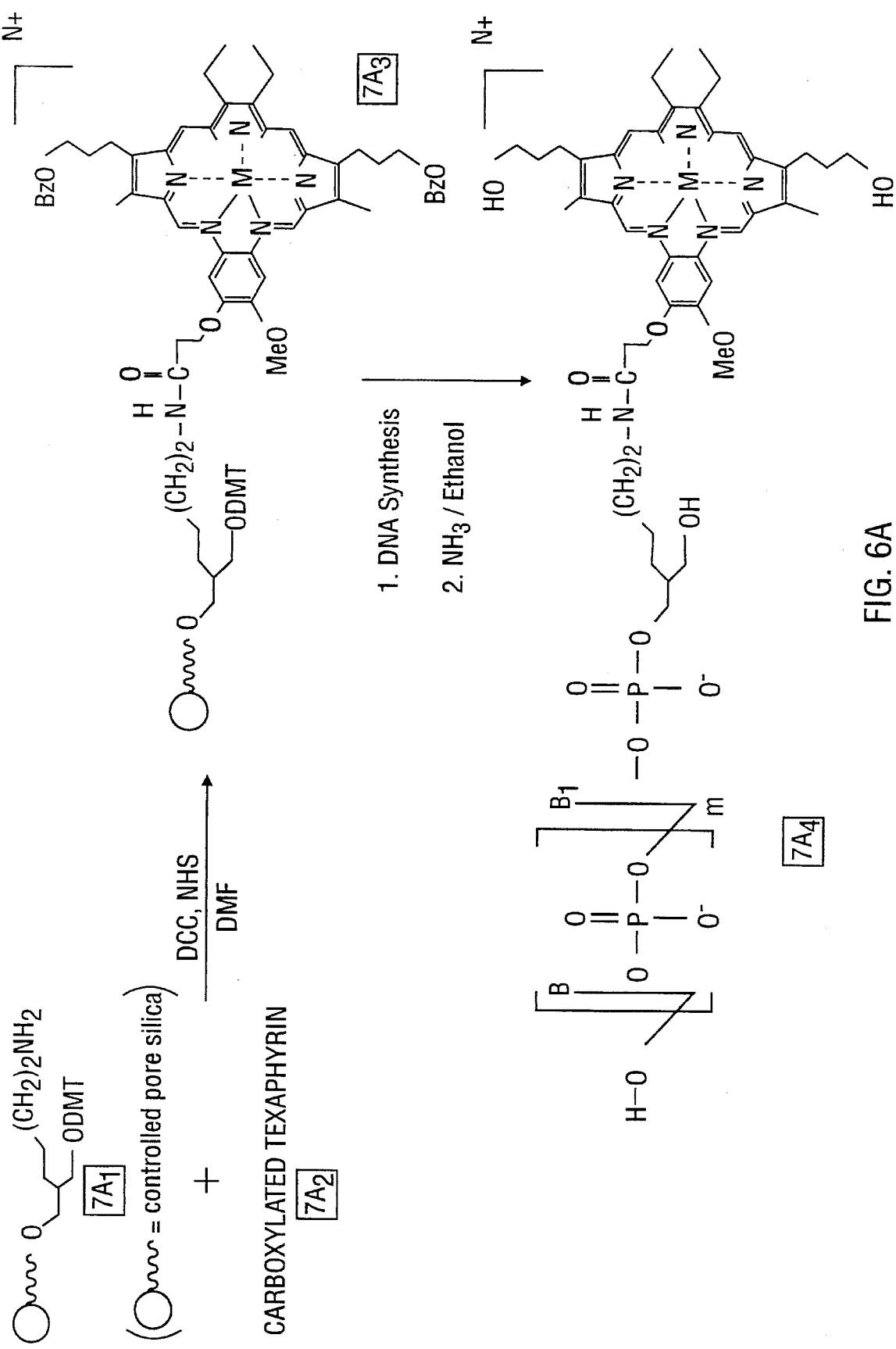
FIG. 6A, FIG. 6B, FIG. 6C, FIG. 6D, FIG. 6E, FIG. 6F and FIG. 6G show stepwise synthesis schemes for preparing texaphyrin metal complex-oligonucleotide conjugates and sapphyrin oligonucleotide conjugates.

Four representative synthetic schemes are discussed here. In the approach depicted in FIG. 6A, a metal-txp complex $7A_2$ is attached to a solid support $7A_1$ via a six carbon amine linker. This amide-forming coupling reaction is currently employed to attach the complex post-synthetically. It is important to note that texaphyrin hydroxyl groups are protected as an ester on $7A_3$ for stepwise synthesis. These protecting groups are labile to the ethanolic ammonia treatment. Such a metal-txp-derivatized support may be used for stepwise synthesis, and upon cleavage and deprotection, results in a 3'-linked metal-txp-DNA conjugate $7A_4$. The amide-forming reaction may also occur at the conclusion of DNA synthesis before deprotection and cleavage from the solid support.

Figure 6B:
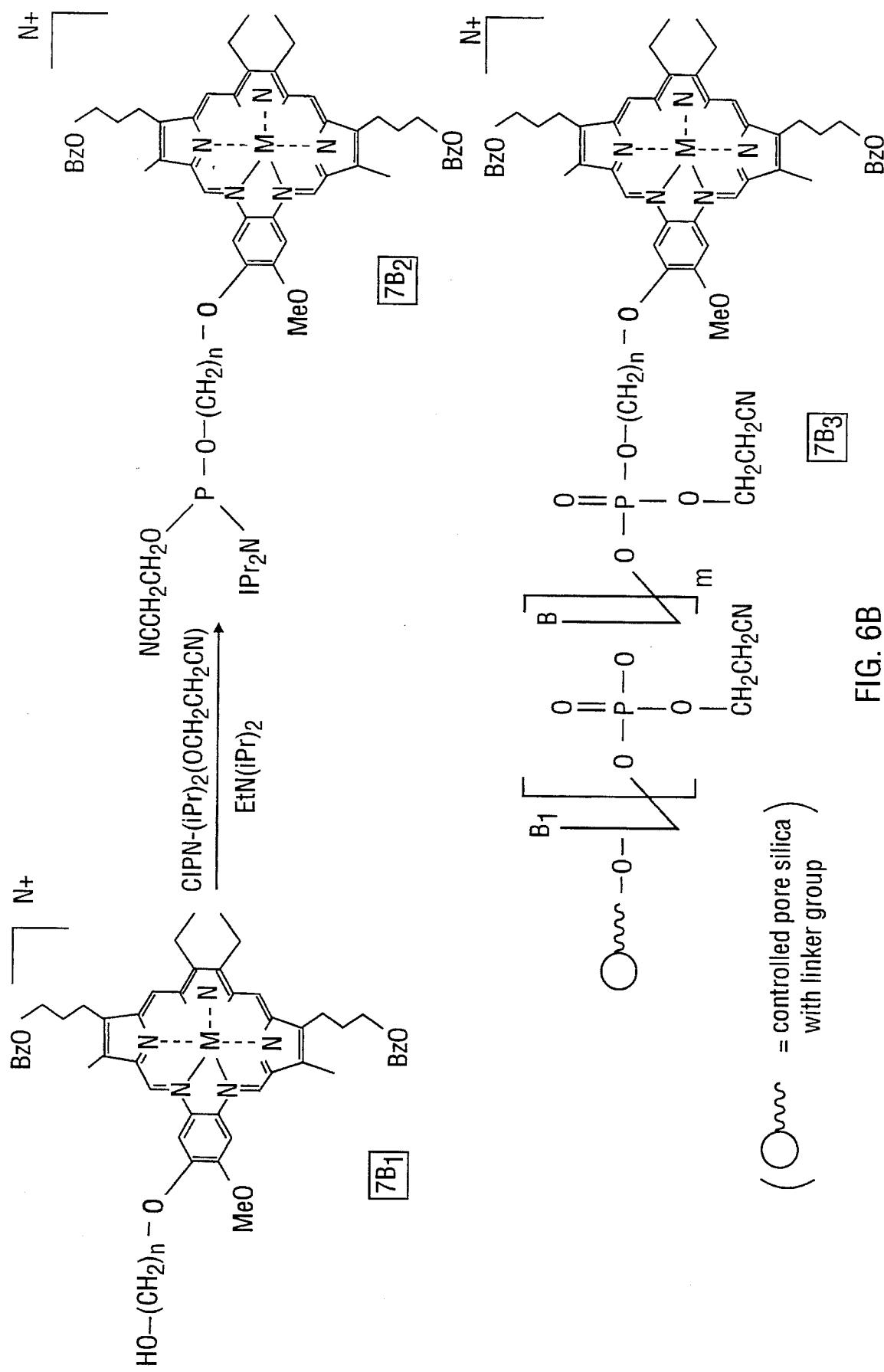
Figure 6C:
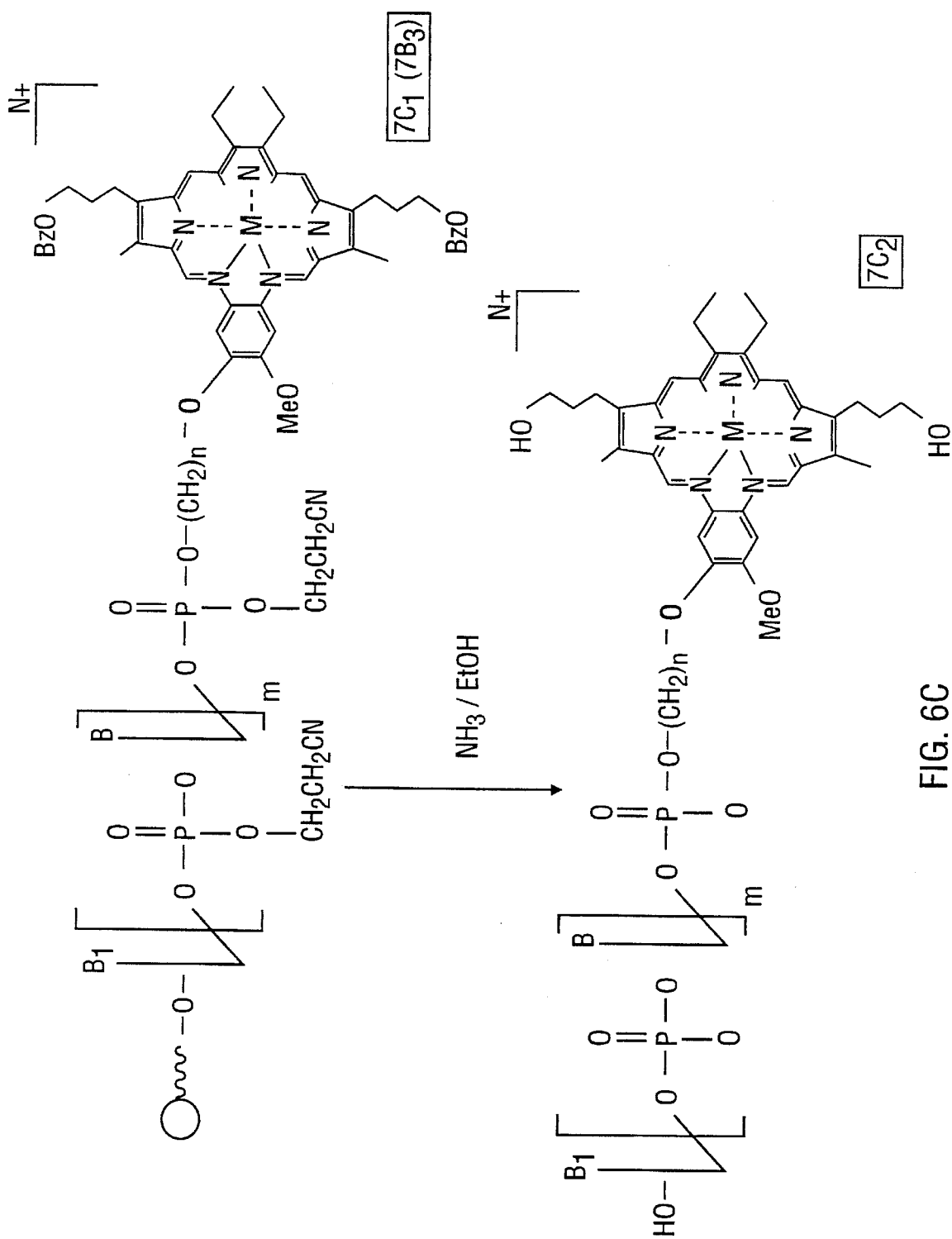

As depicted in FIG. 6B, a phosphoramidite derivative of a metal texaphyrin complex $7B_2$ is prepared by reaction of the monoalcohol $7B_1$ with phosphitylating agent and diisopropylethylamine. The hydroxyl groups are again protected as the ester for this synthesis. The resulting phosphoramidite is coupled on the synthesizer as the final residue to form $7B_3$. In this approach, deprotection results in a 5'-linked txp-metal complex-DNA conjugate $7C_2$. This txp-conjugate has no amide bonds in the linker.

A txp-DNA conjugate having the texaphyrin in an internal linkage to the oligonucleotide may be synthesized using this stepwise approach. A dihydroxytexaphyrin is treated with dimethoxytritylchloride in the presence of dimethylaminopyridine and pyridine. The resulting monoprotected texaphyrin is treated with phosphitylating agent and diisopropylethylamine to produce a monoprotected phosphoramidite. This product is coupled to a growing oligonucleotide during synthesis in place of a nucleotide residue to insert a texaphyrin in an internal linkage. The monoconjugate may then be further coupled to nucleotides to produce a txp-DNA conjugate having the texaphyrin in an internal linkage to the oligonucleotide. Additionally, phosphonate or phosphodiester derivatives of texaphyrin may be utilized to form similar internal, 3', or 5' linkages by the phosphonate or triester methods, respectively.

Oligonucleotide analog conjugates may be coupled to texaphyrins in a similar manner as herein described. In particular, phosphorothioates, 2'-O-methylated ribonucleotides, or other nucleic acid analogs such as methyl phosphonate derivatives are preferred due to the enhanced stability the derivatization provides towards nucleases in vivo.

Other macrocycles may be coupled to oligomers to form macrocycle-nucleic acid conjugates in a similar manner, for example, sapphyrin-oligonucleotide conjugates have been made using a direct coupling amide linkage method or by incorporation during oligonucleotide synthesis forming a 5' linkage via the H-phosphonate method as follows.

Figure 6D:
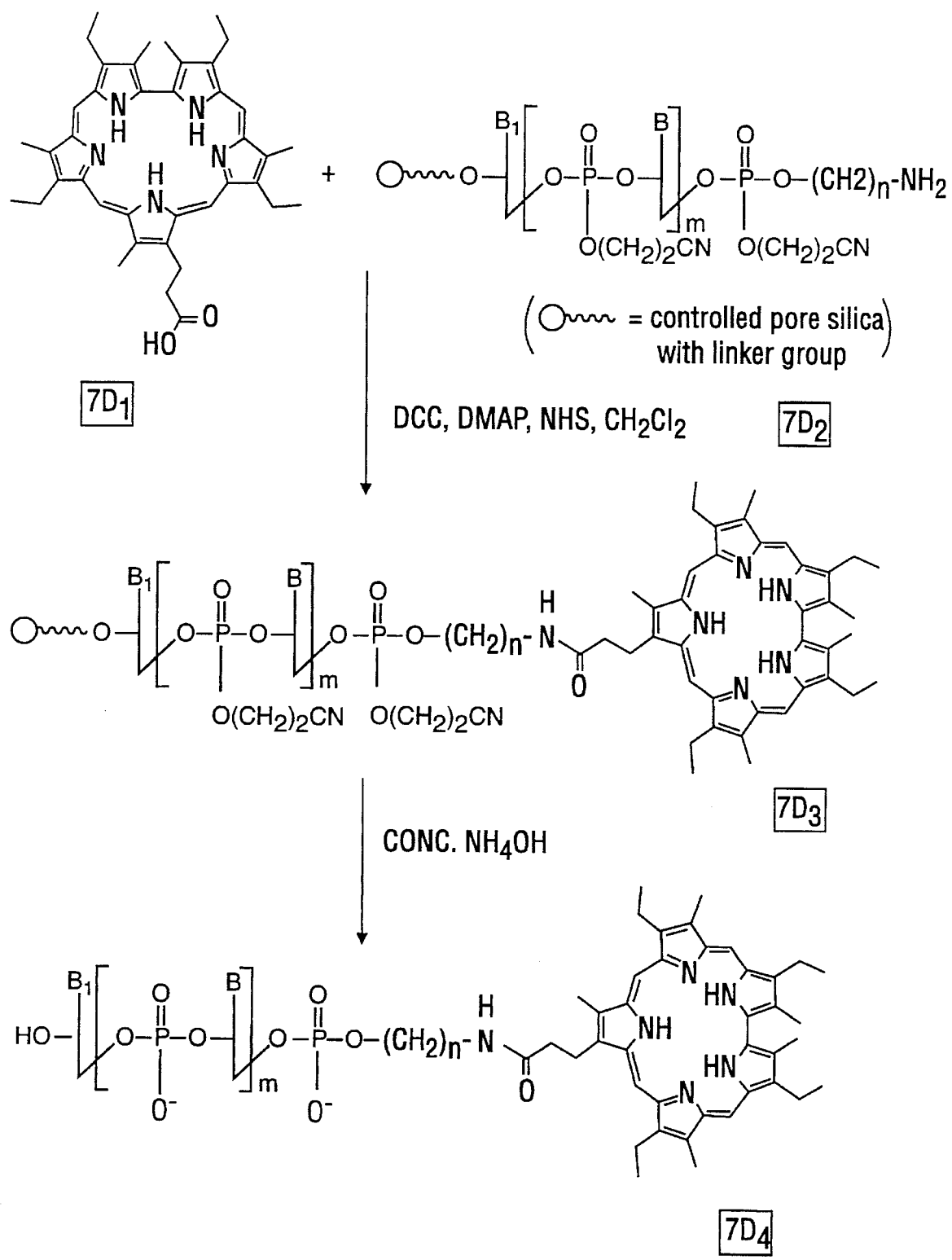

Direct coupling method (amide linkage): Sapphyrin-oligonucleotide conjugates with an amide linkage were formed on a solid support (FIG. 6D). Specifically, sapphyrin monoacid $7D_1$ (6.8 mg, 0.011 mmol, 50 eq) was dissolved in 2 mL of methylene chloride in a 4 mL glass vial with a small stirbar followed by cooling to 0° C. with an ice bath. Dicyclohexylcarbodiimide (4.5 mg, 0.022 mmol, 100 eq), dimethylaminopyridine (0.001 mg, catalytic amount), and N-hydroxysuccinimide (2.5 mg, 0.022 eq, 100 eq) were added to the solution which was then stirred for 30 min. Protected amino- derivatized oligonucleotide attached to CPG solid support ($7D_2$ 2.5 mg, 0.108 μmol, 1 eq) was added to the solution which was stirred overnight at room temperature. The solution was filtered and the conjugate attached to the CPG ($7D_3$) was washed once with methylene chloride and twice with methanol. The green solids were then suspended in conc. ammonium hydroxide for 4 h at room temperature after which the green solution was filtered and evaporated to afford the crude sapphyrin-oligonucleotide conjugate $7D_4$. The conjugate $7D_4$ could be purified by fplc on a $C_{18}$ column using acetonitrile/100 mM triethylammonium acetate, pH 7.0.

This method is similar to that described to form texaphyrin-oligonucleotide conjugates. The coupling step in this case was done on a solid support although it may be done in solution. This procedure attaches sapphyrin to the 5' end, of the oligonucleotide and could be modified to link macrocycles to the 3' end, or internal to an oligonucleotide.

Figure 6E:
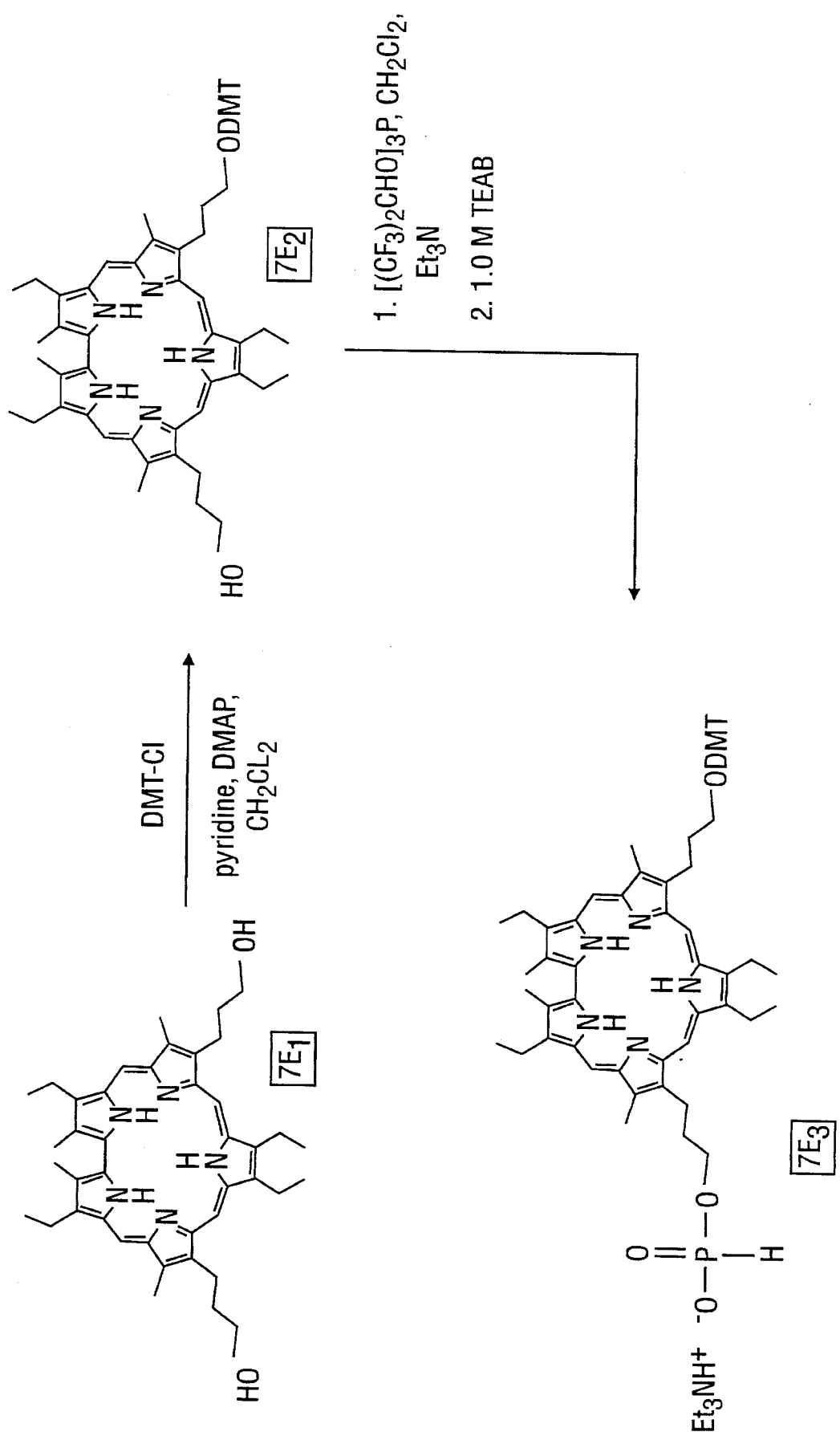
Figure 6F:
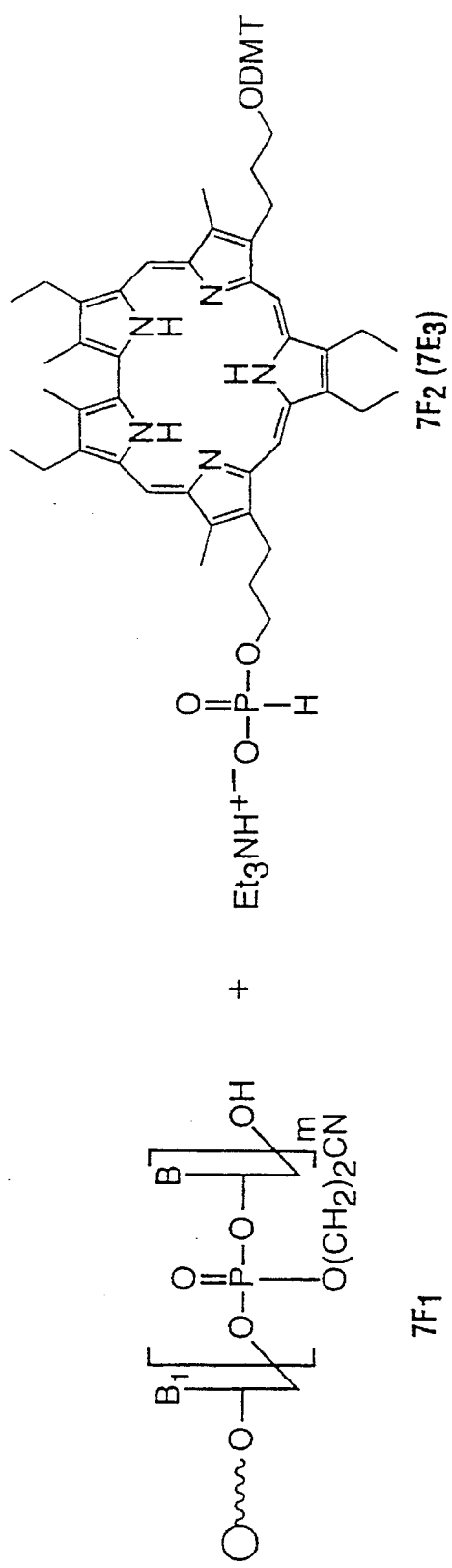
Figure 6F:
Figure 6F:
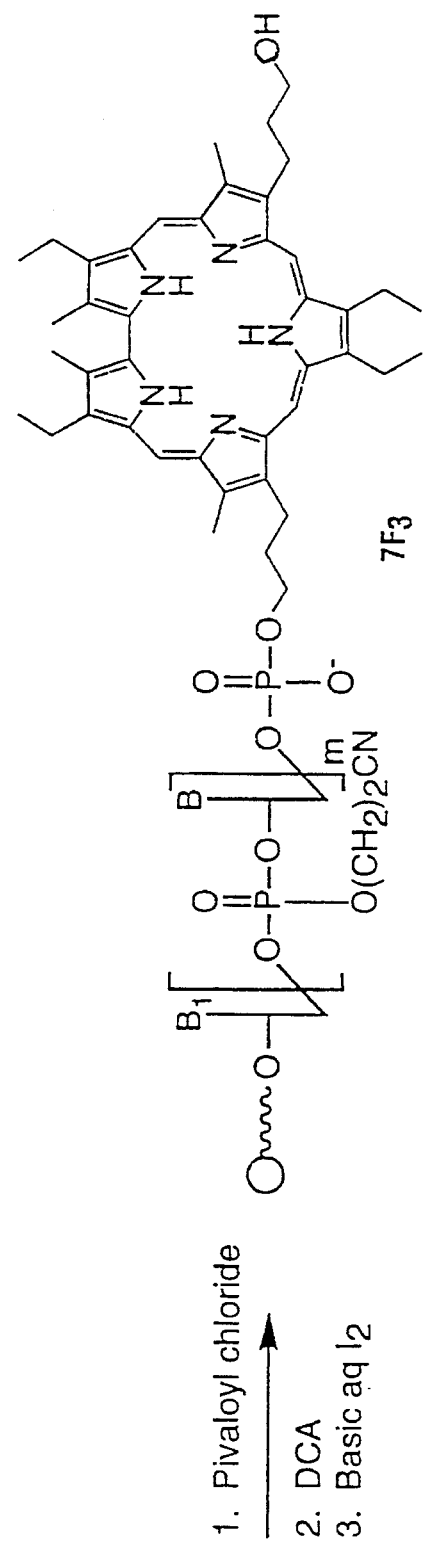
Figure 6G:
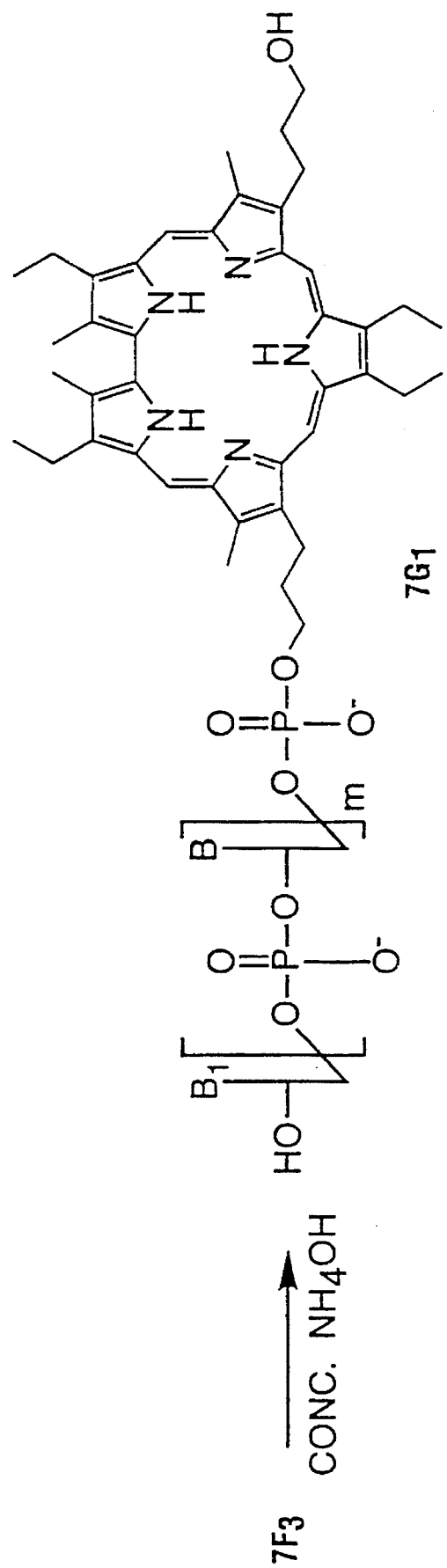

Incorporation during oligonucleotide synthesis (phosphate linkage): The monoprotected sapphyrin H-phosphonate $7F_2$ ($7E_3$) was synthesized for incorporation during oligonucleotide synthesis (FIG. 6E). A sapphyrin-conjugate $7G_1$ was synthesized in a solid-phase manual oligonucleotide synthesizer via the H-phosphonate method (FIG. 6F and FIG. 6G). The oligonucleotide was assembled on a solid support such as controlled pore glass (CPG) by a cycle of steps. The 5' end of the growing oligonucleotide was deprotected, the reaction phase was neutralized, and the activated monoprotected nucleotide H-phosphonate was coupled at the 5' end of the oligonucleotide. Derivatized sapphyrin $7F_2$ ($7E_3$) was incorporated at the 5' end of the oligonucleotide $7F_1$ during the last step of the synthesis in place of a nucleotide (FIG. 6F).

Specifically, the desired oligonucleotide was synthesized on a CPG solid support on a 0.2 μM scale. The derivatized sapphyrin $7F_2$ ($7E_3$) was attached to the oligonucleotide $7F_1$ on a manual oligonucleotide synthesizer (Cruachem PS 150 DNA Synthesizer, Sterling, Va.). The synthesis was run under argon (5 psi). Syringes were oven-dried and kept in a desiccator until use. The following sequence was used for coupling:
1. Wash—acetonitrile—2 min.
2. Deblock—3% dichloroacetic acid in methylene chloride—3 min.
3. Wash—acetonitrile—2 min.
4. Wash—acetonitrile/pyridine (1:1)—2 min.
5. Couple—4 mM derivatized sapphyrin $7F_2$ ($7E_3$) (1 eq) in methylene chloride and 65 mM pivaloyl chloride in acetonitrile/methylene chloride (1:1)—30 μL solution alternating for 1.5 min.
6. Wait—15 min.
7. Wash—acetonitrile, acetonitrile/pyridine (1:1), acetonitrile—2 min, 1 min, 2 min.
8. Deprotect—3% dichloroacetic acid in methylene chloride—3 min.
9. Wash—acetonitrile, acetonitrile/pyridine (1:1)—2 min, 2 min.
10. Oxidize—0.1M iodine in water/pyridine/N-methylimidazole/THF (5/4/1/90), 0.1M iodine in water/triethylamine/THF (5/5/90)—2 min, 2 min.
11. Wash—acetonitrile/pyridine (1:1), acetonitrile, methanol—2 min, 1 min, 2 min.

The conjugate $7F_3$ attached to CPG was added to 2 mL conc. ammonium hydroxide for 4 h. The solution was filtered and the filtrate was evaporated to afford crude sapphyrin-oligonucleotide conjugate $7G_1$ which could be purified by fplc on a $C_{18}$ column using acetonitrile/100 mM triethylammonium acetate pH 7.0.

This method may be used to synthesize any type or length of oligonucleotide with macrocycle modifications at the 5' end or in the interior of the oligonucleotide. Additionally, the oligonucleotide could be modified with multiple macrocycles.

A further method for the synthesis of macrocycle-oligonucleotide conjugates is to incorporate nucleotides enzymatically. A variety of DNA and RNA polymerases may be used, however, the Klenow fragment of DNA polymerase I from *E. coli* and terminal deoxynucleotidyl transferase are preferred. Goodchild, J. (1990) provides a general discussion of the enzymatic synthesis of oligonucleotides and is incorporated by reference herein.

EXAMPLE 10

Site-Specific Light-Dependent Cleavage of DNA by LuTxp-Oligonucleotide Conjugate The present example provides for the site-specific light-dependent cleavage of DNA by Lutetium(III) texaphyrin-oligonucleotide conjugate. DNA samples were incubated with LuB2T2txp, or LuTxp-complementary oligonucleotide conjugate, under an oxygen or argon atmosphere and separated by gel electrophoresis.

A reaction mixture was prepared by adding ca. 300,000 cpm of 5'-$^{32}$P-labeled DNA 36-mer ($8_B$ of FIG. 7) (4 µL) to a solution made from lutetium(III) texaphyrin conjugate ($8_A$ of FIG. 7 where LuTx is $5_C$ of FIG. 4, M is Lu) (2.5 µL, 407 nM stock solution), 4× buffer (5 µL) and water (8.5 µL) to produce a final volume of 20 µL. Final conjugate concentration was 50 nM. The 4× buffer is 400 mM NaCl, 200 mM HEPES, pH 7.5, 100 µM EDTA. Eight reaction mixtures were pipetted into O-ring type Eppendorf tubes (1.6 mL). Two additional reaction mixtures (tubes 1 and 6) were prepared in the same way, except that an equal volume of water was substituted for the LuTx-DNA conjugate. Tubes 1–5 were covered with an atmosphere of oxygen, and tubes 6–10 with an atmosphere of argon. Samples were sealed with parafilm, vortexed and centrifuged briefly, and then irradiated with laser light via the side of the Eppendorf tube. The laser was set at 752 nm and a power density of ca. 150 mW/cm$^2$ was used (ca. 20% reduction of laser power density is estimated to occur due to attenuation by the Eppendorf tube). Samples were irradiated for 1, 5, 10, or 30 minutes, whereupon the DNA was precipitated with ethanol using standard methods. The samples were resuspended in 50% formamide loading buffer, denatured at 90° C. for 5 minutes, and analyzed by electrophoresis on a 20% denaturing polyacrylamide gel. Lanes 1 and 6, no conjugate control; lanes 2–5, LuTxp-oligonucleotide conjugate in the presence of oxygen and irradiated for 1', 5', 10' and 30'; lane 7–10, LuTxp-oligonucleotide conjugate in the presence of argon and irradiated for 1', 5', 10' and 30'; lanes 11 and 16, no LuTxp controls; lanes 12–15, free LuB2 T2 in the presence of oxygen and irradiated for 1', 5', 10' and 30'; and lanes 17–20, free LuB2T2 in the presence of argon and irradiated for 1', 5', 10' and 30'.

Control reactions containing free lutetium(III) B2T2 texaphyrin were prepared by adding ca. 300,000 cpm of 5'-$^{32}$P-labeled DNA 36-mer $8_B$ (4 µL) to a solution made from lutetium(III) texaphyrin B2T2 (5 µL, 2 µM stock solution), 4× buffer (5 µL) and water (6 µL) to produce a final volume of 20 µL. Final LuB2T2Tx complex concentration was 500 nM. Eight reaction mixtures were pipetted into O-ring type Eppendorf tubes (1.6 mL). Two additional reaction mixtures (tubes 11 and 16) were prepared in the same way, except that an equal volume of water was substituted for the LuB2T2Tx solution. Tubes 11–15 were covered with an atmosphere of oxygen, and tubes 16–20 with an atmosphere of argon. Samples were irradiated, ethanol precipitated, and analyzed by electrophoresis as described above.

The autoradiograph indicated substantial cleavage only in those lanes (2–5, 7–10) which contained the 12-mer LuTx-DNA conjugate. The cleavage sites covered four residues, proximal to the anticipated location of the LuTx-DNA conjugate. Both the location of cleavages and the much greater efficiency of conjugate cleavage relative to that caused by free complex are consistent with a model whereby hybridization of the DNA increases the local concentration of the LuTx and effects site-specific cleavage.

The autoradiograph also contained information regarding cleavage mechanism: The presence of oxygen in reactions 2–5 clearly increased the efficiency of DNA strand breakage. That cleavage occurred at all in lanes 7–10 is presumably attributable either to ambient light prior to the layering with argon, or else to incomplete replacement of the atmosphere in these tubes. The positive effect of oxygen on cleavage implicates singlet oxygen or other oxygen product as the intermediary species responsible for DNA strand breakage.

The maximal extent for cleavage observed was roughly 5% and was obtained after 5 minutes of laser irradiation. It is possible that the actual yield of reaction is far greater, since the initial step in cleavage is likely a nicking step and complete cleavage would be facilitated, for example, in vitro, by an organic base such as piperidine. Not wanting to be bound by theory, it is possible that singlet oxygen attacks a purine base, adenine for example, and causes depurination of double-stranded DNA similar to the Maxam and Gilbert chemical cleavage of DNA.

Further irradiation had no effect on the amount of cleavage. This observation is consistent with self-destruction of the 12-mer LuTx conjugate (which is also composed of DNA) or may reflect an instability of the LuTx complex towards laser light. The disappearance of low mobility material assigned as non-denatured DNA·LuTx conjugate duplex at greater laser irradiation times provides additional support for these possibilities.

EXAMPLE 11

Sequence Specific Light-Dependent Cleavage of DNA by LuTxp Conjugated to 2'-O-Methyl RNA The present example provides for the site-specific light-dependent cleavage of synthetic DNA 36-mers $11_B$ and $11_D$ by lutetium(III) texaphyrin-2'-O-methyl RNA 15-mer conjugates $11_A$ and $11_C$.

Reaction mixtures were prepared by adding ca. 100,000 cpm of 5'-$^{32}$P-labeled DNA 36-mer $11_D$ or $11_B$ to solutions made from lutetium(III) texaphyrin conjugate $11_A$ (1.0 µL, 968 nM stock solution) or $11_C$ (3.0 µL, 335 nM stock solution), 4× buffer (5 µL) and water to produce a final volume of 20 µL. Final conjugate concentration was 50 nM. The 4× buffer is 400 mM NaCl, 200 mM HEPES, pH 7.5, 100 µM EDTA. Two conjugate-free controls (samples 1 and 8) were prepared by substituting water for conjugate solution. Samples 1, 4–8, and 11–14 were irradiated for 4.5 hours at 37° C. using a 75 watt incandescent light at ca. 9 inches above the heating block. Samples 2, 3, 9, and 10 were incubated without exposure to light at 37° C. The DNA was precipitated with ethanol using standard methods following incubation. Samples 6, 7, 13, and 14 were dissolved in 10% aqueous piperidine solution (50 µL), heated at 90° C. for 30 minutes, then freeze-dried. All samples were resuspended in 50% formamide loading buffer, denatured at 90° C. for 5' and analyzed by electrophoresis on a 20% denaturing polyacrylamide gel. Lanes 1–7, substrate 11D; lanes 8–14, substrate 11B. Lanes 1 and 8, oligodeoxyribonucleotide-free controls; lanes 2, 4, 6, 9, 11, and 13, 50 nM $11_A$; lanes 3, 5, 7, 10, 12, and 14, 50 nM $11_C$; lanes 2, 3, 9, and 10, no light controls; lanes 1, 4–8, and 11–14, 4.5 hour treatment with light; lanes 6, 7, 13, and 14, samples treated with 10% piperidine prior to electrophoresis The autoradiograph indicated substantial cleavage only in those lanes (5, 7, 11, and 13) that contained the appropriate complementary 15-mer LuTxp 2'-O-methyl RNA conjugate. The cleavage sites covered three to four residues, proximal to the anticipated location of the LuTxp complex. These cleavages are consistent with a model whereby hybridization of the 2'-O-methyl-LuTxp conjugates to their complementary sequences of DNA increases the local concentration of the LuTxp and effects site-specific cleavage.

The autoradiograph also contained information regarding cleavage mechanism: Certain positions within the cleavage site are clearly more reactive to cleavage than others. Definitive identification of these more reactive bases awaits further experimentation, but are tentatively assigned to positions containing purine bases.

The maximal extent of cleavage observed was roughly 10%, and was obtained using a piperidine treatment of the light-exposed samples. The effect of this piperidine treatment is at least a 10-fold increase in cleavage products, indicating that initial DNA lesions formed by the photochemical reaction require base assistance to efficiently produce strand breaks. As the extent of light-induced cleavage in non-piperidine-treated lanes is far lower than that obtained using laser irradiation (cf., Example 10) it may be possible to observe an increase in the yield of cleavage products by using both laser and piperidine treatments.

A txp-oligonucleotide conjugate of a derivatized RNA such as the 2'-O-methyl RNA analog used herein may provide stability against self-cleavage. RNA is hydrolyzed by LuTxp, however, the 2'-O-Me RNA lacks a 2'-OH and, therefore, is stable to hydrolysis. Therefore, an RNA analog oligomer may be more stable than a DNA oligomer for the Txp-oligonucleotide conjugate. The synthesis of RNA analog-conjugates is the same as for Txp-DNA conjugates discussed previously herein. An RNA-analog conjugate may be complementary to an antisense or a sense strand of DNA and forms a triple helix in the process of binding to a double helix.

EXAMPLE 12

Photodynamic Therapy using LaB2T2 and LuB2T2

The present example provides data demonstrating that diamagnetic complexes of texaphyrin are effective in treatment of tumor cells in vitro and in vivo.

In vitro data and experiments. The lanthanum complex of B2T2 [4,5-diethyl-10,23-dimethyl-9,24-bis(3-hydroxypropyl)- 6,17-(3-hydroxypropyloxy)-13,20,25,26,27-pentaazapentacyclo [$20.2.1.1^{3,6}.1^{8,11}.0^{14,19}$]heptacosa-1,3,5,7,9, 11(27),12,14(19),15,17,20,22 (25),23-tridecaene] (LaB2T2) was used at concentrations of 5.0, 1.0 or 0.1 micromolar in tissue culture medium. The murine mammary carcinoma cell line designated EMT-6 was cultured in medium containing LaB2T2 for 1 hour or 3 hours in the dark. Experimental cultures were irradiated with 10 Joules/cm$^2$ using an arc lamp with a 750 nanometer band pass filter. Cell survival was measured using a cell cloning assay. There was no dark toxicity indicating that LaB2T2 had no direct toxicity to the cells. Cultures which were irradiated with the visible red light showed viabilities of 3%, 50% and 100% for concentrations of LaB2T2 of 5.0, 1.0 and 0.1 micromolar respectively. The results were similar for 1 and 3 hour incubation periods. The results established that LaB2T2 was phototoxic to these tumor cells in vitro.

In vivo experiments. Murine adenocarcinoma cells were inoculated into both flanks of Balb/c mice. Four days later, palpable tumor masses were present on both flanks of the mice. Ten mg/kg of lutetium B2T2 (LuB2T2) in aqueous solution was injected IV. Seven hours later, one tumor mass was irradiated with 500 Joules of Argon laser light at 746 nanometers. The unirradiated tumor served as a control. Animals were monitored daily and tumor measurements were made using calipers. Following a single treatment, 65% cell kill was estimated based on the reduction in size of the treated tumors. No phototoxicity of skin or normal tissues surrounding the tumors was observed indicating relatively selective uptake of the LuB2T2 in the tumors. This experiment established the in vivo photodynamic activity of LuB2T2.

EXAMPLE 13

Photodynamic Therapy with LuT2BET

The present example demonstrates the effectiveness of using a preferred lutetium-texaphyrin T2BET complex for photodynamic treatment of tumor cells in vivo.

SMT6 mammary tumor cells were inoculated subcutaneously into the right rear flank of DBA/2Ha mice. When the tumors were approximately 0.5 cm in diameter, the mice were injected with either 40 mg/kg LuT2BET (2 mg/mL in 5% mannitol) or 5% mannitol alone (control) by IV injection in the tail vein. In each treatment group, four mice were injected with the texaphyrin material and two mice with the control material. Laser treatment was given at 1 hr after injection (Group I), 3 hr after injection (Group II), 5 hr after injection (Group III) or 14 hr after injection (Group IV). The tumors were irradiated with approx. 150 J/cm$^2$ of 732 nm laser light. An additional control group (Group V) received no injection and no light treatment. Tumor size was measured prior to irradiation, then again at 24 and 72 hr after laser irradiation and three times a week thereafter.

The laser treatment 1 hr post injection proved to be too soon at this dose level; all animals died from toxicity within one day. The animals irradiated at 3 hr post injection appeared ill. Ulceration was visible in the area of tumor following laser exposure in most of the mice in all groups that received the texaphyrin. No phototoxicity of skin or tissues at or near the tumor was observed in the control mice, which received no texaphyrin. At day 7 following laser treatment the survival rate and the average increase in tumor size for the surviving animals are shown in Table 2 below.

TABLE 2

| Survival and Tumor Size at Day 7 | | |
|---|---|---|
| Treatment | Dead/Alive | Avg. % Increase Tumor Volume |
| Control - no mannitol, no laser | 0/4 | 465 |
| Control - mannitol + laser | 2/6 | 611 |
| Grp I: LuTxp + laser 1 hr post | 4/0 | — |
| Grp II: LuTxp + laser 3 hr post | 1/3 | −23 |
| Grp III: LuTxp + laser 5 hr post | 0/4 | 194 |

TABLE 2-continued

Survival and Tumor Size at Day 7

| Treatment | Dead/Alive | Avg. % Increase Tumor Volume |
|---|---|---|
| Grp IV: LuTxp + laser 14 hr post | 1/3 | 399 |

As can be seen from the Table, the tumors of those animals exposed to light at 5 hr post injection had a much smaller increase in tumor volume after 7 days and all surviving animals exposed at 3 hr post had actual decreases in tumor size. At the termination of the experiment sixty days following injection and treatment, two of the mice in Group III (laser at 5 hr) were still alive and with no visible signs of a tumor. The deaths of the animals in Group II (laser at 3 hr) were likely due to toxicity from laser treatment too soon after texaphyrin dosing.

Following the above procedures, SMT6 tumor-being mice were treated with different doses of LuT2BET (2 mg/mL in 5% mannitol), as follows: Group I, 40 μmol/kg; Group II, 20 μmol/kg; Group III, 10 μmol/kg; and Group IV, 5 μmol/kg. All of the mice, including controls, were irradiated at 5 hours post-injection with a single laser dose of 150 J/cm$^2$ of 732 nm light. Ulcers were observed after laser treatment in all mice from Group II and in all but one mouse from Group I. No ulcers were observed in mice from Groups III or IV or the controls. All four of the mice in Group II (20 μmol/kg) and three of the four mice in Group I (40 μmol/kg) were still alive and without recurrence of the tumor 57 days post-injection. A 10 μmol/kg dose of the texaphyrin inhibited growth of tumor as compared to the controls but did not eradicate the tumor. At 5 μmol/kg of the texaphyrin there was a marginal effect.

EXAMPLE 14

In vivo MRI and PDT for Atheroma using GdT2BET and LuT2BET

The present example demonstrates the effectiveness of using a gadolinium texaphyrin T2BET metal complex for imaging and a diamagnetic texaphyrin T2BET metal complex for treating atheroma in vivo. Atheromatous plaque was removed in vivo from the aorta of a rabbit by photodynamic therapy using a texaphyrin diamagnetic-metal complex.

A New Zealand white rabbit was fed a high cholesterol, atherogenic diet (2% cholesterol U.S.P. diet for rabbits (ICN Animal Research Diets, Calif.)) for 4 months. GdT2BET (20 μmol/kg of 2 mM txp complex in 5% mannitol) was then injected intravenously into the rabbit two weeks prior to an MRI scan. The MRI showed an intense contrast enhancement which was related to the Gd-Txp that had accumulated in the atheromatous plaque in the wall of the aorta. In further experiments, successful MRI scans were run at 1 h, 1 day and 1 week post-injection.

The rabbit was then injected intravenously with LuT2BET (20 μmol/kg of 2 mM txp complex in 5% mannitol). Five hours following injection, through a laparotomy incision, red laser light (732 nm) was projected onto a segment of the abdominal aorta. Light exposure was performed for 17 minutes. Subsequently, the laparotomy was closed and the animal was returned to its cage. Four days later, the animal was again injected with GdT2BET, and 1 hour after this final injection the animal was sacrificed and the aorta was removed. There was no gross hemorrhage or damage to the aorta in the vicinity where the laser irradiation had been applied. Axial MRI scans were then obtained at intervals throughout the course of the aorta.

In scans taken both above and below the area of aorta that had been treated with laser light, there was intense contrast enhancement similar to that observed prior to irradiation, the enhancement being caused by the gadolinium texaphyrin accumulation in atheromatous plaque. However, there was no contrast enhancement in the area of the aorta that had been irradiated, indicating that no GdTxp had accumulated in the treated area, which in turn indicates that exposure of a segment of a lutetium texaphyrin-containing aorta to laser light at 732 nm had obliterated the plaque circumferentially in the aorta. Control rabbits (not on an atherogenic diet) injected with GdT2BET had no image contrast enhancement, indicating that GdT2BET had not collected in the walls of their aortas.

This example illustrates the diagnostic potential of an MRI detectable paramagnetic metal texaphyrin complex in detecting atheromatous plaque and also the potential of using a texaphyrin-diamagnetic metal complex and light irradiation to eradicate the atheromatous material. This treatment would be useful for removing atheromatous plaque from other occluded blood vessels as well as an occluded aorta. The light may be localized to the tissue being treated by the use of fiber optics and a laser, for example.

The texaphyrins of the present invention may also be used as detectable probes for high density lipoproteins (HDL) or low density lipoproteins (LDL). A paramagnetic metal-texaphyrin complex bound to either HDL or LDL would be detectable using MRI, or a free base texaphyrin bound to either would be detectable using fluorescence. HDL and LDL may be distinguished to the extent that selective binding to texaphyrin occurs.

EXAMPLE 15

Fluorescence Detection of Texaphyrins

Fluorescent molecules contain chromophores that can be photochemically promoted to an excited state, or higher energy level, by irradiating them with light. Excitation wavelengths are generally in the UV, blue, or green regions of the spectrum. Chromophores can remain in the excited state for about $10^{-9}$ seconds before releasing their energy and returning to the ground state. Those chromophores that dissipate their energy as emitted light are fluorescent. The wavelength distribution of the outgoing photons forms the emission spectrum, which peaks at longer wavelengths (lower energies) than the excitation spectrum, but is equally characteristic for a particular fluorophore.

Texaphyrins are unique as chromophores in that they both absorb and emit light in the red light region, about 700–800 nm wavelengths. The fluorescence emission for texaphyrins occurs about 5–40 nm farther to the red wavelengths in relation to the absorbing wavelengths. Thus, texaphyrins have particular utility in biolocalization and clinical diagnostics and also in in vitro applications such as laboratory and medical research, industry, and agriculture.

Optical characteristics of certain texaphyrin complexes are described in Sessler et al. (1991), incorporated herein by reference. The absorption and emission wavelengths and the amount of fluorescence exhibited by the texaphyrins will vary, depending on the substituents attached to the texaphyrin molecule, the metal with which the texaphyrin forms a complex, and other factors. It has been found that the presence of a metal will often decrease the fluorescence of texaphyrins and that certain Cd-texaphyrin complexes have a comparatively weak fluorescence (Sessler, et al., 1991). The Lu-T2BET complex has a very strong fluorescence with a maximum at 747 nm and a lifetime of (380±15)ps (measured by time-correlated, single-photon counting), whereas the Gd-T2B2 complex has very weak fluorescence.

A particular use of the present invention is the detection and diagnosis of certain types of tissue such as tumors and tumor cells and atheromatous tissue. Texaphyrin compounds show a high intrinsic biolocalization selectivity for lipid-rich tissues such as tumors or neoplastic tissues and atheromas. A texaphyrin complex which exhibits fluorescence is administered to a host, after which the host is exposed to activating light in the 700–800 nm range and the location of the tumor or atheroma is observed as a result of fluorescent light emitted by the localized texaphyrin. A particular advantage to this technology is in cardiovascular applications where atheromatous plaque is "seen" and "obliterated" using only one agent for both detection and treatment. An automated feedback loop is envisioned where the light dose is controlled by the amount of fluorescence emitted. Therefore, light would be provided only to those sites where high initial fluorescence is seen. Such an automated irradiation system has the advantage of using only a single catheter in a clinical setting.

Another embodiment of the use of the present invention is in the detection and subsequent destruction of tumor or atheromatous tissue. A texaphyrin-diamagnetic metal complex which exhibits fluorescence and also exhibits biolocalization in atheromatous and tumor tissue relative to surrounding tissue is administered to a host. Localization sites of the complex in the host are determined by fluorescence of the complex. The complex is then photoirradiated in proximity to the localization sites, such as with the use of a laser or fiber optics, to cause tumor or atheroma tissue destruction by photodynamic therapy.

In another use of the present invention, a texaphyrin molecule, either alone or conjugated to a site-directing molecule, provides a probe, reagent, or assay for detection of a particular target by fluorescence scanning technology. In some instances, such as with certain viruses, the texaphyrin itself attaches to the target without the need for an additional site-directing molecule.

Figure 9A:
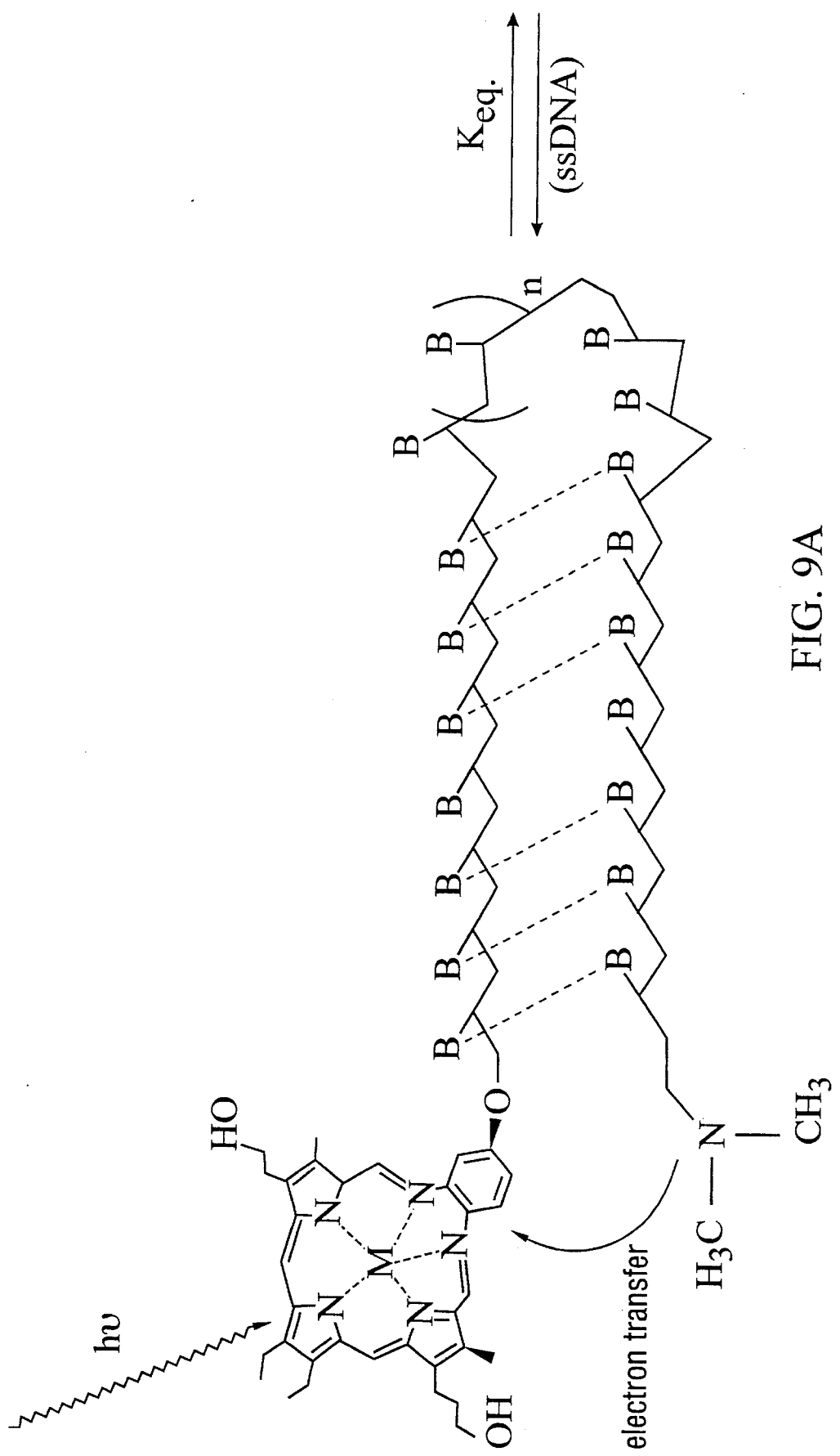

Using stepwise DNA synthesis, a DNA probe may be prepared which bears a metallotexaphyrin chromophore on either the 5'- or the 3' end and an amine on the other end. The sequence is designed as a partial inverted repeat sequence such that the DNA probe forms a relatively weak intramolecular complex called a hairpin, which brings the texaphyrin and amine groups into close proximity ($12_A$ of FIG. 9A, FIG. 9Bi, and FIG. 9Bii). As a consequence of this proximity, the excited electronic state produced by irradiation of the texaphyrin chromophore is rapidly quenched by an electron from the amine group, and is not able to fluoresce or phosphoresce. When a second nucleic acid is present, however, which is complementary in sequence to the probe, a duplex forms that is stronger in its absolutely binding affinity than the intrastrand hairpin which, in effect, separates the texaphyrin chromophore from the amine ($12_B$ of FIG. 9A, FIG. 9Bi, and 9Bii). The excited electronic state produced by irradiation of the texaphyrin chromophore is no longer quenched by the amine group and is able to fluoresce. The probe as described thus acts as a "molecular switch", such that an observable signal is returned upon irradiation only in the presence of the complementary nucleic acid. In some applications, mismatches would be allowed in the inverted repeat since it is known that nucleic acids having mismatches will hybridize to each other, albeit less strongly than a perfect match.

Figure 10A:
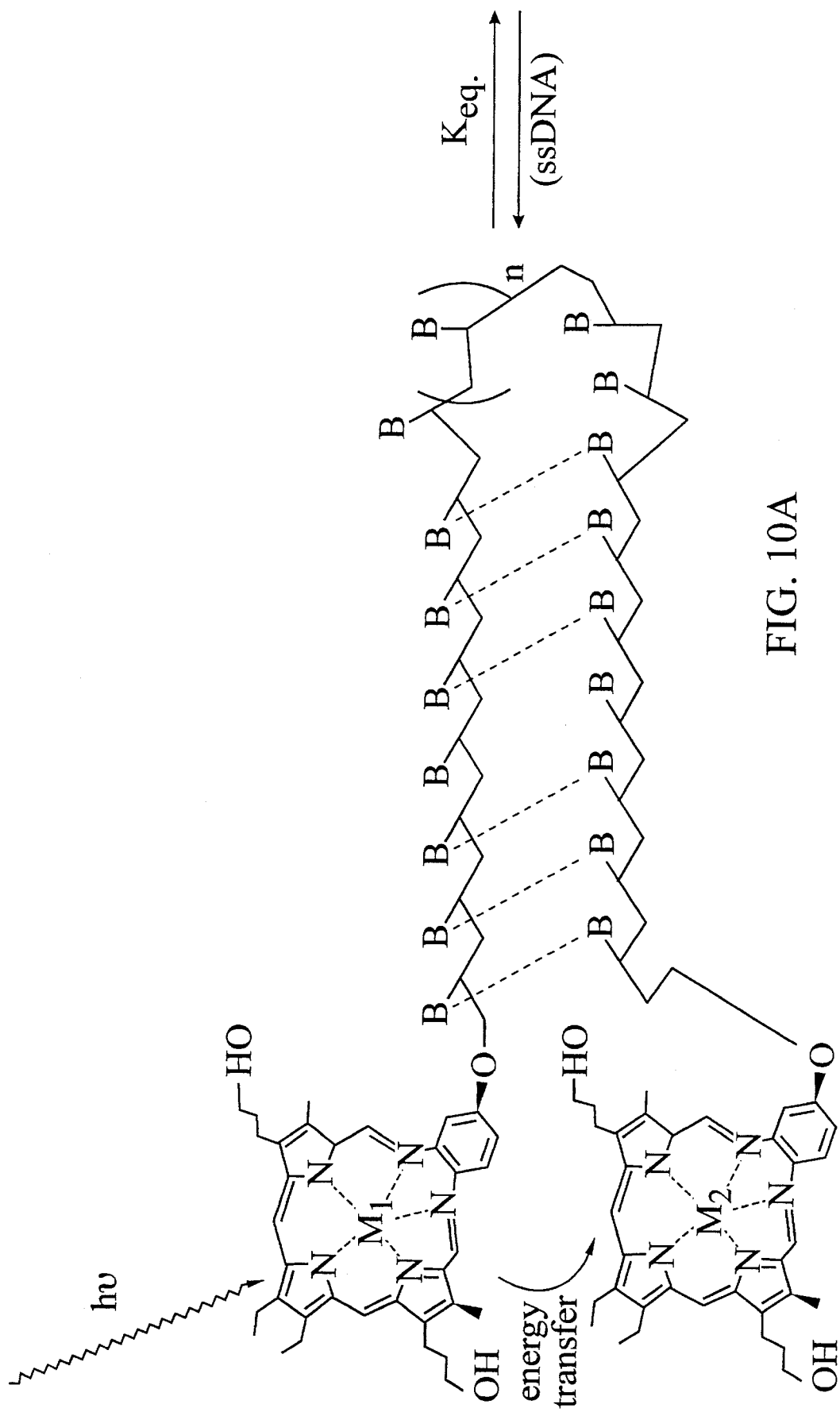

A modification of this concept is illustrated in FIG. 10A, FIG. 10Bi, and FIG. 10Bii. Here, two different texaphyrin chromophores are used. The first of these (the one with $M_1$) is fluorescent by virtue of either containing a diamagnetic metal such as Lu(III) or La(III) or no metal at all (M=H). The second texaphyrin (the one with $M_2$) contains a paramagnetic metal center such as, e.g., Gd(III), Eu(III), etc. It thus replaces the tertiary amine of FIG. 9A, FIG. 9Bi, and FIG. 9Bii, but would quench the fluorescence in the hairpin "state" as the result of energy or exciton transfer from the diamagnetic ($M_1$) texaphyrin excited state produced by irradiation to the paramagnetic ($M_2$) texaphyrin. In the duplex form ($13_B$), such energy transfer fluorescence quenching would be precluded as a result of the larger spatial separation between the diamagnetic $M_1$ texaphyrin donor and the paramagnetic $M_2$ texaphyrin acceptor. Thus, the "switch" is "turned on" due to the greater fluorescence lifetime of the $M_1$ texaphyrin and is further able to perform repeatedly.

Such a probe might find application in developing an in vitro assay for the presence of a particular nucleic acid sequence. For example, a probe might be designed which fluoresces only upon hybridizing with an invariant sequence from the HIV genome, and thus may serve as an efficient way of screening for this virus in blood. Other chromophores such as porphyrins and other fluorescent dyes may serve the purpose, but the texaphyrin has the advantage of a red shifted absorbance. Other groups besides an amine may serve as the electron donor, eg., a carotenoid. A key feature of the system as described is that a positive signal (eg., phosphorescence or fluorescence) is given in the presence of the analyte. It is important to note that the intermolecular duplex is able to compete with the intramolecular hairpin due to the extra stability obtained by binding to the bases in the loop region. Also, as an intramolecular complex (the hairpin) is by definition concentration-independent, the assay can be carried out at a sufficiently low concentration of probe such that intermolecular quenching by another probe does not occur. Thus the equilibrium between open (fluorescent) and closed forms of the probe depends solely on the concentration of the analyte.

The following references are incorporated in pertinent part by reference herein for the reasons cited below.

REFERENCES

Brown, S. B. and T. G. Truscott., *Chemistry in Britain,* 955–958, Nov. 1993.
Caracciolo et al. *Science,* 245:1107, 1989.
Chen, C. H. B. and Sigman, D. S., *J. Amer. Chem. Soc.,* 110:6570– 6572, 1988.
Dervan, *Science,* 232: 464–471, 1986.
Dreyer and Drevan, *Proc. Natl. Acad. Sci. U.S.A.,* 82:968–972, 1985.
Fiel, *Journal of Biomolecular Structure & Dynamics,* 6(6):1259– 1275, 1989.
Goodchild, J., *Bioconjugate Chemistry.,* 1:165–187, 1990.
Grossweiner, L. I., *Lasers, Surg. Med.,* 11:165–173, (1991).
Groves and Farrell, *J. Am. Chem. Soc.,* 111:4998–5000, 1989.
Henderson, B. W. and T. J. Dougherty, *Photochem., Photobiol.,* 55:145–157, 1992.
Kobayashi, et al., *Photomed. Photobiol.,* 15 (1993).
Le Doan et al., *Biochemistry,* 25:6736–6739, 1986.
Le Doan et al., *Bioconjugate Chem.,* 1:108 (1990).
Le Doan et al., *Nucleic Acids Research,* 15(21):8643–8659, 1987.
Lee et al., *Biochemistry,* 27:3197–3203, 1988.
Lin, et al., *Biochemistry,* 28:1054–1061, 1989.
Meunier, B., et al., *Bioconjugate Chem.,* 4:366–371.
Moan, J. and K. Berg, *Photochem. Photobiol.,* 55:931–948, 1992.
PCT/US940/06284.

Praseuth et al., *Photochemistry and Photobiology*, 44:717–724, 1986.

Sessler et al., *Comm. Inorg. Chem.*, 7:333, 1988.

Sessler et al., *SPIE Proc. Soc. Opt. Eng.*, 1426:318–329, 1991.

Sindelar et al., *Arch. Surg.*, 126:318–324, 1991.

Skikes, J. D., *Photochem. Photobiol.*, 43:691, 1986.

Strobel and Dervan, *J. Am. Chem. Soc.*, 111(18):7826–7827, 1989.

U.S. Pat. No. 4,935,498.

U.S. Pat. No. 5,162,509.

U.S. Pat. No. 5,252,720.

U.S. Ser. No. 08/112,872.

U.S. Ser. No. 08/227,370.

Vlassov et al., *Nucleosides & Nucleotides*, 10(103:641–643, 1991.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods, and in the steps or in the sequence of steps of the method described herein without departing from the concept, spirit, and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope, and concept of the invention as defined by the appended claims.

What is claimed is:

1. A method of light-induced cleavage of a polymer of deoxyribonucleic acid, the method comprising:

contacting the polymer with a photosensitive texaphyrin; and exposing the photosensitive texaphyrin to light for a time sufficient to cleave the polymer.

2. The method of claim 1 wherein the exposing step is carried out in the presence of oxygen.

3. The method of claim 1 where the texaphyrin has the structure:

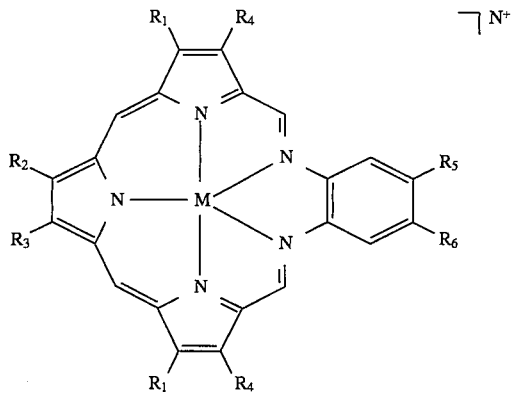

where:

M is H or a diamagnetic metal cation;

$R_1$, $R_2$, $R_3$, $R_4$, $R_5$ and $R_6$ are independently hydrogen, hydroxyl, alkyl, hydroxyalkyl, alkoxy, hydroxyalkoxy, saccharide, carboxyalkyl, carboxyamidealkyl, a site-directing molecule or a couple to a site-directing molecule; and N is an integer less than or equal to 2.

4. The method of claim 3 wherein at least one of $R_1$, $R_2$, $R_3$, $R_4$, $R_5$ and $R_6$ is a site-directing molecule or a couple to a site-directing molecule.

5. The method of claim 4 wherein the site-directing molecule is an oligonucleotide.

6. The method of claim 5 wherein the oligonucleotide is a 2'-O-alkylated ribonucleotide.

7. The method of claim 3 wherein one of $R_3$, $R_5$, and $R_6$ is an oligonucleotide or a couple to an oligonucleotide.

8. The method of claim 3 wherein $R_1$ is $(CH_2)_2CH_2OH$, $R_2$ and $R_3$ are $CH_2CH_3$, $R_4$ is $CH_3$, $R_5$ is a site-directing molecule or a couple to a site-directing molecule and $R_6$ is H.

9. The method of claim 3 where $R_1$ is $(CH_2)_2CH_2OH$, $R_2$ and $R_3$ are $CH_2CH_3$, $R_4$ is $CH_3$, $R_5$ is $O(CH_2CH_2O)_2CH_2CH_2OCH_3$, and $R_6$ is a site-directing molecule or a couple to a site-directing molecule.

10. The method of claim 3 wherein $R_1$ is $(CH_2)_2CH_2OH$, $R_2$ and $R_3$ are $CH_2CH_3$, $R_4$ is $CH_3$, and $R_5$ and $R_6$ are $O(CH_2CH_2O)_2CH_2CH_2OCH_3$.

11. The method of claim 3 wherein $R_1$–$R_6$ are as in Table 1 for texaphyrins A1–A22.

12. The method of claim 3 wherein M is a diamagnetic metal cation and the diamagnetic metal is Lu(III), La(III), In(III), Zn(II) or Cd(II).

13. The method of claim 1 wherein the light has a wavelength range of about 700 to 800 nanometers.

* * * * *

UNITED STATES PATENT AND TRADEMARK OFFICE
CERTIFICATE OF CORRECTION

PATENT NO. : 5,567,687
DATED : October 22, 1996
INVENTOR(S) : Magda et al.

It is certified that error appears in the above-identified patent and that said Letters Patent is hereby corrected as shown below:

In item [63], please delete "Pat. No. 5,242,720" and insert -- Pat. No. 5,252,720 -- therefor.

In item [63], after 'Sep. 30, 1991, abandoned,' please insert -- which is a continuation-in-part of Ser. No. 539,975, Jun. 18, 1990, Pat. No. 5,162,509 -- therefor.

In item [63], after 'which is a continuation of PCT/US90/01208, Mar. 6, 1990,' please delete "which is a continuation-in-part of Ser. No. 539,975, Jun. 18, 1990, Pat. No. 5,162,509, which" and insert -- said Ser. No. 539,975 -- therefor.

In item [63] after 'Pat. No. 4,935,498,' please delete -- said Ser. No. 112,872, is a division of Ser. No. 822,964 --.

Signed and Sealed this

Twenty-ninth Day of April, 1997

*Attest:*

BRUCE LEHMAN

*Attesting Officer*  Commissioner of Patents and Trademarks

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

CTCGGCCATA GCGAATGTTC  20

( 2 ) INFORMATION FOR SEQ ID NO:2:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CTCGGCCATA GC  12

( 2 ) INFORMATION FOR SEQ ID NO:3:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GAACATTCGC TATGGCCGAG AAGATGTCAC CATGGA  36

( 2 ) INFORMATION FOR SEQ ID NO:4:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear (ii) MOLECULE TYPE: RNA (genomic)

(xi) SEQUENCE DESCRIPTION: SEQ ID NO:4:

CAUCUGUGAG CCGGG  15

(2) INFORMATION FOR SEQ ID NO:5:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:5:

CAACACCCGG CTCACAGATG AAGTCTCCAA AATAAA  36

(2) INFORMATION FOR SEQ ID NO:6:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: RNA (genomic)

(xi) SEQUENCE DESCRIPTION: SEQ ID NO:6:

CUCGGCCAUA GCGAA  15